(12) United States Patent
Andrews et al.

(10) Patent No.: US 8,592,403 B2
(45) Date of Patent: Nov. 26, 2013

(54) DIAZEPINE AND DIAZOCANE COMPOUNDS AS MC4 AGONISTS

(75) Inventors: Mark David Andrews, Sandwich (GB); Christopher Gordon Barber, Sandwich (GB)

(73) Assignee: Pfizer Limited, Sandwich, Kent (GB)

(*) Notice: Subject to any disclaimer, the term of this patent is extended or adjusted under 35 U.S.C. 154(b) by 309 days.

(21) Appl. No.: 13/057,319

(22) PCT Filed: Jul. 30, 2009

(86) PCT No.: PCT/IB2009/053317
§ 371 (c)(1),
(2), (4) Date: Feb. 3, 2011

(87) PCT Pub. No.: WO2010/015972
PCT Pub. Date: Feb. 11, 2010

(65) Prior Publication Data
US 2011/0136814 A1   Jun. 9, 2011

Related U.S. Application Data

(60) Provisional application No. 61/086,530, filed on Aug. 6, 2008.

(51) Int. Cl.
*A61K 31/33* (2006.01)
*C07D 245/00* (2006.01)
*C07D 245/02* (2006.01)

(52) U.S. Cl.
USPC .......................................... 514/183; 540/470

(58) Field of Classification Search
None
See application file for complete search history.

(56) References Cited

U.S. PATENT DOCUMENTS

| | | | |
|---|---|---|---|
| 3,752,814 A | 8/1973 | Fluckiger et al. | 260/268 |
| 3,752,888 A | 8/1973 | Fluckiger et al. | 424/250 |
| 4,929,629 A | 5/1990 | Jeffery et al. | 514/646 |
| 5,274,143 A | 12/1993 | Ramig et al. | 554/123 |
| 5,420,305 A | 5/1995 | Ramig et al. | 549/292 |
| 5,521,186 A | 5/1996 | Heeres et al. | 514/252 |
| 5,540,917 A | 7/1996 | Isler et al. | 424/78.01 |
| 5,624,941 A | 4/1997 | Barth et al. | 514/326 |
| 5,643,874 A | 7/1997 | Bremer et al. | 514/12 |
| 5,747,524 A | 5/1998 | Cullinan et al. | 514/443 |
| 5,929,075 A | 7/1999 | Heeres et al. | 514/252 |
| 6,265,431 B1 | 7/2001 | Muller et al. | 514/408 |
| 6,432,984 B1 | 8/2002 | Barthe et al. | 514/326 |
| 6,518,264 B2 | 2/2003 | Achard et al. | 514/210.01 |
| 7,151,097 B2 | 12/2006 | Carpino et al. | 514/211.05 |
| 2002/0141985 A1 | 10/2002 | Pittner et al. | 424/94.1 |
| 2004/0092520 A1 | 5/2004 | Griffith et al. | 514/242 |
| 2004/0157839 A1 | 8/2004 | Griffith et al. | 514/227.8 |
| 2004/0214838 A1 | 10/2004 | Carpino et al. | 514/262.1 |
| 2004/0214855 A1 | 10/2004 | Carpino et al. | 514/303 |
| 2005/0176772 A1 | 8/2005 | Calabrese et al. | 514/326 |

FOREIGN PATENT DOCUMENTS

| | | | | |
|---|---|---|---|---|
| WO | 9806705 | * | 2/1998 | ........... C07D 239/42 |
| WO | WO 9820001 | | 5/1998 | ........... C07D 241/04 |
| WO | WO 0035298 | | 6/2000 | ............... A23G 3/30 |
| WO | WO 02068387 | | 9/2002 | |
| WO | WO 02068388 | | 9/2002 | |
| WO | WO 02076949 | | 10/2002 | ......... A61K 31/4196 |
| WO | WO 03027637 | | 4/2003 | |
| WO | WO 03075660 | | 9/2003 | ............. A01N 43/00 |
| WO | WO 2004012671 | | 2/2004 | |
| WO | WO 2004013120 | | 2/2004 | ........... C07D 317/62 |
| WO | WO 2004048317 | | 6/2004 | ........... C07C 235/20 |
| WO | WO 2007015162 | | 8/2007 | |

OTHER PUBLICATIONS

"Diabetes insipidus", Http://www.nlm.nih.gov/MEDLINEPLUS/ency/article/000460.htm, accessed Aug. 26, 2009.*
"Obesity-Prevention", http://www.mayoclinic.com/health/obesity/ds00314/dsection=prevention, accessed May 19, 2010.*
Chaki, et al., *Drugs of the Future*, The MC4 receptor as a therapeutic target, vol. 29(10), pp. 1065-1074, (2004).
Fan, et al., *Nature*, Role of melanocortinergic neurons in feeding and the *agouti* obesity syndrome, vol. 385, pp. 165-168, (1997).
Harper, et al., Journal of Medicinal Chemistry, Synthesis of some N-substituted 3,5-dimethyl-4-piperidinols and their derivatives as potential analgesics. vol. 7(6), pp. 726-728 (1964).
Hinney, et al., *Journal of Clinical Endocrinology and Metabolism*, Several mutations in the melanocortin-4 receptor gene including a nonsense and a frameshift mutation associated with dominantly inherited obesity in humans, vol. 84(4), pp. 1483-1486, (1999).
Huszar, et al., *Cell* (Cambridge, Massachusetts), Targeted disruption of the melanocortin-4 receptor results in obesity in mice. vol. 88(1), pp. 131-141, (1997).
Liang, et al., Expert Opinion in Therapeutic Patents, "Fast-dissolving intraoral drug deliver system", vol. 11 (6), 981-986, (2001).
Lieberman, et al., Pharmaceutical Dosage Forms: Tablets, vol. 1, (1980).

(Continued)

*Primary Examiner* — Noble Jarrell

(57) ABSTRACT

The present invention relates to compounds of formula (I) wherein $R^1$, $R^2$, $R^3$, $R^4$, L and n are as defined in the specification. These compounds are useful as MC4 agonists.

14 Claims, No Drawings

(56) References Cited

OTHER PUBLICATIONS

Lu, et al., Nature, Agouti protein is an antagonist of the melanocyte-stimulating-hofmone receptor, vol. 371, pp. 799-802, (1994).

March, Jerry; *Advanced Organic Chemistry*: Reactions, Mechanisms, and Structure, Fourth Edition, pp. 378-383, (1992).

Mizuno, et al. *Endocrinology*, Fasting regulates hypothalamic neuropeptide Y, agouti-related peptide, and proopiomelanocortin in diabetic mice independent of changes in leptin or insulin, vol. 140(10), pp. 4551-4557, (1999).

Ollmann, et al., *Science*, Antagonism of Central Melanocortin Receptors in Vitro and in Vivo by Agouti-Related Protein, vol., pp. 135-138., (1997).

Vaisse, et al., *Nature Genetics*, A frameshift mutation in human MC4R is associated with a dominant form of obesity, vol. 20(2), pp. 113-114, (1998).

Verma et al., *Pharmaceutical Technology On-line*, "Drug delivery technologies and future directions", vol. 25(2), 1-14, (2001).

Wikberg, et al., *Pharmacological Research*, "New Aspects on the Melanocortins and Their Receptors", vol. 42(5), pp. 393-420, (2000).

Yang, et al., *Molecular Endocrinology*, Characterization of Agouti-related protein binding to melanocortin receptors, vol. 13(1), pp. 148-155, (1999).

Yeo, et al., *Nature Genetics*, A frameshift mutation in MC4R associated with dominantly inherited human obesity, vol. 20, pp. 111-112, (Oct. 1998).

Benoit et al., *The Journal of Neuroscience*, A Novel Selective Melanocortin-4 Receptor Agonist Reduces Food Intake in Rats and Mice without Producing Aversive Consequences, vol. 20(9), pp. 3442-3448, 2000.

\* cited by examiner

DIAZEPINE AND DIAZOCANE COMPOUNDS AS MC4 AGONISTS

This application is a national stage filing of PCT/IB2009/053317 filed Jul. 30, 2009, which claims the benefit of Provisional Patent Application No. 61/086,530 filed Aug. 6, 2008.

FIELD OF THE INVENTION

The present invention relates to diazepane and diazocane compounds, pharmaceutical compositions comprising those compounds, and uses thereof in therapy. The foregoing compounds act as agonists at the melanocortin 4 (MC4 or MCR4) receptor.

BACKGROUND

Melanocortins are peptides derived from pro-opiomelanocortins (POMC) that bind to and activate G-protein coupled receptors (GPCR's) of the melanocortin receptor family. Melanocortins regulate a diverse number of physiological processes including sexual function and sexual behaviour, food intake and metabolism. There are five melanocortin receptors that have been cloned, MCR1, MCR2, MCR3, MCR4, MCR5, and are expressed in various tissues. MCR1 is specifically expressed in melanocytes and melanoma cells, MCR2 is the ACTH receptor and is expressed in adrenal tissue, MCR3 is predominantly expressed in the brain and limbic system, MCR4 is widely expressed in the brain and spinal cord, and MCR5 is expressed in the brain and many peripheral tissues including skin, adipose tissue, skeletal muscle, and lymphoid tissue. MCR3 may be involved in the control of sexual function, food intake and thermogenesis.

MCR4 is a G-protein-coupled seven-transmembrane receptor primarily expressed in the hypothalamus, hippocampus, and thalamus (Gantz et al. 1993 *J Biol Chem* 268:15174-15179). The receptor is implicated in the central regulation of body weight: MCR4 is activated by α-melanocyte-stimulating hormone (MSH), which is derived from pro-opiomelanocortin and is inactivated by agouti gene-related protein (AGRP). α-MSH induces weight loss, whereas the ectopic expression of agouti protein results in obesity in the agouti mice (Fan et al. 1993 *Nature* 385:165-168; Lu et al. 1994 *Nature* 371:799-802). Additional evidence for the role of MCR4 in weight regulation stems from both a knockout model in mice (Huszar et al. 1997 *Cell* 88:131-141) and haploinsufficiency mutations in humans (Vaisse et al. 1998 *Nat Genet* 20:113-114; Yeo et al. 1998 *Nat Genet* 20:111-112; Hinney et al. 1999 *J Clin Endocrinol Metab* 84:1483-1486). In MCR4-knockout mice, an increased body weight was discernible by age 5 wk. By age 15 wk, homozygous mutant females were, on average, twice as heavy as their wild-type littermates, whereas homozygous mutant males were ~50% heavier than wild-type controls. Mice heterozygous for the MCR4-knockout showed a weight gain intermediate to that seen in wild-type and homozygous mutant littermates, thus demonstrating a gene dosage effect of MCR4 ablation on body-weight regulation. The food intake of homozygous mutants was increased by ~50% in comparison to that in wild-type sibs (Huszar et al. 1997 *Cell* 88:131-141). [From *Am. J. Hum. Genet.*, 65:1501-1507, 1999]. MCR4 activation has been shown to induce penile erection in rodents and MCR4 inactivation has been shown to cause obesity (reviewed in Hadley, 1999, Ann N Y Acad. Sci., 885:1-21, Wikberg et al 2000, Pharmacol Res., 42(5), 393-420).

Chaki and Nakazato, in Drugs Of The Future, 2004, 29(10): 1065-1074, refer to potential therapeutic applications for ligands acting at the MC4 receptor. Diazepine derivatives are reported in WO 95/00497, WO 97/17973, WO 98/07692, WO 98/20001, WO 2006/040192 and EP 1867639. Inhibitors of FXa are reported in WO 98/54164. Compounds useful for treating bone deficit conditions are reported in WO 99/42107. Antagonists of H3 receptors are reported in WO 02/072570. Modulators of PPAR are reported in US 2005/0234046.

The compounds of the present invention are useful in treating diseases, disorders or conditions responsive to activation of the MC4 receptor, including:
 male and female sexual dysfunctions including hypoactive sexual desire disorder, sexual arousal disorder, orgasmic disorder and/or sexual pain disorder in females, male erectile dysfunction;
 obesity (by reducing appetite, increasing metabolic rate, reducing fat intake or reducing carbohydrate craving); and
 diabetes mellitus (by enhancing glucose tolerance and/or decreasing insulin resistance).

The compounds of the invention are potentially useful in treating further diseases, disorders or conditions including, but not limited to, hypertension, hyperlipidemia, osteoarthritis, cancer, gall bladder disease, sleep apnea, depression, anxiety, compulsion, neuroses, insomnia/sleep disorder, substance abuse, pain, fever, inflammation, immune modulation, rheumatoid arthritis, skin tanning, acne and other skin disorders, neuroprotective and cognitive and memory enhancement including the treatment of Alzheimer's disease, treatment of Lower Urinary Tract Dysfunction (including Urinary Incontinence—overactive bladder, increased daytime frequency, nocturia, urgency, urinary incontinence (any condition in which there is an involuntary leakage of urine), including stress urinary incontinence, urge urinary incontinence and mixed urinary incontinence, overactive bladder with associated urinary incontinence, enuresis, nocturnal enuresis, continuous urinary incontinence, situational urinary incontinence such as incontinence during sexual intercourse, and lower urinary tract symptoms (LUTS) associated with benign prostatic hyperplasia (BPH)), and any other indications mentioned in the above-referenced patent applications.

The compounds of the present invention are particularly suitable for treating female sexual dysfunction, male erectile dysfunction, obesity, diabetes, and conditions of Lower Urinary Tract Dysfunction.

The terms "treating", "treat", or "treatment" as used herein are intended to embrace both prevention and control i.e., prophylactic, and palliative treatment of the indicated conditions.

Desirable properties for MCR4 agonist compounds of the present invention include: desirable MCR4 agonist potencies as detailed hereinafter; selectivity for MCR4 agonism versus MCR1, and/or MCR5, and/or MCR3 as detailed hereinafter; both desirable MC4R agonist potency and selectivity for MCR4 versus, MCR1, and/or MCR5, and/or MCR3; good biopharmaceutical properties such as physical stability; solubility; oral bioavailability; appropriate metabolic stability.

SUMMARY

According to one embodiment, the present invention relates to compounds of formula (I):

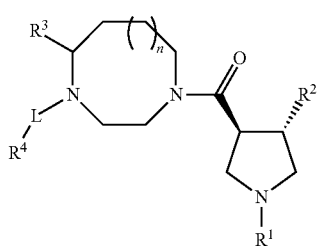

wherein n, $R^1$, $R^2$, $R^3$, L and $R^4$ are as defined hereinbelow in the detailed description.

Another embodiment of the present invention relates to a pharmaceutical composition comprising a compound of formula (I). In one aspect, the composition comprises a therapeutically effective amount of a compound of formula (I). In another aspect, the composition may also comprise one or more additional pharmaceutical agents (e.g., those described hereinbelow).

Yet another embodiment of the present invention relates to a method for treating disorders (including diseases and/or conditions) which would benefit from MC4 agonism comprising administering to a subject in need of such treatment a therapeutically effective amount of a compound of formula (I) (or a pharmaceutical composition thereof). In one aspect, the disorder is female sexual dysfunction (FSD), male erectile dysfunction (MED), or obesity.

DETAILED DESCRIPTION

The present invention relates to a compound of formula (I)

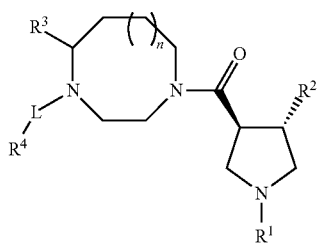

or pharmaceutically acceptable salts, solvates (including hydrates), and prodrugs thereof, wherein
n is 0 or 1;
$R^1$ is —$(C_1-C_4)$alkyl, or $Het^1$;
$R^2$ is phenyl or pyridyl, wherein said phenyl or pyridyl is optionally substituted by one to three substituents independently selected from halo, CN, —$(C_1-C_4)$alkyl and —$(C_1-C_4)$alkoxy wherein the —$(C_1-C_4)$alkyl and —$(C_1-C_4)$alkoxy groups are optionally substituted with 1 to 3 fluorine atoms;
$R^3$ is phenyl or pyridyl, wherein said phenyl or pyridyl is optionally substituted by one to three substituents independently selected from halo, CN, —$(C_1-C_4)$alkyl and —$(C_1-C_4)$alkoxy wherein the —$(C_1-C_4)$alkyl and —$(C_1-C_4)$alkoxy groups are optionally substituted with 1 to 3 fluorine atoms;

either L is —CO— and $R^4$ is —$(C_1-C_4)$alkyl, —$(C_1-C_4)$alkoxy, —$(C_3-C_6)$cycloalkyl, —$(C_1-C_2)$alkyl$(C_3-C_6)$cycloalkyl, —$(C_1-C_2)$alkyl$(C_1-C_4)$alkoxy, —$NH_2$, —$NH(C_1-C_4)$alkyl, —$N[(C_1-C_4)$alkyl$]_2$ or $Het^2$, wherein the —$(C_1-C_4)$alkyl group is optionally substituted with 1 to 3 fluorine atoms and wherein the —$(C_3-C_6)$cycloalkyl group is optionally substituted with 1 to 3 fluorine atoms or —$(C_1-C_4)$alkyl groups;
or L is —$SO_2$— and $R^4$ is —$(C_1-C_4)$alkyl; —$(C_3-C_6)$cycloalkyl, —$(C_1-C_2)$alkyl$(C_3-C_6)$cycloalkyl, —$(C_1-C_2)$alkyl$(C_1-C_4)$alkoxy, —$NH_2$, —$NH(C_1-C_4)$alkyl, —$N[(C_1-C_4)$alkyl$]_2$, or $Het^2$;
$Het^1$ is
(i) a 6-membered ring containing one or 2 N atoms, wherein the ring is either aromatic, or contains 2 double bonds in the ring and a =O substituent, which ring is optionally substituted by one to three substituents independently selected from halo, CN, and —$(C_1-C_4)$alkyl;
(ii) a 6-membered aromatic ring containing one or 2 N atoms fused at the 3,4-positions, relative to the attachment to the pyrrolidine ring, to a 5-membered aromatic ring containing one to three further N atoms; or
(iii) tetrahydropyranyl;
$Het^2$ is
(i) a 5-membered aromatic ring containing one or 2 N atoms and a further optional O atom, S atom or N atom,
(ii) a 4- to 6-membered saturated ring containing one N atom; or
(iii) a 6-membered saturated ring containing one O atom and a further optional N atom.

The term "alkyl" refers to a straight-chain or branched-chain saturated aliphatic hydrocarbon radical containing the specified number of carbon atoms. Examples of alkyl radicals include methyl, ethyl, n-propyl, isopropyl, n-butyl, isobutyl, sec-butyl, tert-butyl.

The term "alkoxy" refers to a radical OR where R is an alkyl as defined above.

The term "halo" refers to fluorine, chlorine, bromine or iodine.

The term "cycloalkyl" refers to a monocyclic aliphatic alkyl group containing the specified number of carbon atoms. Examples of cycloalkyl radicals include cyclopropyl, cyclobutyl, cyclopentyl and cyclohexyl.

Examples of "6-membered rings containing one or 2 N atoms, wherein the ring is either aromatic, or contains 2 double bonds in the ring and a =O substituent" include pyrazole, pyridine, pyrazine, pyrimidine, pyridazine and pyridazinone.

Examples of "6-membered aromatic rings containing one or 2 N atoms fused at the 3,4-positions, relative to the attachment to the pyrrolidine ring, to a 5-membered aromatic ring containing one to three further N atoms" include imidazo[1,2-b]pyridazine and [1,2,4]triazolo[4,3-b]pyridazine.

Examples of "5-membered aromatic rings containing one or 2 N atoms and a further optional O atom, S atom or N atom" include pyrrole, pyrazole, imidazole, oxazole, isoxazole, thiazole, isothiazole, triazole, oxadiazole and thiadiazole.

Examples of "4- to 6-membered saturated rings containing one N atom" include azetidine, pyrrolidine, piperidine and piperazine.

Examples of "6-membered saturated rings containing one O atom and a further optional N atom" include tetrahydropyran and morpholine.

In one embodiment, n is 1.
In one embodiment, $R^1$ is —$(C_1-C_4)$alkyl. In a further embodiment, $R^1$ is t-butyl.
In one embodiment, $R^1$ is $Het^1$ where $Het^1$ is (i) a 6-membered ring containing one or 2 N atoms, wherein the ring is either aromatic, or contains 2 double bonds in the ring and a =O substituent, which ring is optionally substituted by a substituent selected from halo, CN, and —($C_1$-$C_4$)alkyl; or (ii) a 6-membered aromatic ring containing one or 2 N atoms fused at the 3,4-positions, relative to the attachment to the pyrrolidine ring, to a 5-membered aromatic ring containing one or two further N atoms.

In a further embodiment, $R^1$ is $Het^1$ where $Het^1$ is pyridin-2-yl, pyridin-3-yl, pyridazin-3-yl, 6-oxo-1,6-dihydropyridazin-3-yl, 6-oxo-1,6-dihydropyridin-3-yl, 2-oxo-1,2-dihydropyrimidin-4-yl, 6-oxo-1,6-dihydropyrimidin-4-yl, 2-oxo-1,2-dihydropyridin-4-yl, [1,2,4]triazolo[4,3-b]pyridazin-6-yl or 6-oxo-1,6-dihydropyridin-2-yl, optionally substituted by one or two substituents independently selected from —($C_1$-$C_4$)alkyl, halo and CN.

In yet a further embodiment, $R^1$ is $Het^1$ where $Het^1$ is 6-oxo-1,6-dihydropyridazin-3-yl, 1-methyl-6-oxo-1,6-dihydropyridazin-3-yl, or [1,2,4]triazolo[4,3-b]pyridazin-6-yl.

In one embodiment, $R^2$ is phenyl or pyridyl, wherein said phenyl or pyridyl is optionally substituted by one or two substituents independently selected from halo, CN, —($C_1$-$C_4$)alkyl and —($C_1$-$C_4$)alkoxy. In a further embodiment, $R^2$ is 2,4-difluorophenyl, 2-fluoro-4-methoxyphenyl, 4-cyanophenyl or 5-chloropyrid-2-yl. In one embodiment, $R^3$ is phenyl optionally substituted by one or two substituents independently selected from halo and ($C_1$-$C_4$)alkoxy. In a further embodiment, $R^3$ is 4-chlorophenyl.

In one embodiment, L is —CO— and $R^4$ is —($C_1$-$C_4$)alkyl optionally substituted with 1 to 3 fluorine atoms, —($C_1$-$C_4$)alkoxy, —($C_3$-$C_6$)cycloalkyl optionally substituted with 1 or 2 fluorine atoms or —($C_1$-$C_4$)alkyl groups, —($C_1$-$C_2$)alkyl ($C_3$-$C_6$)cycloalkyl, —($C_1$-$C_2$)alkyl($C_1$-$C_4$)alkoxy, —NH ($C_1$-$C_4$)alkyl, —N[($C_1$-$C_4$)alkyl]$_2$ or $Het^2$ wherein $Het^2$ is a 5-membered aromatic ring containing 2 N atoms or a 6-membered saturated ring containing one O atom and a further optional N atom. In a further embodiment, L is —CO— and $R^4$ is —($C_1$-$C_4$)alkyl or —($C_1$-$C_4$)alkoxy wherein the —($C_1$-$C_4$)alkyl group is optionally substituted with 1 to 3 fluorine atoms.

It is to be understood that the invention covers all combinations of particular embodiments of the invention as described hereinabove, consistent with the definition of the compounds of formula (I).

Representative compounds of the invention include:
6-[(3S,4R)-3-{[5S-(4-chlorophenyl)-4-(3,3,3-trifluoropropanoyl)-1,4-diazocan-1-yl]carbonyl}-4-(2-fluoro-4-methoxyphenyl)pyrrolidin-1-yl]-2-methylpyridazin-3 (2H)-one;
6-[(3S,4R)-3-{[5S-(4-chlorophenyl)-4-isobutyryl-1,4-diazocan-1-yl]carbonyl}-4-(2,4-difluorophenyl)pyrrolidin-1-yl]-2-methylpyridazin-3(2H)-one;
6-[(3S,4S)-3-{[5S-(4-chlorophenyl)-4-isobutyryl-1,4-diazocan-1-yl]carbonyl}-4-(5-chloropyridin-2-yl)pyrrolidin-1-yl]-2-methylpyridazin-3(2H)-one;
methyl 8-(4-chlorophenyl)-4-{[(3S,4R)-4-(2-fluoro-4-methoxyphenyl)-1-(6-oxo-1,6-dihydropyridazin-3-yl)pyrrolidin-3-yl]carbonyl}-1,4-diazocane-1-carboxylate;
methyl 8S-(4-chlorophenyl)-4-{[(3S,4R)-4-(2-fluoro-4-methoxyphenyl)-1-(6-oxo-1,6-dihydropyridazin-3-yl) pyrrolidin-3-yl]carbonyl}-1,4-diazocane-1-carboxylate;
methyl 8R-(4-chlorophenyl)-4-{[(3S,4R)-4-(2-fluoro-4-methoxyphenyl)-1-(6-oxo-1,6-dihydropyridazin-3-yl) pyrrolidin-3-yl]carbonyl}-1,4-diazocane-1-carboxylate;
methyl 8R-(4-chlorophenyl)-4-{[(3S,4R)-4-(2-fluoro-4-methoxyphenyl)-1-(1-methyl-6-oxo-1,6-dihydropyridazin-3-yl)pyrrolidin-3-yl]carbonyl}-1,4-diazocane-1-carboxylate;
6-[(3S,4R)-3-{[4-acetyl-5S-(4-chlorophenyl)-1,4-diazocan-1-yl]carbonyl}-4-(2-fluoro-4-methoxyphenyl)pyrrolidin-1-yl]pyridazin-3(2H)-one;
methyl 8S-(4-chlorophenyl)-4-{[(3S,4S)-4-(5-chloropyridin-2-yl)-1-(6-cyanopyridazin-3-yl)pyrrolidin-3-yl]carbonyl}-1,4-diazocane-1-carboxylate;
1-{[(3S,4S)-1-tert-butyl-4-(5-chloropyridin-2-yl)pyrrolidin-3-yl]carbonyl}-5S-(4-chlorophenyl)-4-isobutyryl-1,4-diazocane;
6-[(3S,4S)-3-{[4-acetyl-5S-(4-chlorophenyl)-1,4-diazocan-1-yl]carbonyl}-4-(5-chloropyridin-2-yl)pyrrolidin-1-yl] [1,2,4]triazolo[4,3-b]pyridazine;
methyl 8S-(4-chlorophenyl)-4-{[(3S,4R)-4-(2,4-difluorophenyl)-1-(1-methyl-6-oxo-1,6-dihydropyridazin-3-yl) pyrrolidin-3-yl]carbonyl}-1,4-diazocane-1-carboxylate;
or pharmaceutically acceptable salts, solvates (including hydrates), and prodrugs thereof.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002), incorporated herein by reference.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('Melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970), incorporated herein by reference.

Hereinafter all references to compounds of formula (I) include references to salts, solvates, multi-component complexes and liquid crystals thereof and to solvates, multi-component complexes and liquid crystals of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'prodrugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association), incorporated herein by reference.

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985), incorporated herein by reference.

Moreover, certain compounds of formula (I) may themselves act as prodrugs of other compounds of formula (I).

The compounds of formula (I) may have asymmetric carbon atoms. The bonds from an asymmetric carbon in compounds of the present invention may be depicted herein using a solid line (———), a solid wedge (———), or a dotted wedge (‧‧‧‧‧‧‧). The use of a solid line to depict bonds from asymmetric carbon atoms is meant to indicate that all possible stereoisomers at that carbon atom are included. The use of either a solid or dotted wedge to depict bonds from asymmetric carbon atoms is meant to indicate that only the stereoisomer shown is meant to be included. It is possible that compounds of formula (I) may contain more than one asymmetric carbon atom. In those compounds, the use of a solid line to depict bonds from asymmetric carbon atoms is meant to indicate that all possible stereoisomers are meant to be included. Where a compound of formula (I) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism. As an example to illustrate a tautomeric relationship, the compound where for example the "Het$^1$" group is as shown below, both "keto" and "enol" tautomers below are included within the scope of "Het$^1$" for the compounds of formula (I):

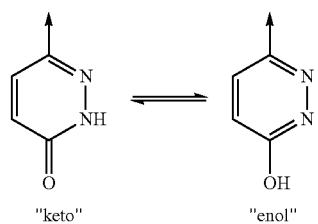

"keto"       "enol"

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer (s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2 to 20%, and may contain from 0 to 5% by volume of an alkylamine. Concentration of the eluate affords the enriched mixture. The absolute composition of the mobile phase will be dependent upon the chiral stationary phase (asymmetric resin) selected.

Stereoisomeric conglomerates may be separated by conventional techniques known to those skilled in the art—see, for example, *Stereochemistry of Organic Compounds* by E. L. Eliel and S. H. Wilen (Wiley, New York, 1994), incorporated herein by reference.

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

The routes below, including those mentioned in the Examples and Preparations, illustrate methods of synthesising compounds of formula (I). The skilled person will appreciate that the compounds of the invention, and intermediates thereto, could be made by methods other than those specifically described herein, for example by adaptation of the methods described herein, for example by methods known in the art. Suitable guides to synthesis, functional group interconversions, use of protecting groups, etc., are for example: "Comprehensive Organic Transformations" by R C Larock, VCH Publishers Inc. (1989); Advanced Organic Chemistry" by J. March, Wiley Interscience (1985); "Designing Organic Synthesis" by S Warren, Wiley Interscience (1978); "Organic Synthesis—The Disconnection Approach" by S Warren, Wiley Interscience (1982); "Guidebook to Organic Synthesis" by R K Mackie and DM Smith, Longman (1982); "Protective Groups in Organic Synthesis" by T W Greene and P G M Wuts, John Wiley and Sons, Inc. (1999); and "Protecting Groups" by P J, Kocienski, Georg Thieme Verlag (1994).

In the general synthetic methods below, unless otherwise specified, the substituents $R^1$, $R^2$, $R^3$, $R^4$ and L are as defined above with reference to the compounds of formula (I) above.

Scheme 1 illustrates the preparation of compounds of formula (I) via acylation of intermediates (II) with acylating agents (III).

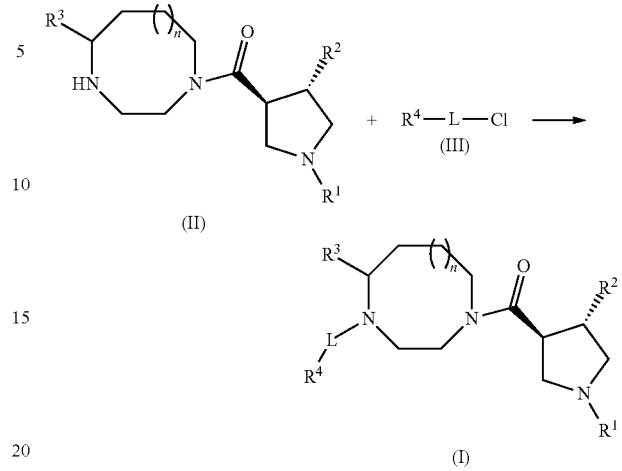

Scheme 1

Typical conditions involve stirring a solution of the diazepane or diazocane of general formula (II) and the acylating agent of general formula (III) with a base in an appropriate solvent at room temperature. Suitable acylating agents (III) include carboxylic acid chlorides, sulphonyl chlorides, carbamoyl chlorides and chloroformates and are commercially available or will be well-known to those skilled in the art with reference to literature precedents; suitable bases include pyridine, triethylamine, diisopropylethylamine, N-methylmorpholine or dimethylaminopyridine; suitable solvents include dichloromethane (DCM), dimethylformamide (DMF), tetrahydrofuran (THF) or ethyl acetate (EtOAc).

Scheme 2 illustrates an alternative preparation of certain compounds of general formula (I) where L is carbonyl from diazepane and diazocane intermediates (II) using peptide coupling reagents (IV).

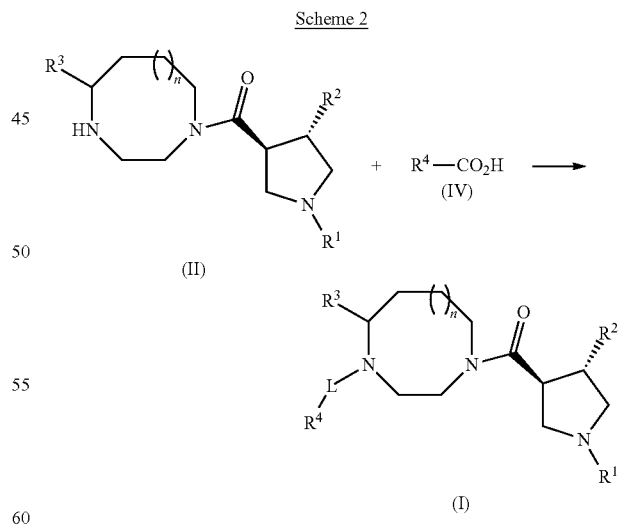

Scheme 2

Typical conditions involve stirring a solution of the diazepane or diazocane of general formula (II) and a carboxylic acid of general formula (IV) together with 1-(3-dimethylaminopropyl)-3-ethyl-carbodiimide hydrochloride (EDCl) or its methiodide salt, plus triethylamine and 1-hydroxybenzotriazole hydrate (HOBt) in dichloromethane (DCM). Carboxylic acids of general formula (IV) are commercially available or will be well-known to those skilled in the art with reference to literature precedents. A further alternative suitable procedure is to stir a solution of the intermediate compounds of general formula (II) and the acid of general formula (IV) in an inert solvent together with suitable peptide coupling reagents, if necessary adding a suitable base and/or additive. Suitable peptide coupling reagents include O-benzotriazol-1-yl-N,N,N',N' tetramethyluronium hexafluorophosphate (HBTU), 2-{1H-benzotriazol-1-yl}-1,1,1,3-tetramethyluronium tetrafluoroborate (TBTU), O-(7-azabenzotriazol-1-yl)-N,N,N',N'-tetramethyluronium hexafluorophosphate (HATU), 2-chloro-1,3-dimethylimidazolinium chloride (DIC), 1-propylphosphonic acid cyclic anhydride (T3P) or the polymer-supported Mukaiyama reagent; and suitable bases include pyridine, triethylamine, diisopropylethylamine, N-methylmorpholine or dimethylaminopyridine. Any suitable inert solvent may be used in place of that mentioned above, wherein inert solvent means a solvent which does not contain a carboxylic acid or primary or secondary amine. At least one equivalent of each of the coupling reagents should be used and an excess of either one or both may be used if desired.

Scheme 3 illustrates an alternative route for the preparation of compounds of general formula (I) from functionalised diazepanes and diazocanes of general formula (V) and pyrrolidine acids of general formula (VI) using peptide coupling reagents as described in scheme 2.

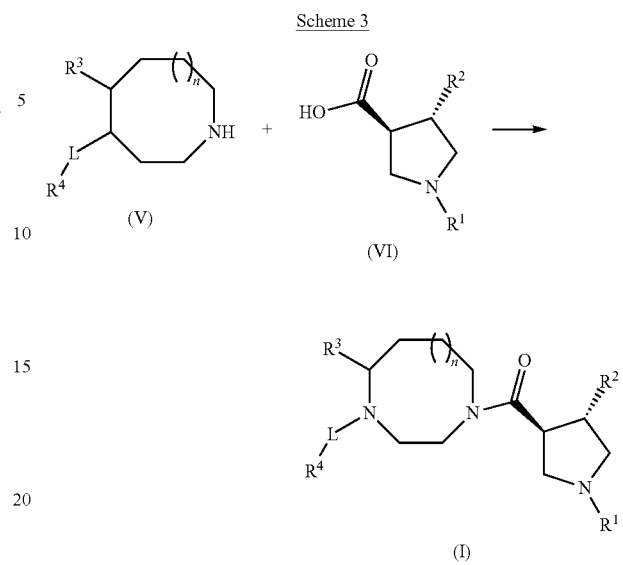

Scheme 3

Scheme 4 illustrates further alternative routes for the preparation of compounds of general formula (I) where $R^1$ is $Het^1$, via a protecting group strategy.

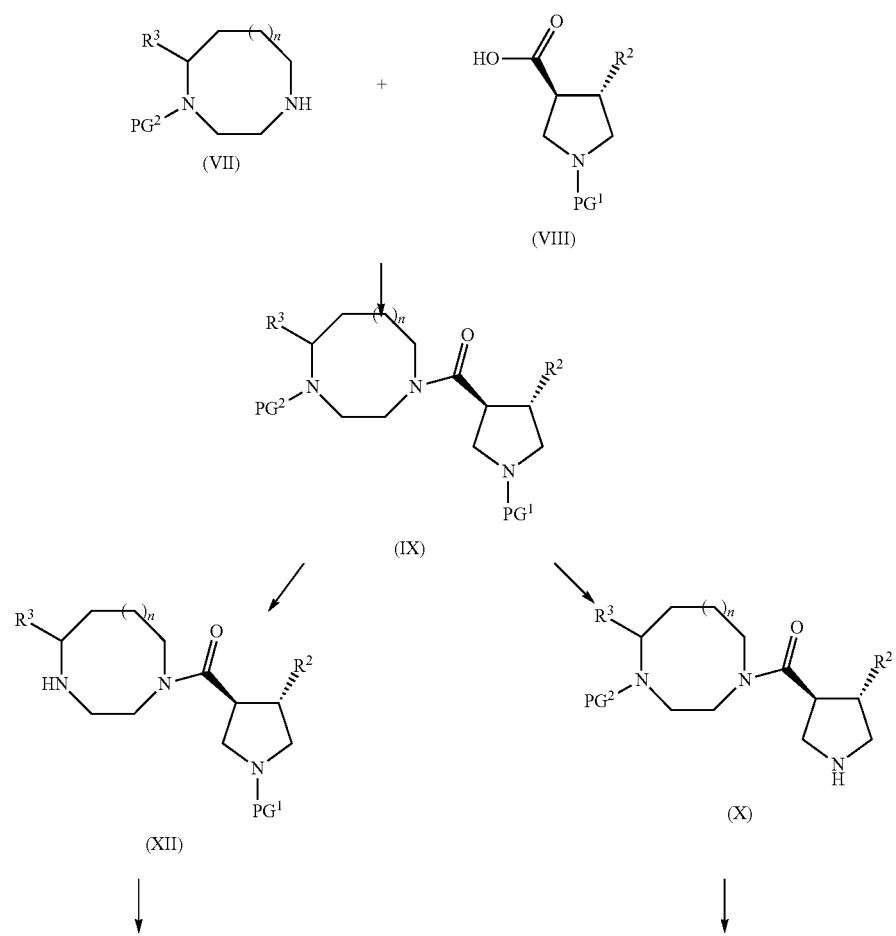

Scheme 4

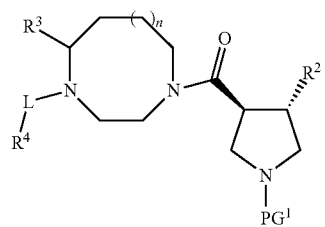

(XIII)

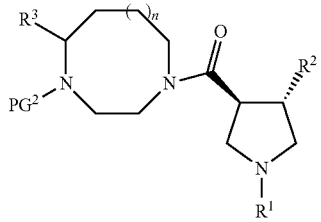

(XI)

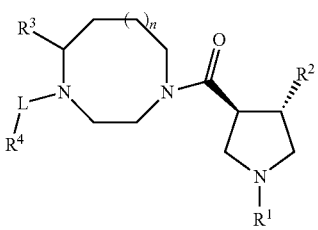

(I)

PG¹ is a suitable nitrogen-protecting group.
PG² is either LR⁴ or another nitrogen-protecting group, orthogonal to PG¹.

In scheme 4 the diazepane and diazocane intermediates of general formula (VII) and protected pyrrolidine acid intermediates of general formula (VIII) are coupled using standard peptide coupling methods as previously described in schemes 2 and 3 to provide coupled intermediates of general formula (IX) containing orthogonal protection. The nitrogen protecting groups PG¹ and PG² can be removed differentially using standard de-protection strategies to furnish either intermediates of general formula (X) (through de-protection of PG¹) or intermediates of general formula (XII) (through de-protection of PG²). Any suitable nitrogen protecting groups may be used (as described in "Protecting Groups in Organic Synthesis" 3$^{rd}$ Edition T. W. Greene and P. G. Wuts, Wiley-Interscience, 1999). Common nitrogen protecting groups (PG) suitable for use herein include tert-butoxycarbonyl (t-Boc), which is readily removed by treatment with an acid such as trifluoroacetic acid or hydrogen chloride in an organic solvent such as dichloromethane or 1,4-dioxane; benzyl, which is readily removed by hydrogenation in the presence of a suitable catalyst or by treatment with 1-chloroethyl chloroformate (ACE-Cl) followed by methanolysis; or t-butyl which is also readily removed by ACE-Cl and methanolysis.

The R¹ group (where R¹=Het¹ as mentioned above) may be introduced by displacement of a suitable leaving group ("hetylation"), for example from a heteroaromatic precursor of formula "Het¹-Z" where Z is a suitable leaving group. Suitable leaving groups include halogens. In certain cases transition metal catalysis (e.g. palladium, copper), optionally in combination with a phosphine ligand such as 1,1'-binaphthalene-2,2'-diylbisdiphenylphosphine, may be required to achieve the required coupling products.

According to scheme 4, intermediates of general formula (X) can be "hetylated" to give intermediates of general formula (XI) that can be further elaborated to compounds of general formula (I) through de-protection of PG² then capping of the exposed NH function with R⁴L following the methods described in schemes 1 and 2. Alternatively, intermediates of general formula (XII) may be capped with R⁴L following the methods described in schemes 1 and 2, then elaborated to compounds of general formula (I) through de-protection of PG¹ and subsequent "hetylation" as described above.

Alternatively, compounds of general formula (I) where R¹ is a given Het¹ group may be converted into other compounds of general formula (I) where R¹ is a different Het¹ group. For example:

i) Compounds of formula (Ia), where Het¹ contains a suitable leaving group Z, such as chloro or methoxy, can be converted into compounds of formula (Ib), as shown in scheme 5, by hydrolysis under either acidic or basic conditions. Acidic conditions are preferred, and particularly preferred is treatment of compounds of formula (Ia) with acetic acid at reflux temperature. Alternatively, a compound of formula (Ia), where Z is chloro, can be reacted with an alkoxide of formula Y—O⁻, to give an intermediate of formula (Ia), where Z is OY. Subsequent hydrolysis then provides the compounds of formula (Ib). Suitable groups Y could include methyl or benzyl.

Scheme 5

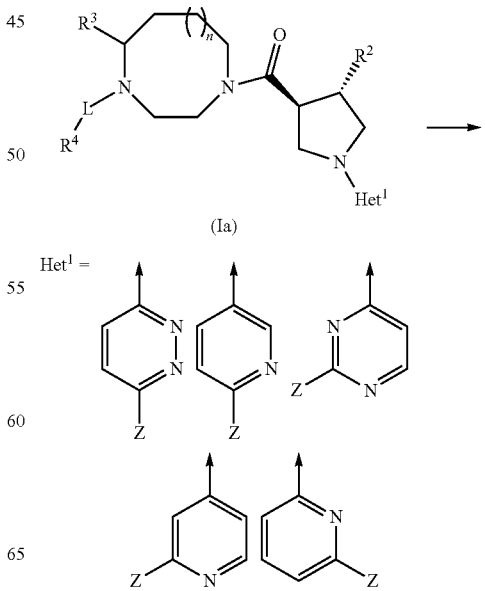

-continued

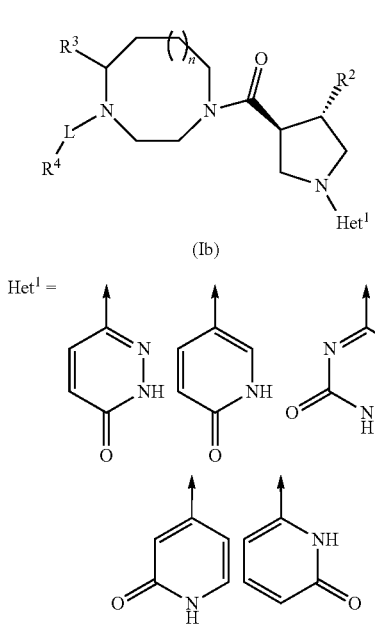

(Ib)

Het¹ =

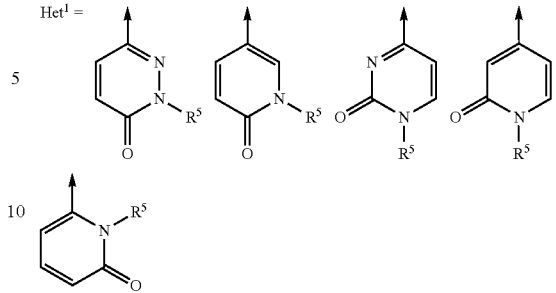

ii) Compounds of formula (Ic), where Het¹ is as shown in scheme 6 and R⁵ is H, can be converted into compounds of formula (Id), where R⁵ is alkyl, by treatment with a base and an alkylating agent in an appropriate solvent. Suitable bases include sodium hydride, lithium diisopropylamide and sodium hexamethyldisilazide; suitable alkylating agents include methyl iodide, methyl tosylate, dimethyl sulfate and ethyl iodide; and suitable solvents include tetrahydrofuran, dimethylformamide and N-methyl-2-pyrrolidinone. An optional additive, such as a lithium salt (lithium bromide for example) may also be present in the reaction mixture.

Scheme 6

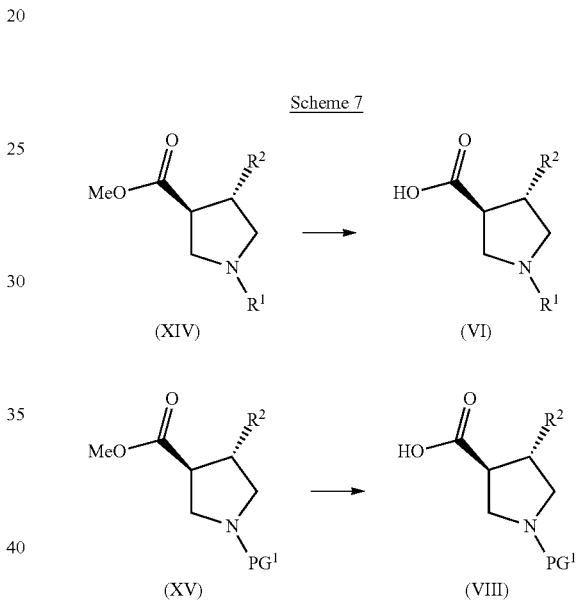

Pyrrolidine acids of general formulae (VI) and (VIII) can be prepared by de-esterification of precursor esters of general formulae (XIV) and (XV) respectively using a variety of known literature methods as shown in scheme 7.

Scheme 7

A preferred method involves basic hydrolysis of esters of general formulae (XIV) and (XV) using an aqueous solution of a suitable metal hydroxide in a suitable co-solvent. Suitable metal hydroxides include those derived from alkali metals (for example Li, Na or K) or alkaline earth metals (for example Ca or Ba) and suitable co-solvents include water-miscible organic solvents such as THF, dioxan and hydroxylic solvents (for example methanol and ethanol). Another preferred method for de-esterification of esters of general formulae (XIV) and (XV) is by treatment with potassium trimethylsilanolate in a suitable solvent such as acetonitrile or toluene.

Scheme 8 illustrates a route for preparation of novel pyrrolidine ester intermediates of general formula (XV) from trans cinnamate derivatives (XVI).

Scheme 8

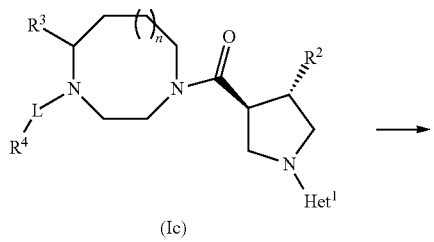

(XVI)

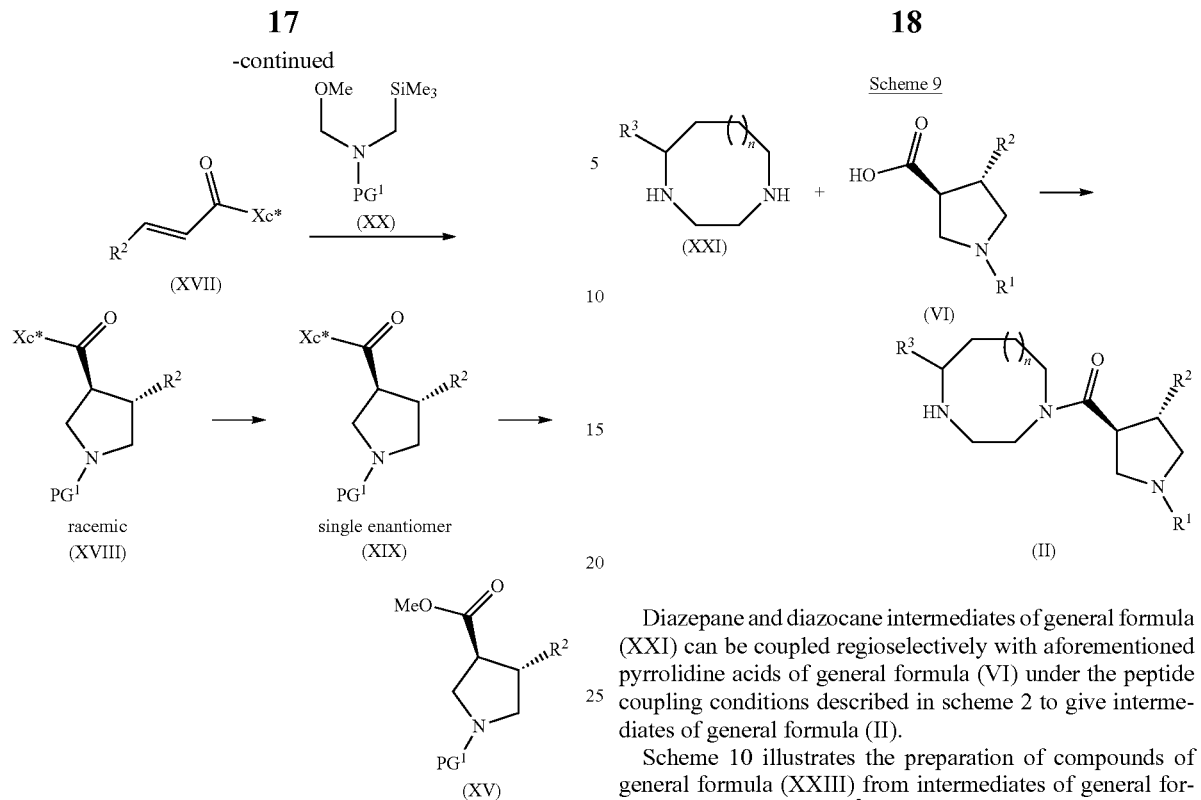

PG¹ is a suitable protecting group such as tert-butyl or benzyl.
Xc* is a chiral auxiliary.

Cinnamic acids (XVI) are either commercially available or will be well-known to those skilled in the art with reference to literature precedents. Cinnamic acids (XVI) can be coupled with a variety of chiral auxiliaries (Xc*) known in the literature using standard peptide coupling reagents as described in scheme 2 to give homochiral cinnamate derivatives of general formula (XVII). Commercially available oxazolidinone chiral auxiliaries are preferred in this respect. Intermediates (XVII) undergo [3+2] cycloaddition with an azomethine ylid precursor of general formula (XX) to provide a racemic pyrrolidine of general formula (XVIII) with predominantly or exclusively trans stereochemistry. This reaction requires an inert solvent such as dichloromethane or toluene or tetrahydrofuran and activation by one or more of: (1) an acid catalyst, such as TFA; (2) a desilylating agent such as silver fluoride; (3) heating. Racemic compounds of general formula (XVIII) may be resolved by standard methods such as chromatography or fractional crystallisation to give homochiral intermediates of general formula (XIX). The chiral auxiliaries Xc* contained in intermediates of general formula (XIX) are cleaved using literature-precedented methods to give pyrrolidine esters of general formula (XV). In particular, oxazolidinone chiral auxiliaries may be de-protected with a Lewis acid such as samarium triflate in methanol.

Pyrrolidine esters of general formula (XIV) can be prepared from pyrollidine esters of general formula (XV) by the de-protection and "hetylation" strategy described in scheme 4.

Scheme 9 illustrates the preparation of intermediates of general formula (II) from diazepane and diazocane intermediates of general formula (XXI) through coupling with pyrrolidine acids of general formula (VI).

Diazepane and diazocane intermediates of general formula (XXI) can be coupled regioselectively with aforementioned pyrrolidine acids of general formula (VI) under the peptide coupling conditions described in scheme 2 to give intermediates of general formula (II).

Scheme 10 illustrates the preparation of compounds of general formula (XXIII) from intermediates of general formula (XXII) wherein PG³ is a nitrogen protecting group such as benzyl or t-butoxycarbonyl.

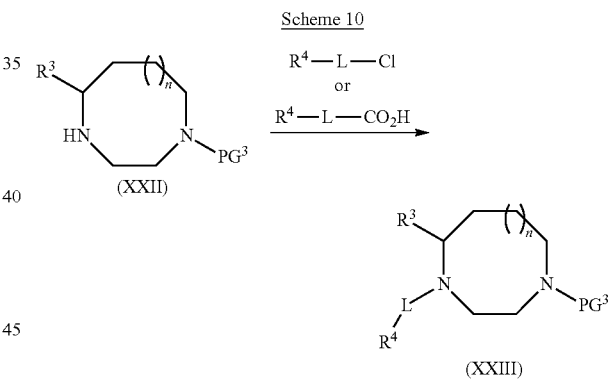

Compounds of general formula (XXIII) may be prepared through acylation (as described in scheme 1) or by using peptide coupling agents (as described in scheme 2). There are several methods available for the preparation of precursors of general formula (XXII) including, but not limited to, a regioselective mono-protection of compounds of general formula (XXI) as exemplified in Preparation 13 or a more direct assembly as exemplified in Preparation 2.

Intermediate compounds of formula (II), (V), (VI), (VII), (VIII), (IX), (XI), (XII), (XIII), (XIV), (XV), (XXI), (XXII) and (XXIII) as described above represent further embodiments of the invention.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2 to 20%, and may contain from 0 to 5% by volume of an alkylamine. Concentration of the eluate affords the enriched mixture. The absolute composition of the mobile phase will be dependant upon the chiral stationary phase (asymmetric resin) selected.

The skilled man will appreciate that, in addition to protecting nitrogen or acid groups, as discussed hereinbefore, at various times during the synthesis of the compounds of formula (I), it may be necessary to protect further groups, such as for example, hydroxy groups with a suitable protecting group, then remove the protecting group. Methods for deprotection of any particular group will depend on the protecting group. For examples of protection/deprotection methodology see "Protective groups in Organic synthesis", T W Greene and P G M Wutz, incorporated herein by reference. For example, where a hydroxy group is protected as a methyl ether, deprotection conditions could for example comprise refluxing in 48% aqueous HBr, or by stirring with borane tribromide in dichloromethane. Alternatively where a hydroxy group is protected as a benzyl ether, deprotection conditions could for example comprise hydrogenation with a palladium catalyst under a hydrogen atmosphere.

All of the above reactions and the preparations of novel starting materials used in the preceding methods are conventional and appropriate reaction conditions for their performance or preparation as well as procedures for isolating the desired products will be well-known to those skilled in the art with reference to literature precedents and the Examples and Preparations herein.

A pharmaceutically acceptable salt of a compound of the formula (I) may be readily prepared by mixing together solutions of a compound of the formula (I) and the desired acid as appropriate. The salt may precipitate from solution and be collected by filtration or may be recovered by evaporation of the solvent. Pharmaceutically acceptable salts of compounds of formula (I) may be prepared by one or more of three methods:

(i) by reacting the compound of formula (I) with the desired acid;
(ii) by removing an acid- or base-labile protecting group from a suitable precursor of the compound of formula (I) or by ring-opening a suitable cyclic precursor, for example, a lactone or lactam, using the desired acid; or
(iii) by converting one salt of the compound of formula (I) to another by reaction with an appropriate acid or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) of the present invention have utility as MCR4 agonists in the treatment of various disease states. Preferably said MCR4 agonists exhibit a functional potency at the MC4 receptor expressed as an $EC_{50}$, lower than about 400 nM, more preferably lower than 200 nM, yet more preferably lower than about 100 nM and more preferably still lower than about 50 nM wherein said $EC_{50}$ measurement of MCR4 functional potency can be carried out using Protocol E as described in International Patent Application WO 2005/077935.

Combination Therapy

The compounds of formula (I) or their salts, solvates or prodrugs, of the present invention may be usefully delivered in combination with one or more additional pharmaceutical agents for the treatment of conditions of interest, such as sexual dysfunction, lower urinary tract disorders, obesity and/or diabetes. Further, the compounds of formula (I) or their salts, solvates or prodrugs, of the present invention may in some cases be usefully delivered in combination with an auxiliary effective active agent for the reduction of emesis. Some suitable pharmaceutical agents which may be of use in combinations of the present invention include:

1) Compounds which modulate the action of natriuretic factors in particular atrial naturetic factor (also known as atrial naturetic peptide), B type and C type natriuretic factors such as inhibitors or neutral endopeptidase and in particular the compounds described and claimed in WO 02/02513, WO 02/03995, WO 02/079143 and EP-A-1258474, and especially the compound of Example 22 of WO 02/079143 (2S)-2{[1-{3-4(-chlorophenyl)propyl]amino}carbonyl)-cyclopentyl]methyl}-4-methoxybutanoic acid;
2) Compounds which inhibit angiotensin-converting enzyme such as enalapril, and combined inhibitors of angiotensin-converting enzyme and neutral endopeptidase such as omapatrilat;
3) Substrates for NO-synthase, such as L-arginine;
4) Cholesterol lowering agents such as statins (e.g. atorvastatin/Lipitor™) and fibrates (e.g. fenofibrate);
5) Estrogen receptor modulators and/or estrogen agonists and/or estrogen antagonists, preferably raloxifene or lasofoxifene ((-)-cis-6-phenyl-5-[4-(2-pyrrolidin-1-ylethoxy)-phenyl]-5,6,7,8-tetrahydronaphthalene-2-ol, and pharmaceutically acceptable salts thereof the preparation of which is detailed in WO 96/21656);
6) A PDE inhibitor, more particularly a PDE 2, 3, 4, 5, 7 or 8 inhibitor, preferably PDE2 or PDE5 inhibitor and most preferably a PDE5 inhibitor (see hereinafter), said inhibitors preferably having an IC50 against the respective enzyme of less than 100 nM (with the proviso that PDE 3 and 4 inhibitors are only administered topically or by injection to the penis for treatment of Male Erectile Dysfunction);
7) Vasoactive intestinal protein (VIP), VIP mimetic, VIP analogue, more particularly mediated by one or more of the VIP receptor subtypes VPAC1, VPAC or PACAP (pituitory adenylate cyclase activating peptide), one or more of a VIP receptor agonist or a VIP analogue (e.g. Ro-125-1553) or a VIP fragment, one or more of a α-adrenoceptor antagonist with VIP combination (e.g. Invicorp, Aviptadil);
8) A serotonin receptor agonist, antagonist or modulator, more particularly agonists, antagonists or modulators for 5HT1A (including VML 670 [WO02/074288] and flibanserin [US2003/0104980]), 5HT2A, 5HT2C, 5HT3 and/or 5HT6 receptors, including those described in WO-09902159, WO-00002550 and/or WO-00028993;
9) A testosterone replacement agent (including dehydroandrostendione), testosterone (e.g. Tostrelle™, LibiGel™), dihydrotestosterone or a testosterone implant;
10) Selective androgen receptor modulators e.g. LGD-2226;
11) Estrogen, estrogen and medroxyprogesterone or medroxyprogesterone acetate (MPA) (i.e. as a combination), or estrogen and methyl testosterone hormone replacement therapy agent (e.g. HRT especially Premarin, Cenestin, Oestrofeminal, Equin, Estrace, Estrofem, Elleste Solo, Estring, Eastraderm TTS, Eastraderm Matrix, Dermestril, Premphase, Preempro, Prempak, Premique, Estratest, Estratest HS, Tibolone);
12) A modulator of transporters for noradrenaline, dopamine and/or serotonin, such as bupropion, GW-320659;
13) An agonist or modulator for oxytocin/vasopressin receptors, preferably a selective oxytocin agonist or modulator;
14) An agonist or modulator for dopamine receptors, preferably a D3 or D4 selective agonist or modulator e.g. apomorphine; and 15) An antiemetic agent, for example a 5-HT$_3$ antagonist or a neurokinin-1 (NK-1) antagonist.

Suitable 5-HT$_3$ antagonists include, but are not limited to, granisetron, ondansetron, tropisetron, ramosetron, palonsetron, indisetron, dolasetron, alosetron and azasetron.

Suitable NK-1 antagonists include, but are not limited to, aprepitant, casopitant, ezlopitant, cilapitant, netupitant, vestipitant, vofopitant and 2-(R)-(1-(R)-3,5-bis(trifluoromethyl)phenyl)ethoxy-4-(5-(dimethylamino)methyl-1,2,3-triazol-4-yl)methyl-3-(S)-(4-fluorophenyl)morpholine. See for example International Patent Application publication number WO2006/049933.

With particular reference to the use of the compounds of the invention for the treatment of lower urinary tract dysfunction, combinations with other agents may include but are not limited to Muscarinic acetylcholine receptor antagonist such as tolterodine;

Alpha adrenergic receptor antagonist, in particular an alpha1 adrenergic receptor antagonist or an alpha2 adrenergic receptor antagonist;

Alpha adrenergic receptor agonist or partial agonist, in particular an alpha1 adrenergic receptor agonist or partial agonist, or an alpha2 adrenergic receptor agonist or partial agonist;

5HT2C agonist (see WO 2004/096196);

Serotonin and Noradrenalin reuptake inhibitor (SNRI);

Noradrenalin reuptake inhibitor (NRI) such as reboxetine, either in its racemic or (S,S)-enantiomeric form;

Vanilloid receptor (VR) antagonist, such as capsaicin;

alpha2delta ligand, such as gabapentin or pregabalin;

Beta3 adrenergic receptor agonist;

5HT1a receptor antagonist or 5HT1a receptor inverse agonist;

Prostanoid receptor antagonist, e.g. EP1 receptor antagonist.

With regard to the use of the compounds of formula (I) in the treatment of obesity and related disorders, the compounds may also be useful in conjunction with other anti-obesity agents. Suitable anti-obesity agents include cannabinoid 1 (CB-1) receptor antagonists (such as rimonabant), apolipoprotein-B secretion/microsomal triglyceride transfer protein (apo-B/MTP) inhibitors (in particular, gut-selective MTP inhibitors, such as edipatapide or dirlotapide), 11β-hydroxy steroid dehydrogenase-1 (11β-HSD type 1) inhibitors, peptide YY$_{3-36}$ and analogs thereof, cholecystokinin-A (CCK-A) agonists, monoamine reuptake inhibitors (such as sibutramine), sympathomimetic agents, β$_3$ adrenergic receptor agonists, dopamine receptor agonists (such as bromocriptine), melanocyte-stimulating hormone receptor analogs, 5HT2c receptor agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), Neuropeptide-Y receptor antagonists (in particular, NPY-5 receptor antagonists), thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art. The compounds of the present invention may also be administered in combination with a naturally occurring compound that acts to lower plasma cholesterol levels. Such naturally occurring compounds are commonly called nutraceuticals and include, for example, garlic extract, *Hoodia* plant extracts, and niacin. Especially preferred are anti-obesity agents selected from the group consisting of CB-1 antagonists, gut-selective MTP inhibitors, orlistat, sibutramine, bromocriptine, ephedrine, leptin, peptide YY$_{3-36}$ and analogs thereof, and pseudoephedrine. Preferably, compounds of the present invention and combination therapies for the treatment of obesity and related conditions are administered in conjunction with exercise and a sensible diet. Preferred CB-1 antagonists include Rimonabant (SR141716A also known under the tradename Acomplia™ available from Sanofi-Synthelabo) described in U.S. Pat. No. 5,624,941; and compounds described in U.S. Pat. Nos. 5,747,524, 6,432,984 and 6,518,264; U.S. Patent Publication Nos. US2004/0092520, US2004/0157839, US2004/0214855, and US2004/0214838; U.S. patent application Ser. No. 10/971,599 filed on Oct. 22, 2004; and PCT Patent Publication Nos. WO 02/076949, WO 03/075660, WO04/048317, WO04/013120, and WO 04/012671. Preferred gut-selective MTP inhibitors include dirlotapide described in U.S. Pat. No. 6,720,351; 4-(4-(4-(4-((2-((4-methyl-4H-1,2,4-triazol-3-ylthio)methyl)-2-(4-chlorophenyl)-1,3-dioxolan-4-yl)methoxy)phenyl)piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,431. Other representative anti-obesity agents for use in the combinations, pharmaceutical compositions, and methods of the invention can be prepared using methods known to one of ordinary skill in the art, for example; sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540,917; and 5,643,874; and PYY$_{3-36}$ (including analogs) can be prepared as described in US Publication No. 2002/0141985 and WO 03/027637.

One preferred group herein are combinations of the compounds of the present invention and one or more additional therapeutic agents selected from: PDE5 inhibitors; NEP inhibitors; D3 or D4 selective agonists or modulators; estrogen receptor modulators and/or estrogen agonists and/or estrogen antagonists; testosterone replacement agents, testosterone or a testosterone implant; estrogen, estrogen and medroxyprogesterone or medroxyprogesterone acetate (MPA), or estrogen and methyl testosterone hormone replacement therapy agent.

Preferred combinations for the treatment of MED are combinations of the compounds of the present invention and one or more PDE5 inhibitors and/or NEP inhibitors.

Preferred combinations for the treatment of FSD are combinations of the compounds of the present invention and PDE5 inhibitors, and/or 5HT1a receptor antagonists, and/or NEP inhibitors, and/or D3 or D4 selective agonists or modulators, and/or estrogen receptor modulators, estrogen agonists, estrogen antagonists, and/or testosterone replacement agents, testosterone, testosterone implant, and/or estrogen, estrogen and medroxyprogesterone or medroxyprogesterone acetate (MPA), estrogen and methyl testosterone hormone replacement therapy agent.

Particularly preferred PDE5 inhibitors for such combined products for the treatment of MED or FSD are 5-[2-ethoxy-5-(4-methyl-1-piperazinylsulphonyl)phenyl]-1-methyl-3-n- propyl-1,6-dihydro-7H-pyrazolo[4,3-d]pyrimidin-7-one (sildenafil, particularly present as the citrate salt);

(6R,12aR)-2,3,6,7,12,12a-hexahydro-2-methyl-6-(3,4-methylenedioxyphenyl)-pyrazino[2',1':6,1]pyrido[3,4-b]indole-1,4-dione (IC-351 or tadalafil);

2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil);

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one;

5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one;

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one;

4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide (avanafil);

3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide (udenafil);

7-(3-Bromo-4-methoxy-benzyl)-1-ethyl-8-(2-hydroxy-cyclopentylamino)-3-(2-hydroxy-ethyl)-3,7-dihydro-purine-2,6-dione (dasantafil);

and pharmaceutically acceptable salts thereof.

Particularly preferred NEP inhibitors for such combined products for the treatment of MED or FSD are the compounds exemplified in WO 02/079143.

By cross reference herein to compounds contained in patents and patent applications which can be used in accordance with invention, we mean the therapeutically active compounds as defined in the claims (in particular of claim 1) and the specific examples (all of which is incorporated herein by reference).

If a combination of active agents is administered, then they may be administered simultaneously, separately or sequentially, in formulations which may be the same or different.

Biological Assays

Melanocortin Receptor Agonist Activity; Selectivity

Measurement of In Vitro Agonist Potency ($EC_{50}$) of Compounds Against Melanocortin Receptors Type 1 and 3 (MC1 and MC3).

Activation of melanocortin (MC) receptors by agonists results in activation of intracellular adenylate cyclase enzymes that synthesise the second messenger signalling molecule, adenosine 3',5'-cyclic monophosphate (cAMP). Changes in cAMP levels following treatment of recombinant MC1 and MC3 cell lines with test compound were measured and an MC1 and MC3 potency estimate ($EC_{50}$) calculated as follows:

Human embryonic kidney (HEK) or Chinese hamster ovary cell lines stably transfected with full length cDNA encoding human MC1 or MC3 receptors, respectively, were established using standard molecular biology methods. Test compounds were dissolved in dimethyl sulfoxide (DMSO) at 4 mM. 11 point half log unit increment dilution series of test compound, typically starting at 50 uM were prepared in a buffer comprised of phosphate buffered saline (PBS), 2.5% DMSO and 0.05% pluronic F-127 surfactant. Freshly cultured cells at 80-90% confluence were harvested and re-suspended in Dulbecco's Modified Eagle's Medium (DMEM). Cells (10,000 for MC3, 20,000 for MC1) were added to the test compound dilution series in a 384 well assay plate and incubated for 1 hour at 37° C. The relative cAMP concentration in each well was then measured using a β-ga-lactosidase enzyme fragment complementation method purchased in kit form as the Discoverx cAMP II kit from GE Healthcare/Amersham Biosciences UK. In the case of MC1, 3-Isobutyl-1-methylxanthine (IBMX) at a concentration of 750 μM was included in DMEM as the cells were re-suspended for assay. The fluorescence readings taken from each assay well were converted into percent effect relative to maximum control wells corresponding to a concentration of alpha melanocyte stimulating hormone demonstrated to give a maximal effect. Sigmoidal curves were fitted to plots of $\log_{10}$ inhibitor concentration vs percent effect using a custom made software application called SIGHTS and $EC_{50}$ estimates determined by the software as the concentration of test compound giving an effect half way between the bottom and top asymptotes of the sigmoidal dose response curve. Each experiment included an $EC_{50}$ determination for alpha melanocyte stimulating hormone, which was used as a standard to track assay consistency and allow fair comparison between $EC_{50}$ estimates obtained in different experiments.

MC5 and MC4 $EC_{50}$ activity was determined as described by assay protocols D and E, respectively, in US2005/0176772 (pages 28-30).

Nle4, D-Phe7-α-MSH Inhibition at the MC4 Receptor

Nle4, D-Phe7-α-MSH is a stable analogue of melanocyte-stimulating hormone (MSH), which is an agonist at the MC4 receptor (MC4R). Compounds can be evaluated for their ability to inhibit Nle4, D-Phe7-α-MSH binding to membranes from cells expressing the MC4R using a competition binding assay versus [$^{125}$I] Nle4, D-Phe7-α-MSH.

Cells expressing the MC4R were subject to homogenisation and the membrane fragment isolated by differential centrifugation. CHO-CRE MC4R cell membranes were coupled to PVT-PEI-WGA SPA Beads type A for 2 hours, spun at 1000 RPM for 5 min and suspended to a concentration of 300 ug bead/ml (0.15 ug membrane, 15 ug bead per well). Bead/membrane mix was incubated with 0.06 nM [$^{125}$I] Nle4, D-Phe7-α-MSH and 11 half-log concentrations of competitor ligand, in duplicate, in a total volume of 50 μl buffer per well (25 mM HEPES, 1 mM $MgCl_2$, 2.5 mM $CaCl_2$, 1% Pluronic F68, 1 complete EDTA protease inhibitor tablet/50 ml pH7). Non-specific binding was determined by the inclusion of 100 nM SHU9119. The reaction was initiated by the addition of bead/membranes and plates were incubated at room temperature for 12 hours (the first hour on a plate shaker), after which the amount of radioactivity present was determined using a Wallac plate counter. Ki values were determined by data analysis using appropriate software.

Nle4, D-Phe7-α-MSH Inhibition at the MC3 Receptor

Nle4, D-Phe7-α-MSH is a stable analogue of melanocyte-stimulating hormone (MSH), which is an agonist at the MC3 receptor (MC3R). Compounds can be evaluated for their ability to inhibit Nle4, D-Phe7-α-MSH binding to membranes from cells expressing the MC3R using a competition binding assay versus [$^{125}$I] Nle4, D-Phe7-α-MSH.

Cells expressing the MC3R were subject to homogenisation and the membrane fragment isolated by differential centrifugation. CHO-CRE MC3R cell membranes were coupled to PVT-PEI-WGA SPA Beads type A for 2 hours, spun at 1000 RPM for 5 mins and suspended to a final assay concentration of 800 ug bead/ml (1.2 ug membrane, 40 ug bead per well). Bead/membrane mix was incubated with 0.06 nM [$^{125}$I] Nle4, D-Phe7-α-MSH and 11 half-log concentrations of competitor ligand, in duplicate, in a total volume of 50 μl buffer per well (25 mM HEPES, 1 mM $MgCl_2$, 2.5 mM $CaCl_2$, 1% Pluronic F68, 1 complete EDTA protease inhibitor tablet/50 ml pH7). Non-specific binding was determined by the inclusion of 100 nM SHU9119. The reaction was initiated by the addition of bead/membranes and plates were incubated at room temperature for 12 hours (the first hour on a plate shaker), after which the amount of radioactivity present was determined using a Wallac plate counter. Ki values were determined by data analysis using appropriate software.

High Density Drug-Drug Interactions (DDI) 3 µM Cocktail Screen

A drug interaction is a situation in which a substance affects the activity of another drug, i.e. the effects are increased or decreased, or together they produce a new effect that neither produces on its own. Drug interactions may be the result of various processes but a relatively common one is where one drug affects the pharmacokinetics of another by inhibiting the cytochrome P450 that metabolises it. Because of the importance of these phenomena, assessment of the DDI potential for new chemical entities (NCEs) is considered important early on in the drug discovery process.

The DDI cocktail screen in human liver microsomes (HLM) is run in a fully automated fashion and the aim of the screen is to provide a single-point assessment of the DDI potential of new chemical entity (NCE; tested at 3 M) against the 4 primary cytochrome P450 enzymes, 1A2, 2D6, 2C9 and 3A4.

The substrate cocktail approach for P450 DDI utilizes human liver microsomes together with isoform-specific clinical drug probes and permits the simultaneous measurement of the inhibition of P450 1A2, 2C9, 2D6 & 3A4 activities in a single incubation. This is run in high throughput with simultaneous detection of metabolites by LC-MS/MS. This method has been thoroughly tested and evaluated using standard compounds. The probe substrates used are given in the table below.

| Microsome Source | Pooled human liver microsomes, |
| --- | --- |
| Microsome Concentration | 0.1 mg/mL |
| P450 Concentration | 0.03 µM |
| Regeneration System | NADPH (1.3 mM) |
| Assay Time | 8 min |
| Probe Substrate (Enzyme Probed) | Concentration |
| Tacrine (1A2) | 2 µM |
| Diclofenac (2C9) | 5 µM |
| Dextromethorphan (2D6) | 5 µM |
| Midazolam (3A4) | 2 µM |
| Inhibitors | Concentration |
| NCE (test compound) | 3 µM |
| Miconazole (universal control) | 3 µM |

Appearance of the metabolite of each substrate is measured over time in the presence and absence of the NCE (test compound/inhibitor) at a concentration of 3 µM. The compounds are assessed for their inhibitory potential as a percentage value and interpreted using the following scheme. These data are then used in conjunction with other measurements to evaluate the suitability of NCEs and to help with the design and progression of compounds.

| % Inhibition | IC50 |
| --- | --- |
| >75% | <1 µM |
| 25-75% | 1-10 µM |
| <25% | >10 µM |

In Vitro Metabolism Rate Determination (Human Liver Microsome (HLM); Rat Liver Microsome (RLM) Assay)

Many drugs are metabolised by the cytochrome P450 mono-oxygenase system. This enzyme is found in high concentrations in the liver and is bound to the endoplasmic reticulum of the hepatocyte. The enzyme system can be obtained in semi-purified state by the preparation of the hepatic microsomal fractions. Determining a compound's in vitro half-life in such a system provides a useful indicator of metabolic stability.

Materials and Reagents

All reagents are ANALAR grade.

1. 200 mM Phosphate buffer (Sigma)—100 ml 1M Phosphate buffer pH7.4 dissolved with 400 ml MilliQ water. If necessary, pH should be adjusted with concentrated orthophosphoric acid to pH 7.4, made up monthly and stored refrigerated (2-8° C.).

2. 0.1M $MgCl_2 6H_2O$ (BDH)—2.032 g dissolved in 100 ml MilliQ water, and stored refrigerated (2-8° C.).

3. 0.02M NADP (Sigma)—15.3 mg dissolved in 1000 µl MilliQ water—and then stored refrigerated (2-8° C.) for further use.

4. 0.1M D-L Isocitric acid (Sigma)—129 mg dissolved in 5 ml MilliQ water—and then stored refrigerated (2-8° C.) for further use.

5. Isocitric dehydrogenase, Type IV (Sigma)—stored refrigerated (2-8° C.).

6. Stock solution of substrate (approximately 1 mg/ml) in miscible organic solvents such as methanol, ethanol or water, stored refrigerated (2-8° C.).

7. 50 mM p-Nitroanisole (PNA) (Aldrich)—7.65 mg dissolved in 1 ml methanol, and stored refrigerated (2-8° C.) until ready for use.

8. 50 µM p-Nitrophenol (PNP) (Sigma)—0.69 mg dissolved in 100 ml water and stored refrigerated (2-8° C.).

9. 20% Trichloroacetic acid (TCA) (BDH)—20 g dissolved in 100 ml MilliQ water, made up in amber glassware and stored at room temperature.

10. 10M Sodium hydroxide (BDH)—40 g dissolved in 100 ml MilliQ water (care should be exercised when preparing this solution as this reaction is exothermic), made up in "safebreak" glassware and stored at room temperature.

11. Hepatic or Supermix microsomes stored at −80° C. should be defrosted immediately prior to use, kept on ice and dispensed.

12. MilliQ water.

13. Thermostatically controlled shaking water bath set to give a temperature in the incubation of approx 37° C.

14. Reagent for termination of incubation (typically organic solvent, acid or base).

Methodology for In Vitro Rate Determination Using Hepatic & Supermix Microsomes

The method outlined below is for a total incubation volume of 1.5 ml.

1. The following mixture is prepared in a test tube:

| Reagent | Stock concentration | Concentration in incubation | Volume added (for 1.5 ml incubation) |
|---|---|---|---|
| Phosphate buffer pH 7.4 | 200 mM | 50 mM | 375 µl |
| MgCl$_2$ | 0.1 M | 5 mM | 75 µl |
| Isocitric acid | 0.1 M | 5 mM | 75 µl |
| Isocitric dehydrogenase | on bottle | 1 unit per ml * | see below* |

*This volume is calculated for each new batch of isocitric dehydrogenase
e.g. Protein concentration = 18 mg/ml
Enzyme activity = 3.3 units/mg
therefore Specific activity = 3.3 × 18 units/ml = 59 units/ml For a 1.5 ml incubation 1.5 units of enzyme activity are required =

$$\frac{1.5}{59} \times 1000 = 25.4 \ \mu l.$$

2. Defrost microsomes at room temperature and add sufficient microsomes to give a final concentration of 0.5 nmol cytochrome P450/ml of incubation e.g. for a 1.5 ml incubation, the volume of microsomes to be added is:

$$\frac{P450 \text{ concentration required in incubation} \times \text{incubation volume}}{\text{cytochrome } P450 \text{ concentration in microsomal prep.}}$$

3. Add sufficient MilliQ water to give a total incubation volume of 1.425 ml.

4. Remove 237.5 µl of incubation mix and place in test tube for PNA positive control. Add 2.5 µl of PNA solution, whirlimix, and put tube into a rack in the thermostatically controlled shaking water bath 5. Remove 100 µl for no substrate control and dispense in test tube. Place test tube in a rack in the thermostatically controlled shaking water bath.

6. Add substrate to the incubation. The substrate should be at an initial concentration of 1 µM. The volume of substrate required in the remaining 1.162.5 ml incubation is calculated as follows:

$$\frac{RMM \times \text{incubation vol.} \times \text{initial conc. in incubation}}{1000 \times \text{stock substrate solution conc.}}$$

N.B. The volume of organic solvent added should not exceed 0.1% of the total incubation volume.

7. Remove 100 µl of incubation mix into test tube for no cofactor control. Whirlimix and put into a rack in the thermostatically controlled shaking water bath.

8. Pre-incubate the tube containing the incubation mix, also positive control and no cofactor tubes in the thermostatically controlled shaking water bath set at 37° C. for approx 5 min.

9. Add NADP to initiate reaction (75 µl to each 1.162.5 ml incubation mix, 12.5 µl to positive control tube and 5 µl to no substrate tube) and take first time point immediately. The PNA positive control, no cofactor control and no substrate tubes are incubated for the total incubation time.

10. Remove 100 µl aliquots up to 9 different sampling points from 0 to 60 min (usually 0, 3, 5, 10, 15, 20, 30, 45 & 60 min) and terminate reaction. Longer incubation times can be used, but, after 120 min the microsomes deteriorate. The reaction may be terminated by addition of organic solvent, acid or base. At the end of the incubation process the no cofactor and no substrate controls in a similar manner i.e. terminate with the same reagent.

11. PNA positive control procedure:

After the final sample has been taken, remove the positive control and add 1 ml 20% TCA to this tube. Also prepare a tube containing 250 µl of a PNP standard at 50 µM, and add 1 ml 20% TCA. Whirlimix both tubes and leave for approx 5 min to allow the protein to precipitate.

Centrifuge both tubes for approx 5 min in an instrument set at 3500 rpm. Remove 1 ml of supernatant and place into clean test tubes, discard the remainder.

Add 1 ml 10M NaOH to the supernatant, whirlimix, and leave to stand for approx 5 min. Blank spectrophotometer with distilled water at 400 nm then measure absorbance of the PNP standard against distilled water. The microsomal 4-nitroanisole O-demethylase activity is calculated as follows:

Calculation of Results $$\frac{\text{Absorbance sample} \times n\text{moles } PNP \text{ in standard (ie 12.5} n\text{moles)}}{\text{Absorbance } PNP \text{ std} \times 60 \times 0.125} = n\text{moles/min/} n\text{mol } P450$$

The activity value from the incubation MUST be equal to or greater than 85% of the mean value of the batch used for the incubation to be valid. If this criteria is not met, then the incubation must be repeated.

11. Analyse samples (including no cofactor and no substrate control) by a specific assay for the substrate to determine the disappearance kinetics.

Analysis of Data

Data obtained using the procedure described above can be quantified in terms of the substrates in vitro intrinsic clearance (Clint). Providing that the substrate concentration is below Km, the metabolism should be 1st order giving a log-linear plot of substrate disappearance with time.

The in vitro half-life of the substrate can be determined by plotting the natural logarithm (ln) of a measure of relative substrate concentration (e.g. drug/internal standard ratio) against time and fitting the line of best fit to this data. The gradient of this line is the first order rate constant (k) for the substrate disappearance and is determined by regression analysis. This rate constant can be converted to the half-life according to the following equation.

$$\text{in vitro half-life } (t_{1/2}) = -\frac{\text{Ln}2}{k}$$

Alternatively the rate constant can be converted to an intrinsic clearance (Clint) according to the following equation:—

Clint(µl/min/mg)=(k/protein concentration in incubation (mg/ml))*1000

Administration Methods

Compounds of the invention intended for pharmaceutical use may be administered as crystalline or amorphous products. They may be obtained, for example, as solid plugs, powders, or films by methods such as precipitation, crystallization, freeze-drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

Accordingly the present invention provides for a pharmaceutical composition comprising a compound of formula (I) and a pharmaceutically acceptable diluent or carrier.

Any suitable route of administration may be employed for providing a mammal, especially a human with an effective dosage of a compound of the present invention. For example, oral (including buccal and sublingual administration), rectal, topical, parental, ocular, pulmonary, nasal, and the like may be employed. Dosage forms include tablets, troches, dispersions, suspensions, solutions, capsules, creams, ointments, aerosols, and the like. Preferably compounds of formula (I) are administered orally or intranasally.

The effective dosage of active ingredient employed may vary depending on the particular compound employed, the mode of administration, characteristics of the mammal to be treated (e.g. body weight), the condition being treated and the severity of the condition being treated. Such dosage may be ascertained readily by a person skilled in the art.

For the treatment of sexual dysfunction compounds of the present invention are given in a dose range of from about 0.001 milligram (mg) to about 1000 mg, preferably from about 0.001 mg to about 500 mg, more preferably from about 0.001 mg to about 100 mg, even more preferably from about 0.001 mg to about 50 mg and especially from about 0.002 mg to about 25 mg per kilogram of body weight, preferably as a single dose orally or as a nasal spray. For example, oral administration may require a total daily dose of from about 0.1 mg up to about 1000 mg, while an intravenous dose may only require from about 0.001 mg up to about 100 mg. The total daily dose may be administered in single or divided doses and may, at the physician's discretion, fall outside of the typical range given herein.

When treating obesity, in conjunction with diabetes and/or hyperglycemia, or alone, generally satisfactory results are obtained when the compounds of the present invention are administered at a daily dosage of from about 0.0001 mg to about 1000 mg, preferably about 0.001 mg to about 500 mg, more preferably about 0.005 mg to about 100 mg and especially about 0.005 mg to about 50 mg per kilogram of animal body weight, preferably given in a single dose or in divided doses two to six times a day, or in sustained release form. In the case of a 70 kg adult human, the total daily dose will generally be from about 0.7 mg up to about 3500 mg. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 mg up to about 100 mg per kilogram of animal body weight, preferably given in a single dose or in divided doses two to six times a day, or in sustained release form. In the case of a 70 kg adult human, the total daily dose will generally be from about 0.07 mg up to about 350 mg. This dosage regimen may be adjusted to provide the optimal therapeutic response.

These dosages are based on an average human subject having a weight of about 65 kg to 70 kg. The physician will readily be able to determine doses for subjects whose weight falls outside this range, such as infants, the elderly and the obese.

The compounds of the invention may be administered orally. Oral administration may involve swallowing, so that the compound enters the gastrointestinal tract, and/or buccal, lingual or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14 by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used.

Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose, blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (I). The overall daily dose will typically be in the range 0.001 mg to 40 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

The invention is illustrated by the following no-limiting examples in which the following abbreviations and definitions are used:

AP3 autopurification
APCl atmospheric pressure chemical ionisation
Arbocel® filter agent
br broad
Celite® filter agent
δ chemical shift
d doublet
dd double doublet
DCM dichloromethane
DMAP 4-dimethylaminopyridine
DMF dimethylformamide
EDCl 1-(3-dimethylaminopropyl)-3-ethyl-carbodiimide hydrochloride
EI electrospray ionisation
EtOAc ethyl acetate
h hour
HATU O-(7-azabenzotriazol-1-yl)-N,N,N',N'-tetramethyluronium hexafluorophosphate
HBTU 2-{1H-benzotriazol-1-yl}-1,1,3,3-tetramethyluronium hexafluorophosphate
LRMS low resolution mass spectrum
m multiplet
m/z Mass:charge ratio (mass spectrum peak)
min minute NMR nuclear magnetic resonance
Prep preparation
RT room temperature
s singlet
TBTU 2-{1H-benzotriazol-1-yl}-1,1,3,3-tetramethyluronium tetrafluoroborate
THF tetrahydrofuran
t triplet

EXAMPLES

Examples 1-57 were prepared according to scheme 1.

Example 1

6-[(3S,4R)-3-{[4-acetyl-5-(4-methoxyphenyl)-1,4-diazocan-1-yl]carbonyl}-4-(2,4-difluorophenyl)pyrrolidin-1-yl]pyridazine-3-carbonitrile

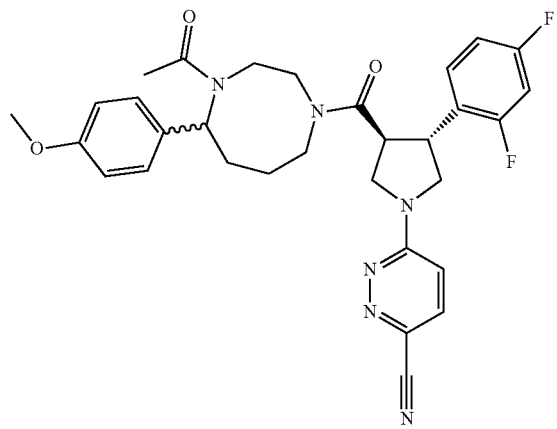 [SMILES: COc1ccc(C2CCCN(C(=O)[C@@H]3CN(c4ccc(C#N)nn4)C[C@H]3c3ccc(F)cc3F)CCN2C(C)=O)cc1]

To a solution of the compound of preparation 77 (45 mg, 0.084 mmol) in DCM (5 mL) were added pyridine (27.3 µL, 0.338 mmol) and acetylchloride (12 µL, 0.169 mmol). The reaction mixture was stirred at RT for 16 h. Starting material was still present so further pyridine (13.65 µL, 0.169 mmol) and acetylchloride (6 µL, 0.084 mmol) were added and stirring continued for a further 16 h. The reaction was concentrated in vacuo and then diluted with EtOAc (20 mL) and washed with 5% aqueous citric acid solution (20 ml). The organic extract was dried over magnesium sulfate and concentrated in vacuo to give the crude residue. Purification by column chromatography on silica gel using dichloromethane:methanol (100:0 to 95:5 to 90:10) gave 43 mg (89%) of the title compound as a mixture of epimers as a yellow foam.

$^1$H NMR (400 MHz, CD$_3$OD) δ 1.2-2.2 (4H, br, m), 2.2 (3H, s), 3.0-4.5 (11H, m), 5.1 (m, 1H), 6.7-7.2 (7H, m), 7.7 (1H, m), 7.9 (1H, m).

LRMS: m/z APCl$^+$ 575 [MH$^+$].

Examples 2-38

These compounds were prepared by the method of example 1 starting from the appropriate carboxylic acid chloride and the appropriate precursor as listed in the table.

| Example | Structure | MS MH+ ion | AP3 Rf | Precursor (Prep #) |
|---|---|---|---|---|
| 2$^A$ | | 563 | — | 76 |

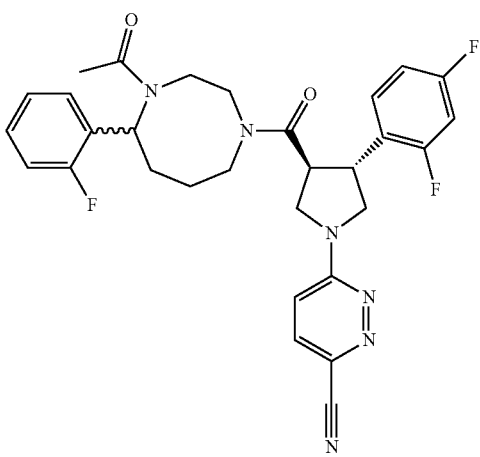 [SMILES: CC(=O)N1CCN(C(=O)[C@@H]2CN(c3ccc(C#N)nn3)C[C@H]2c2ccc(F)cc2F)CCCC1c1ccccc1F]

-continued
| Example | Structure | MS MH+ ion | AP3 Rf | Precursor (Prep #) |
|---|---|---|---|---|
| 3[A] | 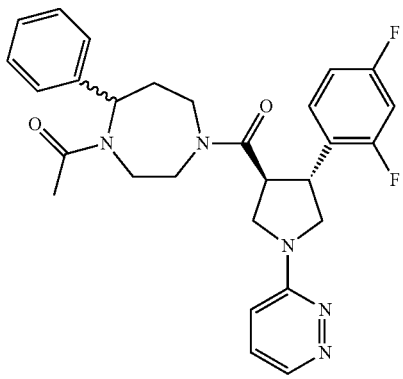 [SMILES: CC(=O)N1CCN(C(=O)[C@@H]2CN(c3cccnn3)C[C@H]2c2ccc(F)cc2F)CCC1c1ccccc1] | 506 | 2.39 | 68 |
| 4[A] | 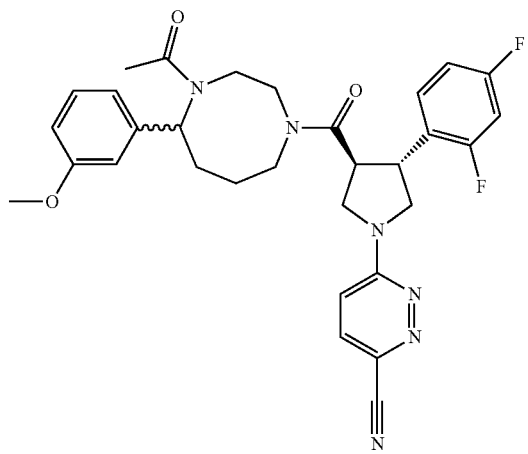 | 575 | — | 75 |
| 5[B] | 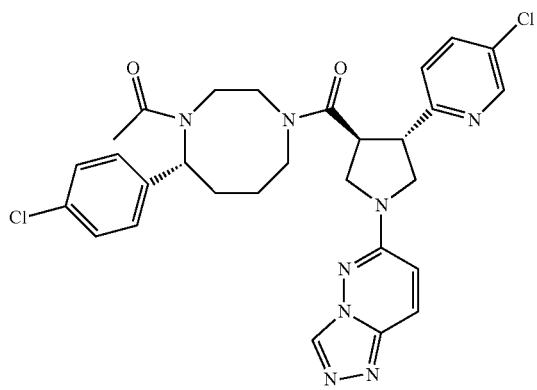 [SMILES: CC(=O)N1CCN(C(=O)[C@@H]2CN(c3ccc4nncn4n3)C[C@H]2c2ccc(Cl)cn2)CCC[C@@H]1c1ccc(Cl)cc1] | 593 | 3.06 | 87 |

-continued

| Example | Structure | MS MH+ ion | AP3 Rf | Precursor (Prep #) |
|---------|-----------|------------|--------|---------------------|
| 6[B] | 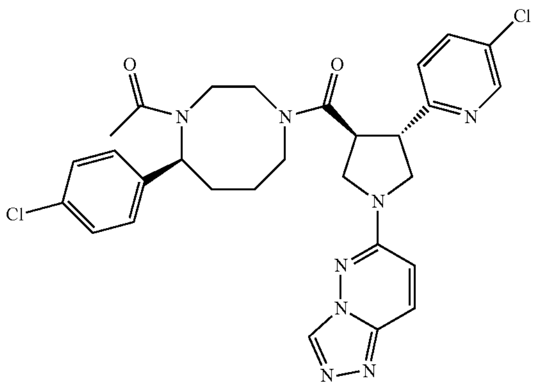 [SMILES: CC(=O)N1CCN(C(=O)[C@@H]2CN(c3ccc4nncn4n3)C[C@H]2c2ccc(Cl)cn2)CCC[C@H]1c1ccc(Cl)cc1] | 593 | 3.22 | 86 |
| 7[B] | 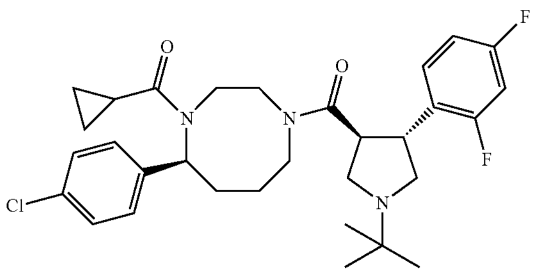 [SMILES: CC(C)(C)N1C[C@@H](C(=O)N2CCC[C@@H](c3ccc(Cl)cc3)N(C(=O)C3CC3)CC2)[C@H](c2ccc(F)cc2F)C1] | 558 | 2.61 | 70 |
| 8[B] | 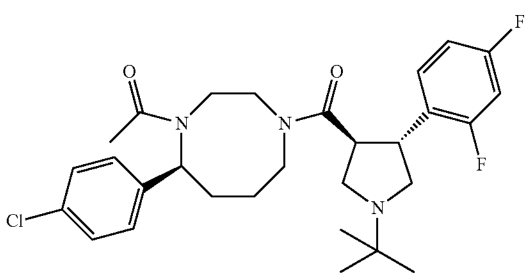 [SMILES: CC(=O)N1CCN(C(=O)[C@@H]2CN(C(C)(C)C)C[C@H]2c2ccc(F)cc2F)CCC[C@H]1c1ccc(Cl)cc1] | 532 | 3.44 | 70 |
| 9[B] | 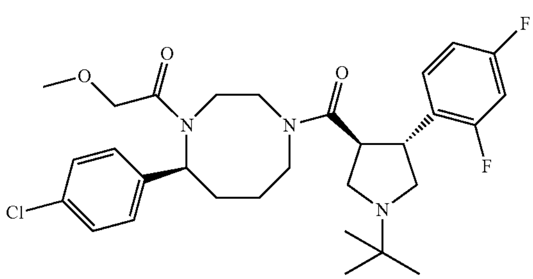 [SMILES: COCC(=O)N1CCN(C(=O)[C@@H]2CN(C(C)(C)C)C[C@H]2c2ccc(F)cc2F)CCC[C@H]1c1ccc(Cl)cc1] | 562 | 3.44 | 70 |
| 10[B] | 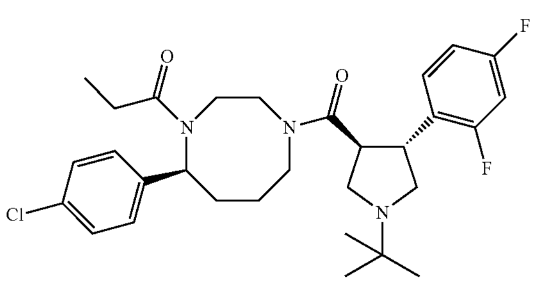 [SMILES: CCC(=O)N1CCN(C(=O)[C@@H]2CN(C(C)(C)C)C[C@H]2c2ccc(F)cc2F)CCC[C@H]1c1ccc(Cl)cc1] | 546 | 3.59 | 70 |

-continued

| Example | Structure | MS MH+ ion | AP3 Rf | Precursor (Prep #) |
|---|---|---|---|---|
| 11[B] | 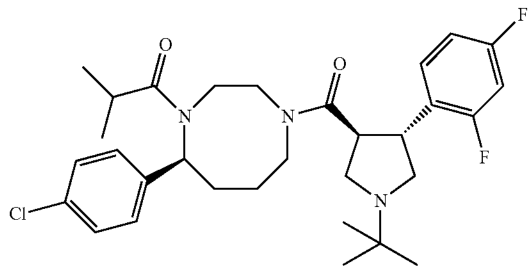 [SMILES: CC(C)C(=O)N1CCN(C(=O)[C@@H]2CN(C(C)(C)C)C[C@H]2c2ccc(F)cc2F)CCC[C@H]1c1ccc(Cl)cc1] | 560 | 3.73 | 70 |
| 12[B] | 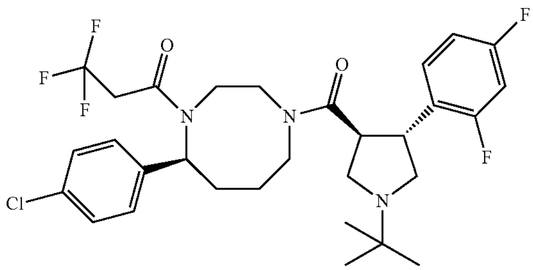 [SMILES: CC(C)(C)N1C[C@@H](C(=O)N2CCC[C@@H](c3ccc(Cl)cc3)N(C(=O)CC(F)(F)F)CC2)[C@H](c2ccc(F)cc2F)C1] | 600 | 3.74 | 70 |
| 13[B] | 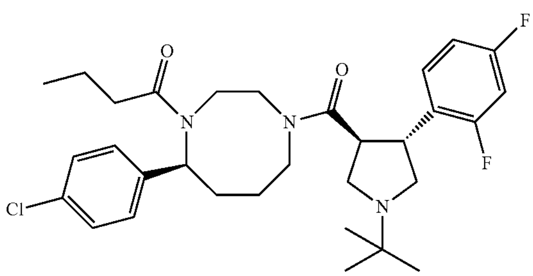 [SMILES: CCCC(=O)N1CCN(C(=O)[C@@H]2CN(C(C)(C)C)C[C@H]2c2ccc(F)cc2F)CCC[C@H]1c1ccc(Cl)cc1] | 560 | 3.8 | 70 |
| 14[B] | 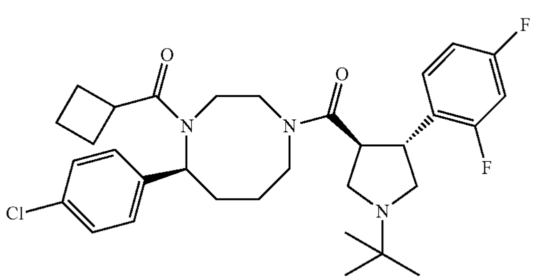 [SMILES: CC(C)(C)N1C[C@@H](C(=O)N2CCC[C@@H](c3ccc(Cl)cc3)N(C(=O)C3CCC3)CC2)[C@H](c2ccc(F)cc2F)C1] | 572 | 3.88 | 70 |
| 15[B] | 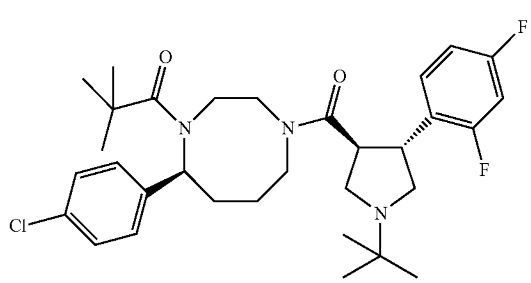 [SMILES: CC(C)(C)C(=O)N1CCN(C(=O)[C@@H]2CN(C(C)(C)C)C[C@H]2c2ccc(F)cc2F)CCC[C@H]1c1ccc(Cl)cc1] | 574 | 3.89 | 70 |

-continued

| Example | Structure | MS MH+ ion | AP3 Rf | Precursor (Prep #) |
|---|---|---|---|---|
| 16[B] | 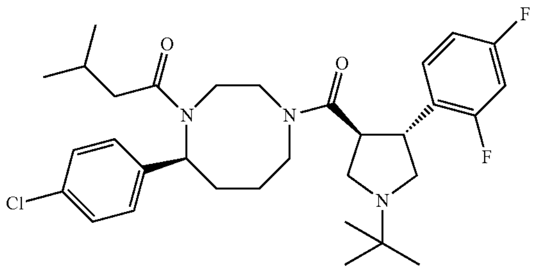 [SMILES: CC(C)CC(=O)N1CCN(C(=O)[C@@H]2CN(C(C)(C)C)C[C@H]2c2ccc(F)cc2F)CCC[C@H]1c1ccc(Cl)cc1] | 574 | 3.91 | 70 |
| 17[B] | 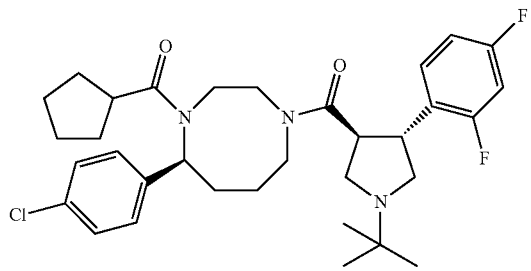 [SMILES: CC(C)(C)N1C[C@@H](C(=O)N2CCC[C@@H](c3ccc(Cl)cc3)N(C(=O)C3CCCC3)CC2)[C@H](c2ccc(F)cc2F)C1] | 586 | 3.96 | 70 |
| 18[A] | 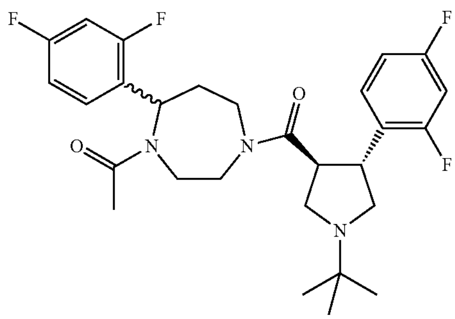 [SMILES: CC(=O)N1CCN(C(=O)[C@@H]2CN(C(C)(C)C)C[C@H]2c2ccc(F)cc2F)CCC1c1ccc(F)cc1F] | 520 | 2.39 | 69 |
| 19[B] | 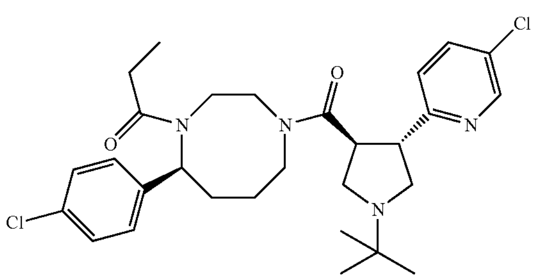 [SMILES: CCC(=O)N1CCN(C(=O)[C@@H]2CN(C(C)(C)C)C[C@H]2c2ccc(Cl)cn2)CCC[C@H]1c1ccc(Cl)cc1] | 545 | 2.53 | 88 |
| 20[B] | 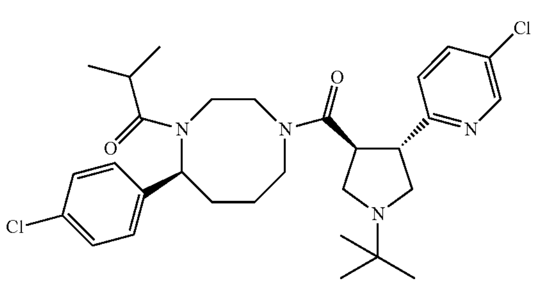 [SMILES: CC(C)C(=O)N1CCN(C(=O)[C@@H]2CN(C(C)(C)C)C[C@H]2c2ccc(Cl)cn2)CCC[C@H]1c1ccc(Cl)cc1] | 559 | 2.66 | 88 |

-continued

| Example | Structure | MS MH+ ion | AP3 Rf | Precursor (Prep #) |
|---------|-----------|------------|--------|--------------------|
| 21[B]   | 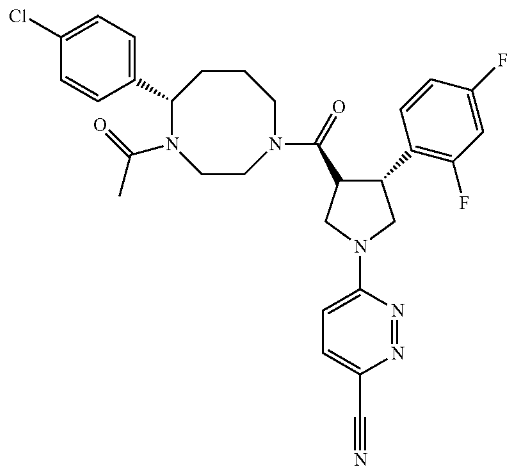          | 579        | 3.31   | 81                 |
| 22[B]   | 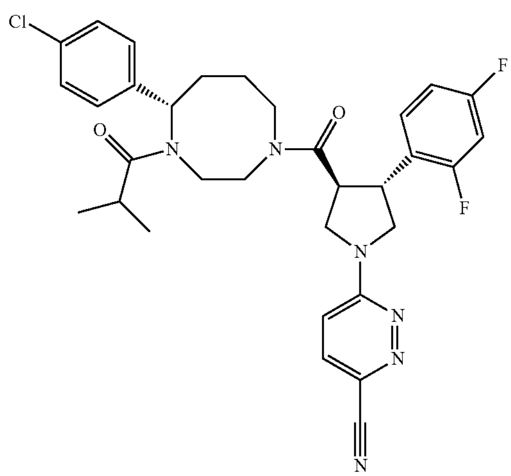 [SMILES: CC(C)C(=O)N1CCN(C(=O)[C@@H]2CN(c3ccc(C#N)nn3)C[C@H]2c2ccc(F)cc2F)CCC[C@H]1c1ccc(Cl)cc1]          | 607        | 3.51   | 81                 |
| 23[B]   | 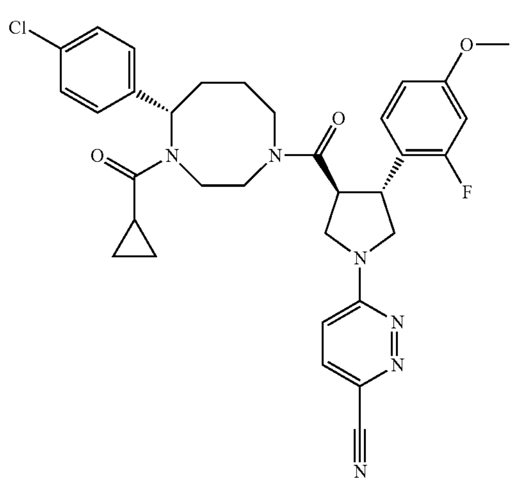 [SMILES: COc1ccc([C@@H]2CN(c3ccc(C#N)nn3)C[C@H]2C(=O)N2CCC[C@@H](c3ccc(Cl)cc3)N(C(=O)C3CC3)CC2)c(F)c1]          | 617        | 3.36   | 72                 |

| Example | Structure | MS MH+ ion | AP3 Rf | Precursor (Prep #) |
|---------|-----------|------------|--------|--------------------|
| 24[B]   | 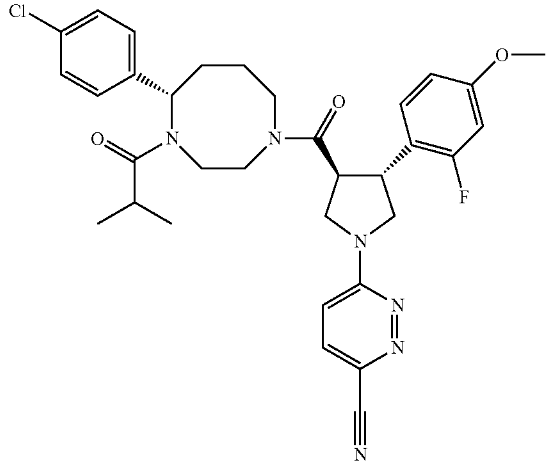 [SMILES: COc1ccc([C@@H]2CN(c3ccc(C#N)nn3)C[C@H]2C(=O)N2CCC[C@@H](c3ccc(Cl)cc3)N(C(=O)C(C)C)CC2)c(F)c1]          | 619        | 3.38   | 72                 |
| 25[B]   | 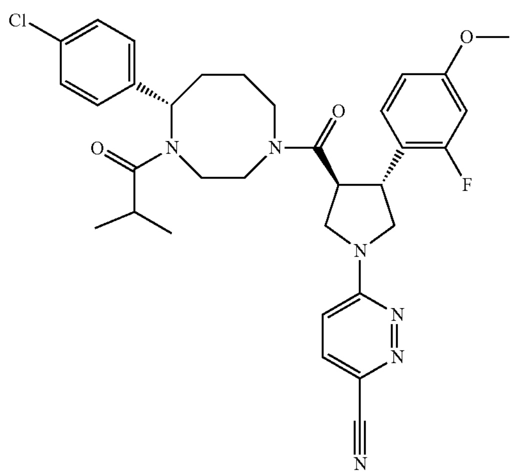 [SMILES: COc1ccc([C@@H]2CN(c3ccc(C#N)nn3)C[C@H]2C(=O)N2CCC[C@@H](c3ccc(Cl)cc3)N(C(=O)C(C)C)CC2)c(F)c1]          | 619        | 3.38   | 72                 |
| 26[B]   | 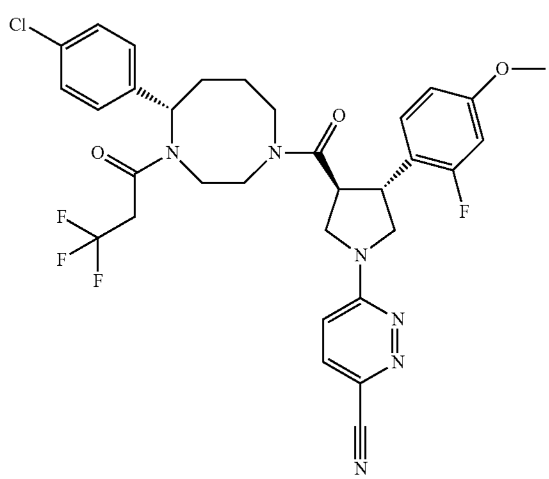 [SMILES: COc1ccc([C@@H]2CN(c3ccc(C#N)nn3)C[C@H]2C(=O)N2CCC[C@@H](c3ccc(Cl)cc3)N(C(=O)CC(F)(F)F)CC2)c(F)c1]          | 659        | 3.54   | 72                 |

| Example | Structure | MS MH+ ion | AP3 Rf | Precursor (Prep #) |
|---|---|---|---|---|
| 27[B] | 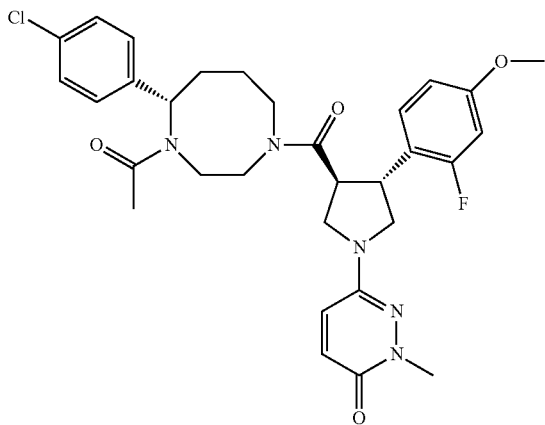 [SMILES: COc1ccc([C@@H]2CN(c3ccc(=O)n(C)n3)C[C@H]2C(=O)N2CCC[C@@H](c3ccc(Cl)cc3)N(C(C)=O)CC2)c(F)c1] | 596 | 3.12 | 80 |
| 28[B] | 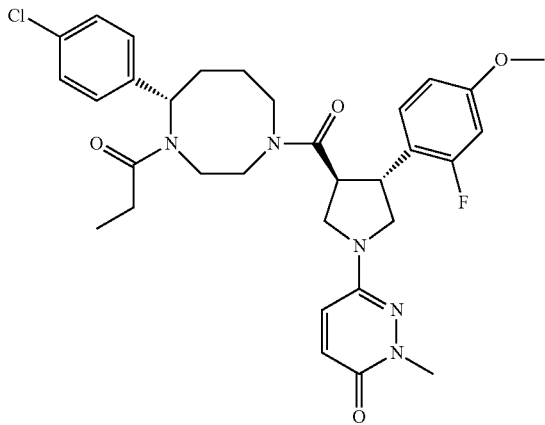 [SMILES: CCC(=O)N1CCN(C(=O)[C@@H]2CN(c3ccc(=O)n(C)n3)C[C@H]2c2ccc(OC)cc2F)CCC[C@H]1c1ccc(Cl)cc1] | 610 | 3.22 | 80 |
| 29[B] | 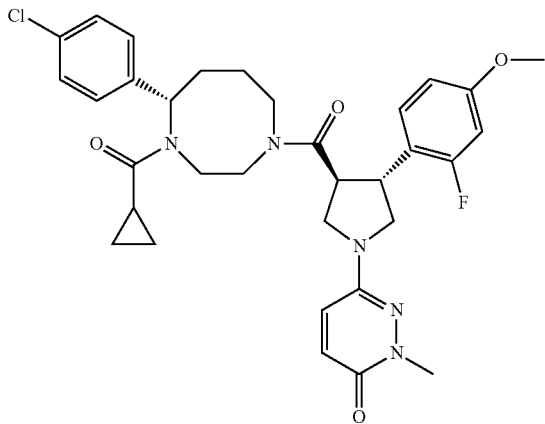 [SMILES: COc1ccc([C@@H]2CN(c3ccc(=O)n(C)n3)C[C@H]2C(=O)N2CCC[C@@H](c3ccc(Cl)cc3)N(C(=O)C3CC3)CC2)c(F)c1] | 622 | 3.28 | 80 |

| Example | Structure | MS MH+ ion | AP3 Rf | Precursor (Prep #) |
|---|---|---|---|---|
| 30[B] | 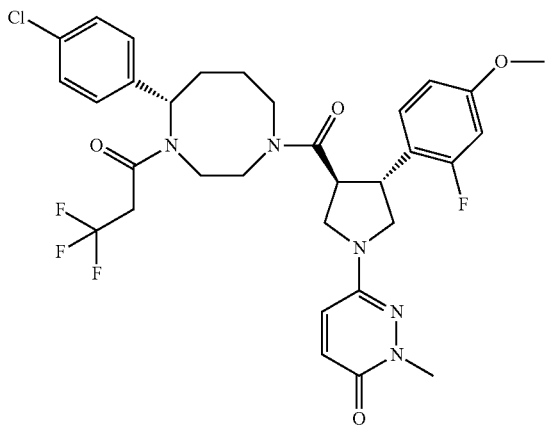 [SMILES: COc1ccc([C@@H]2CN(c3ccc(=O)n(C)n3)C[C@H]2C(=O)N2CCC[C@@H](c3ccc(Cl)cc3)N(C(=O)CC(F)(F)F)CC2)c(F)c1] | 664 | 3.29 | 80 |
| 31[B] | 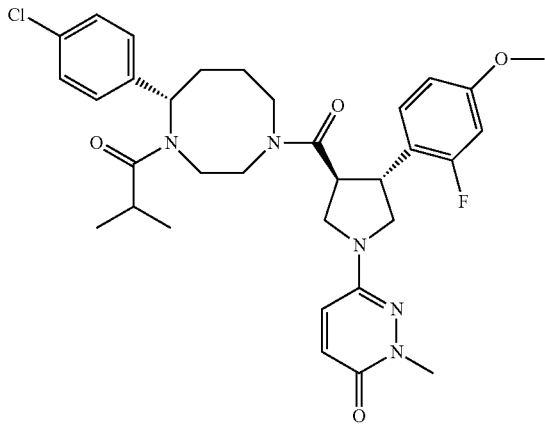 [SMILES: COc1ccc([C@@H]2CN(c3ccc(=O)n(C)n3)C[C@H]2C(=O)N2CCC[C@@H](c3ccc(Cl)cc3)N(C(=O)C(C)C)CC2)c(F)c1] | 624 | 3.35 | 80 |
| 32[B] | 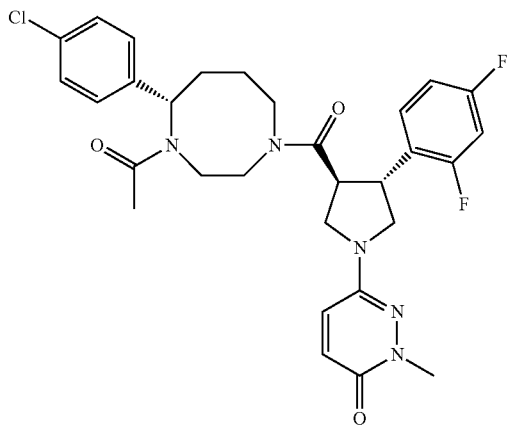 [SMILES: CC(=O)N1CCN(C(=O)[C@@H]2CN(c3ccc(=O)n(C)n3)C[C@H]2c2ccc(F)cc2F)CCC[C@H]1c1ccc(Cl)cc1] | 584 | 3.05 | 66 |

| Example | Structure | MS MH+ ion | AP3 Rf | Precursor (Prep #) |
|---|---|---|---|---|
| 33[B] | 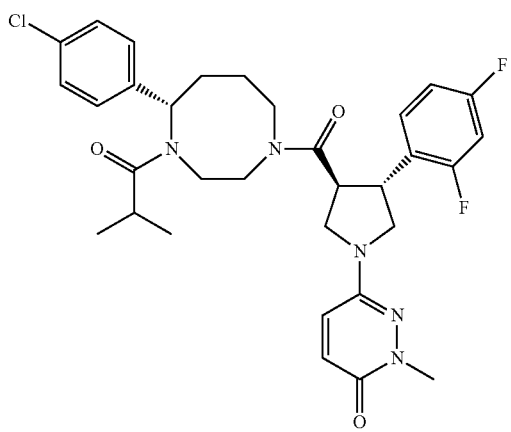 [SMILES: CC(C)C(=O)N1CCN(C(=O)[C@@H]2CN(c3ccc(=O)n(C)n3)C[C@H]2c2ccc(F)cc2F)CCC[C@H]1c1ccc(Cl)cc1] | 612 | 3.2 | 66 |
| 34[B] | 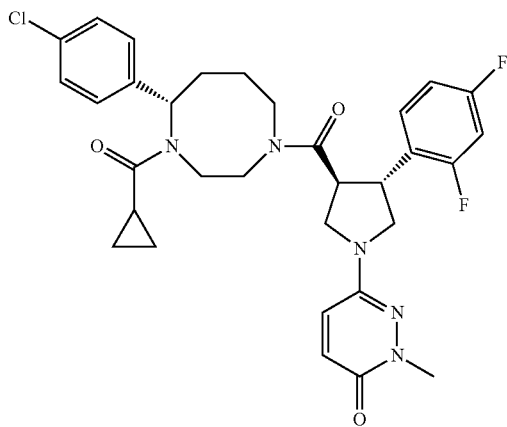 [SMILES: Cn1nc(N2C[C@@H](C(=O)N3CCC[C@@H](c4ccc(Cl)cc4)N(C(=O)C4CC4)CC3)[C@H](c3ccc(F)cc3F)C2)ccc1=O] | 610 | 3.22 | 66 |
| 35[B] | 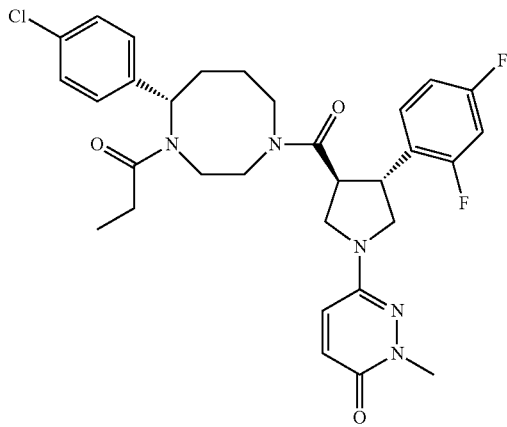 [SMILES: CCC(=O)N1CCN(C(=O)[C@@H]2CN(c3ccc(=O)n(C)n3)C[C@H]2c2ccc(F)cc2F)CCC[C@H]1c1ccc(Cl)cc1] | 598 | 3.22 | 66 |

| Example | Structure | MS MH+ ion | AP3 Rf | Precursor (Prep #) |
|---|---|---|---|---|
| 36[B] | 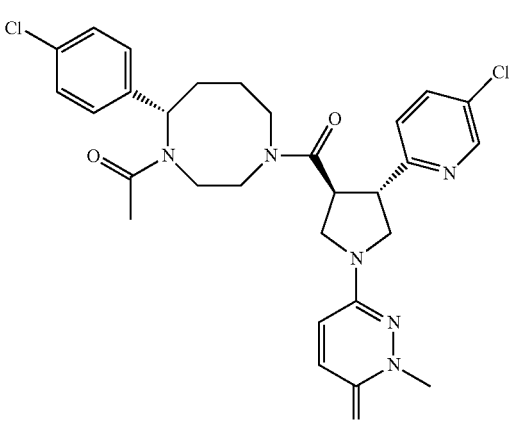 | 583 | 2.99 | 82 |
| 37[B] | 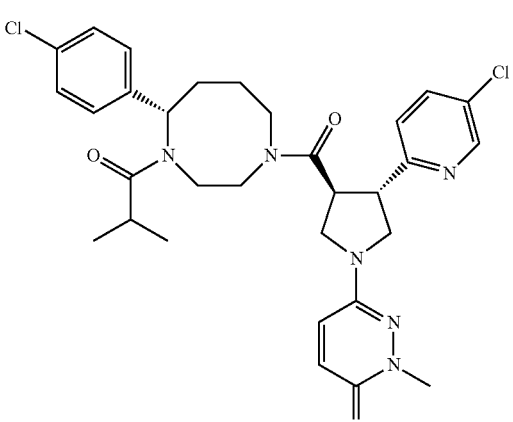 | 611 | 3.21 | 82 |
| 38[B] | 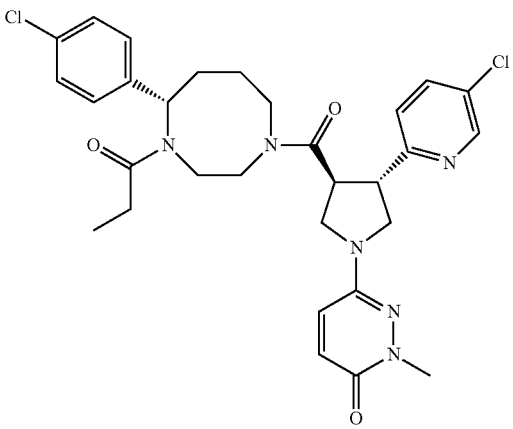 | 597 | 3.22 | 82 |
A = mixture of epimers;
B = single epimer

Example 39

6-[(3R,4S)-3-(2,4-difluorophenyl-1)-4-{[4-(methyl-sulfonyl)-5-phenyl-1,4-diazocan-1-yl]carbonyl}pyrrolidin-1-yl]nicotinonitrile

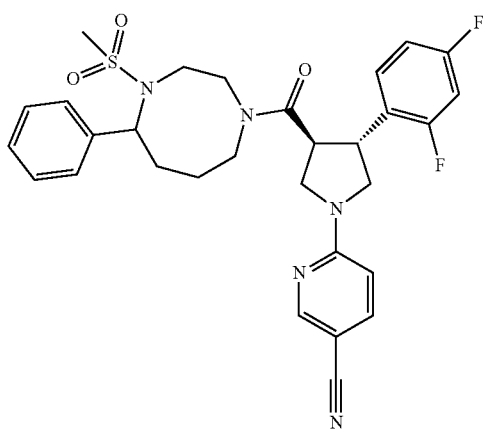 [SMILES: CS(=O)(=O)N1CCN(C(=O)[C@@H]2CN(c3ccc(C#N)cn3)C[C@H]2c2ccc(F)cc2F)CCCC1c1ccccc1]

To a solution of the compound of preparation 73 (25 mg, 0.05 mmol) in DCM (5 mL) were added triethylamine (28 μL, 0.2 mmol) and methanesulphonyl chloride (8 μL, 0.1 mmol). The reaction mixture was stirred at RT for 72 h.

Starting material was still present so catalytic DMAP (2 mg) was added and stirring continued for a further 16 h. The reaction was diluted with DCM (10 mL) and washed with water (10 ml). The organic extract was dried over magnesium sulfate and concentrated in vacuo to give the crude residue. Purification by column chromatography on silica gel using dichloromethane:methanol (100:0 to 95:5) gave 16 mg (55%) of the title compound as a white solid. The title compound is a single epimer, but with unknown absolute configuration at the point of 5-phenyl substitution.

$^1$H NMR (400 MHz, CD$_3$OD) δ1.2-2.2 (4H, br, m), 2.34 (3H, s), 2.39 (3H, s), 3.07 (1H, m), 3.4-4.4 (12H, m), 6.61 (1H, t), 6.93 (2H, m), 7.09 (1H, d), 7.35 (4H, m), 7.5 (1H, m), 7.73 (1H, m), 8.39 (1H, d). LRMS: APCl$^+$ m/z 580 [MH$^+$].

Examples 40-43

These compounds were prepared by the method of example 39 using methanesulphonyl chloride and the appropriate precursor as listed in the table.

| Example | Structure | MS MH+ ion | AP3 Rf | Precursor (Prep #) |
|---|---|---|---|---|
| 40$^C$ | | 580 | — | 74 |
| 41$^A$ | | 590 | — | 91 |

| Example | Structure | MS MH+ ion | AP3 Rf | Precursor (Prep #) |
|---|---|---|---|---|
| 42[A] | 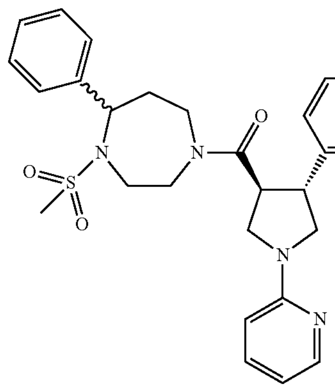 | 542 | 2.54 | 68 |
| 43[A] | 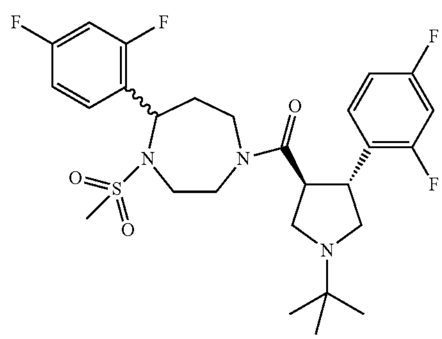 | 556 | 2.46 | 69 |

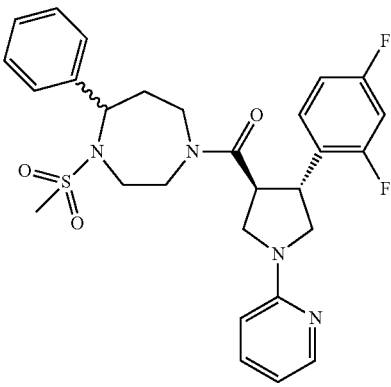 [SMILES: CS(=O)(=O)N1CCN(C(=O)[C@@H]2CN(c3ccccn3)C[C@H]2c2ccc(F)cc2F)CCC1c1ccccc1]

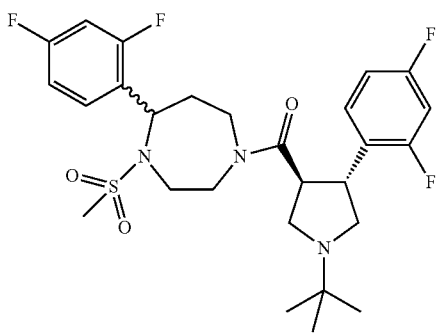

A = mixture of epimers;
C = single epimer with opposite configuration at site of 5-phenyl substitution

Example 44

4-{[(3S,4R)-1-tert-butyl-4-(2,4-difluorophenyl)pyrrolidin-3-yl]carbonyl}-8S-(4-chlorophenyl)-N,N-diethyl-1,4-diazocane-1-carboxamide

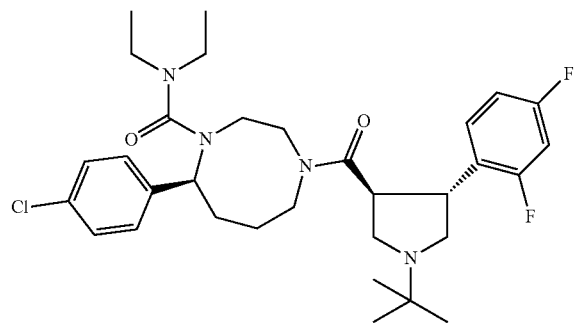 [SMILES: CCN(CC)C(=O)N1CCN(C(=O)[C@@H]2CN(C(C)(C)C)C[C@H]2c2ccc(F)cc2F)CCC[C@H]1c1ccc(Cl)cc1]

To a solution of the compound of preparation 70 (40 mg, 0.082 mmol) in pyridine (1 mL) were added DMAP (50 mg, 0.41 mmol), and diethylcarbamoyl chloride (0.103 μL, 0.82 mmol). The reaction mixture was stirred in a microwave oven at 120° C. for 2 h then cooled to RT over 16 h. The reaction was diluted by adding 5% citric acid solution (10 mL) and extracted with EtOAc (3×10 mL). The combined organic extracts were washed with 5% citric acid solution (10 mL), sodium hydrogen carbonate solution (10 ml) and brine (10 ml), dried over sodium sulphate, filtered and concentrated in vacuo to give the crude residue which was purified by AP3 (rf 2.68) to obtain the title compound (15 mg=31% yield). LRMS: APCl+ m/z 589 [MH+].

Examples 45-46

These compounds were prepared by the method of example 44 using the appropriate commercially available carbamoyl chloride and the appropriate precursor as listed in the table.

| Example | Structure | MS MH+ ion | AP3 Rf | Precursor (Prep #) |
|---|---|---|---|---|
| 45[B] | 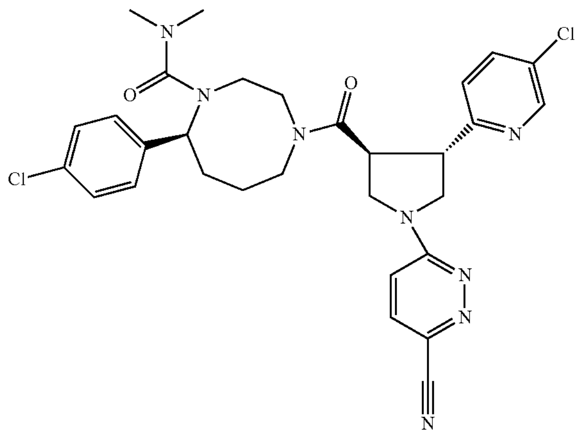 [SMILES: CN(C)C(=O)N1CCN(C(=O)[C@@H]2CN(c3ccc(C#N)nn3)C[C@H]2c2ccc(Cl)cn2)CCC[C@H]1c1ccc(Cl)cc1] | 607 | 3.45 | 90 |
| 46[B] | 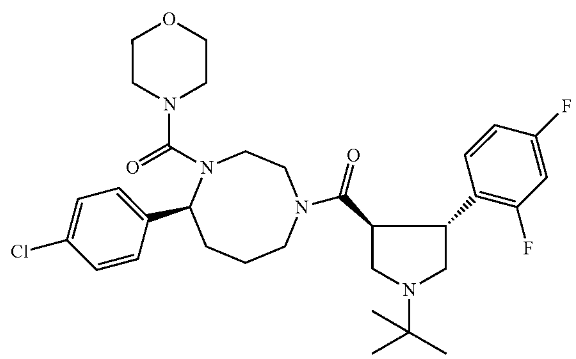 [SMILES: CC(C)(C)N1C[C@@H](C(=O)N2CCC[C@@H](c3ccc(Cl)cc3)N(C(=O)N3CCOCC3)CC2)[C@H](c2ccc(F)cc2F)C1] | 603 | 2.54 | 70 |

B = single epimer

Example 47 methyl 8S-(4-chlorophenyl)-4-{[(3S,4S)-4-(5-chloropyridin-2-yl)-1-(1-methyl-6-oxo-1,6-dihydropyridazin-3-yl)pyrrolidin-3-yl]carbonyl}-1,4-diazocane-1-carboxylate

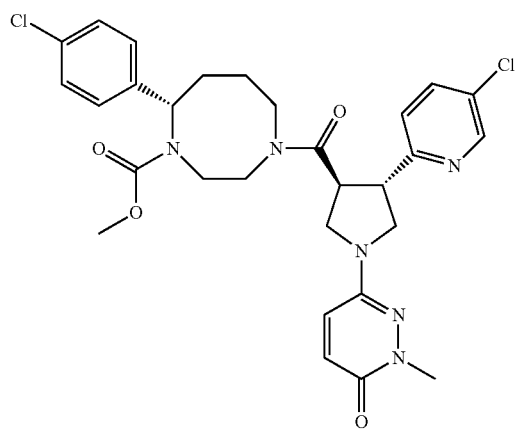 [SMILES: COC(=O)N1CCN(C(=O)[C@@H]2CN(c3ccc(=O)n(C)n3)C[C@H]2c2ccc(Cl)cn2)CCC[C@H]1c1ccc(Cl)cc1]

To a solution of the compound of preparation 82 (40 mg, 0.074 mmol) in DCM (5 mL) were added N,N-diisopropylethylamine (51 µL, 0.296 mmol) and methyl chloroformate (17 µL, 0.222 mmol). The reaction mixture was stirred at RT for 16 h. The reaction was diluted by adding potassium carbonate solution (10 mL) and extracted with DCM (2×3 mL). The combined organic extracts were concentrated in vacuo to give the crude residue. Purification by column chromatography on silica gel using ethyl acetate:methanol:0.88 ammonia (gradient from 98:2:0.2 to 80:20:3) gave 37 mg (83%) of the title compound as a yellow foam.

$^1$H NMR (400 MHz, CD$_3$OD) δ 1.10-1.30 (1H, m), 1.40-1.60 (1H, m), 1.70-1.80 (1H, m), 1.95-2.05 (1H, m), 2.10-2.25 (1H, m), 2.70-3.05 (2H, m), 3.35-4.10 (15H, m), 5.00-5.20 (1H, dd), 6.80-6.90 (1H, m), 6.95-7.05 (2H, m), 7.10-7.40 (4H, m), 7.60-7.70 (1H, m), 8.00-8.10 (1H, s). LRMS: EI$^+$ m/z 599 [MH$^+$].

Examples 48-57

These compounds were prepared by the method of example 47 using the appropriate commercially available chloroformate and the appropriate precursor as listed in the table.

| Example | Structure | MS MH+ ion | AP3 Rf | Precursor (Prep #) |
|---|---|---|---|---|
| 48[A] | 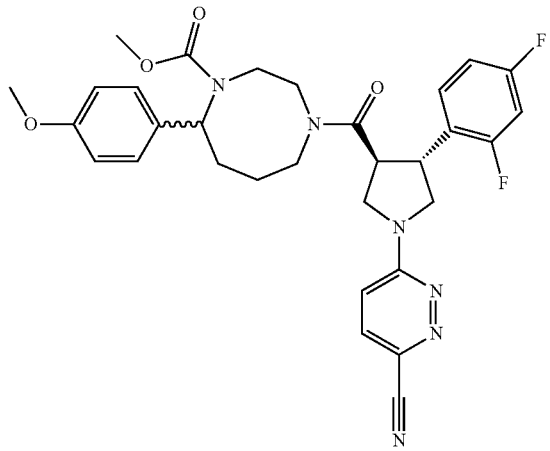 [SMILES: COC(=O)N1CCN(C(=O)[C@@H]2CN(c3ccc(C#N)nn3)C[C@H]2c2ccc(F)cc2F)CCCC1c1ccc(OC)cc1] | 591 | — | 77 |
| 49[A] | 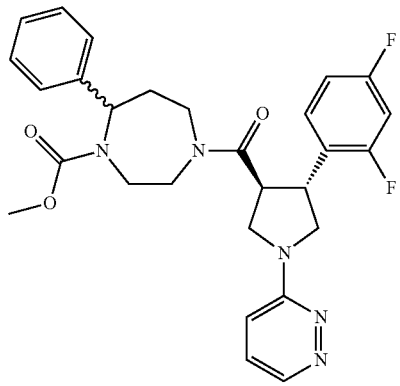 [SMILES: COC(=O)N1CCN(C(=O)[C@@H]2CN(c3cccnn3)C[C@H]2c2ccc(F)cc2F)CCC1c1ccccc1] | 522 | 2.54 | 68 |
| 50[A] | 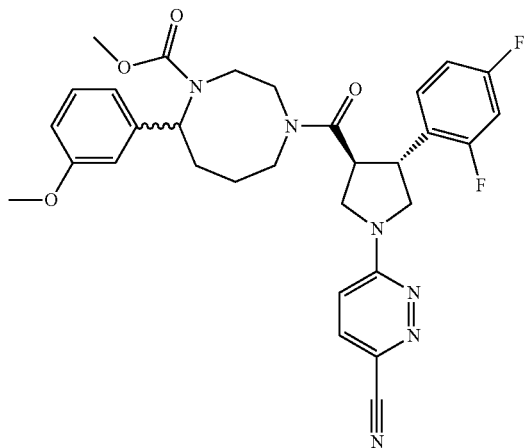 [SMILES: COC(=O)N1CCN(C(=O)[C@@H]2CN(c3ccc(C#N)nn3)C[C@H]2c2ccc(F)cc2F)CCCC1c1cccc(OC)c1] | 591 | — | 75 |

-continued

| Example | Structure | MS MH+ ion | AP3 Rf | Precursor (Prep #) |
|---|---|---|---|---|
| 51[B] | 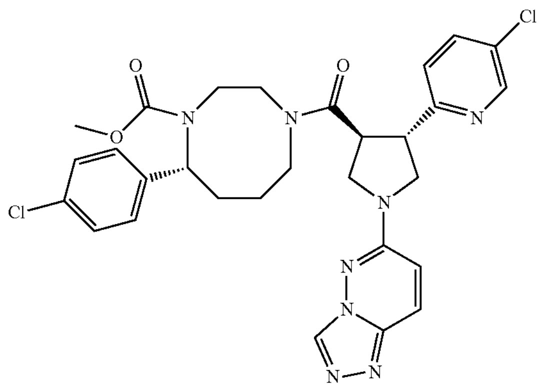 [SMILES: COC(=O)N1CCN(C(=O)[C@@H]2CN(c3ccc4nncn4n3)C[C@H]2c2ccc(Cl)cn2)CCC[C@@H]1c1ccc(Cl)cc1] | 609 | 3.36 | 87 |
| 52[B] | 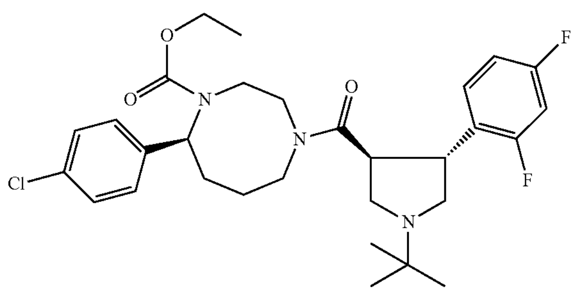 [SMILES: CCOC(=O)N1CCN(C(=O)[C@@H]2CN(C(C)(C)C)C[C@H]2c2ccc(F)cc2F)CCC[C@H]1c1ccc(Cl)cc1] | 562 | 2.59 | 70 |
| 53[B] | 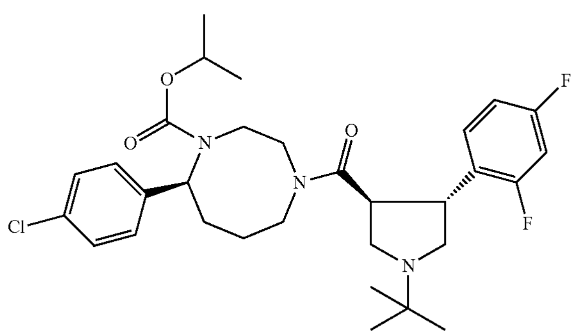 [SMILES: CC(C)OC(=O)N1CCN(C(=O)[C@@H]2CN(C(C)(C)C)C[C@H]2c2ccc(F)cc2F)CCC[C@H]1c1ccc(Cl)cc1] | 576 | 2.92 | 70 |
| 54[A] | 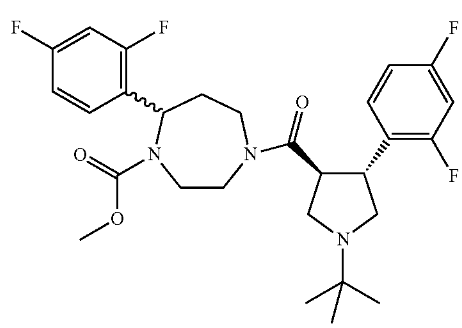 [SMILES: COC(=O)N1CCN(C(=O)[C@@H]2CN(C(C)(C)C)C[C@H]2c2ccc(F)cc2F)CCC1c1ccc(F)cc1F] | 536 | 2.46 | 69 |

-continued

| Example | Structure | MS MH+ ion | AP3 Rf | Precursor (Prep #) |
|---|---|---|---|---|
| 55[B] | 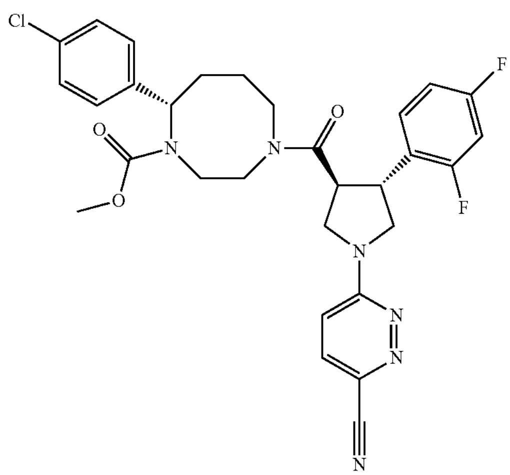 [SMILES: COC(=O)N1CCN(C(=O)[C@@H]2CN(c3ccc(C#N)nn3)C[C@H]2c2ccc(F)cc2F)CCC[C@H]1c1ccc(Cl)cc1] | 595 | 3.5 | 81 |
| 56[B] | 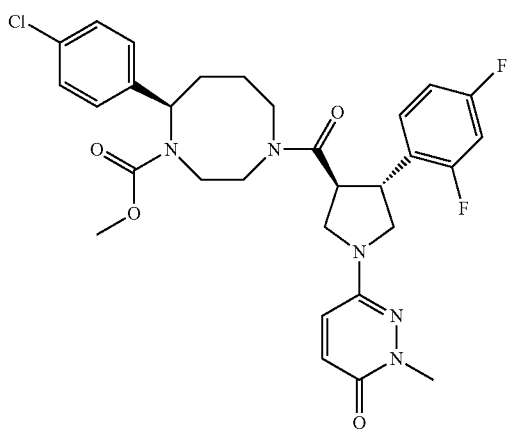 [SMILES: COC(=O)N1CCN(C(=O)[C@@H]2CN(c3ccc(=O)n(C)n3)C[C@H]2c2ccc(F)cc2F)CCC[C@@H]1c1ccc(Cl)cc1] | 600 | — | 67 |
| 57[A] | 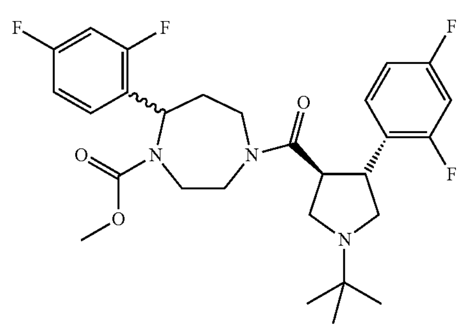 | 536 | 2.46 | 69 |

A = mixture of epimers;

B = single epimer

Examples 58-65 were prepared according to scheme 2.

Example 58

6-[(3S,4R)-3-[5S-(4-chlorophenyl)-4-(3,3,3-trifluoropropanoyl)-1,4-diazocan-1-yl]carbonyl}-4-(2,4-difluorophenyl)pyrrolidin-1-yl]pyridazine-3-carbonitrile

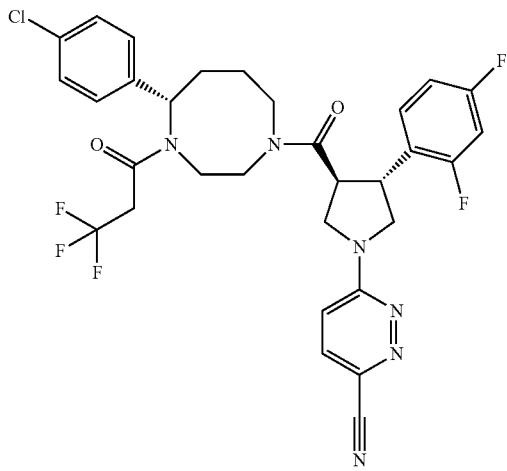 [SMILES: N#Cc1ccc(N2C[C@@H](C(=O)N3CCC[C@@H](c4ccc(Cl)cc4)N(C(=O)CC(F)(F)F)CC3)[C@H](c3ccc(F)cc3F)C2)nn1]

To a solution of the compound of preparation 81 (15 mg, 0.028 mmol) in DCM (1 mL) were added triethylamine (31 µL, 0.224 mmol), 3,3,3-trifluoropropionic acid (9 mg, 0.068 mmol) and HATU (32 mg, 0.084 mmol). The reaction mixture was stirred at RT for 16 h. The reaction was diluted by adding sodium hydrogen carbonate solution (2 mL) and extracted with DCM (2 mL). The combined organic extracts were concentrated in vacuo to give the crude residue. Purification by AP3 gave 3 mg (17%) of the title compound. AP3 Rf=3.5. LRMS: EI⁺ m/z 647 [MH⁺].

Example 59

1-{[(3S,4R)-1-tert-butyl-4-(2,4-difluorophenyl)pyrrolidin-3-yl]carbonyl}-5S-(4-chlorophenyl)-4-(tetrahydro-2H-pyran-4-ylcarbonyl)-1,4-diazocane

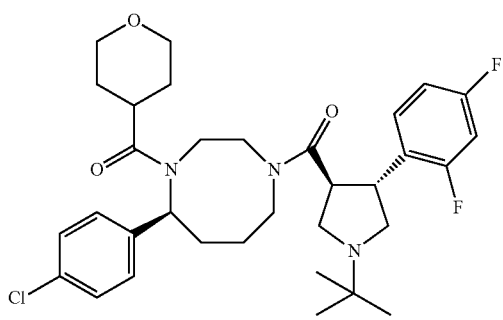 [SMILES: CC(C)(C)N1C[C@@H](C(=O)N2CCC[C@@H](c3ccc(Cl)cc3)N(C(=O)C3CCOCC3)CC2)[C@H](c2ccc(F)cc2F)C1]

To a solution of the compound of preparation 70 (30 mg, 0.061 mmol) in DCM (10 mL) were added triethylamine (43 µL, 0.43 mmol), 2-chloro-1,3-dimethylimidazolinium chloride (21 mg, 0.122 mmol) and tetrahydro-2H-pyran-4-carboxylic acid (40 mg, 0.31 mmol). The reaction mixture was stirred at RT for 48 h. The reaction was diluted by adding sodium hydrogen carbonate solution (2 mL) and partitioned organic extracts were concentrated in vacuo to give the crude residue. Purification by AP3 gave 15 mg (41% yield) of the title compound (rf 3.43). LRMS: APCl⁺ m/z 602 [MH⁺].

Example 60

1-{[(3S,4R)-1-tert-butyl-4-(2,4-difluorophenyl)pyrrolidin-3-yl]carbonyl}-5S-(4-chlorophenyl)-4-(1-methylcyclopropylcarbonyl)-1,4-diazocane

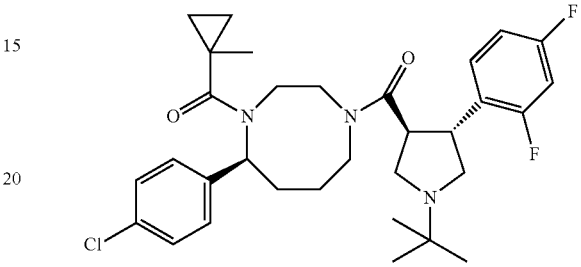

This compound was prepared by the method of example 59 using the appropriate carboxylic acid and the compound of preparation 70. Purification by AP3 gave 16.69 mg of the title compound (rf 3.66). LRMS: APCl⁺ m/z 572 [MH⁺].

Example 61

1-{[(3S,4R)-1-tert-butyl-4-(2,4-difluorophenyl)pyrrolidin-3-yl]carbonyl}-5S-4-chlorophenyl)-4-[(3,3-difluorocyclobutyl)carbonyl]-1,4-diazocane

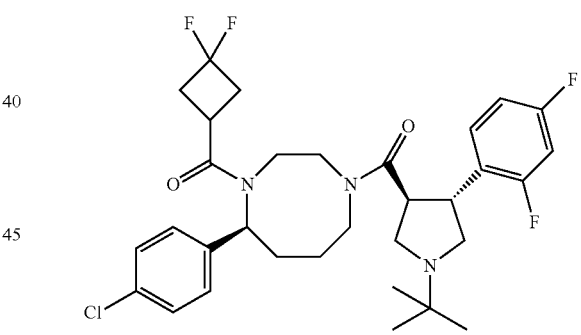

To a solution of the compound of preparation 70 (30 mg, 0.061 mmol) in DCM (10 mL) were added triethylamine (34 µL, 0.25 mmol), PS-Mukaiyama reagent (144 mg, 0.122 mmol) and 3,3-difluorocyclobutanecarboxylic acid (8 mg, 0.061 mmol). The reaction mixture was stirred at RT for 24 h. The reaction was filtered, and filtrate concentrated in vacuo. The residue was diluted by adding sodium hydrogen carbonate solution (15 mL) and extracted with EtOAc (3×15 mL). The combined organic extracts were concentrated in vacuo to give the crude residue which was purified by AP3 (rf 2.74) to obtain 1.6 mg (4% yield) of the title compound. LRMS: APCl⁺ m/z 608 [MH⁺].

Examples 62-65

These compounds were prepared by the method of example 61 using the appropriate carboxylic acid and precursor as listed in the table.

| Example | Structure | MS MH+ ion | AP3 Rf | Precursor (Prep #) |
|---|---|---|---|---|
| 62[B] | 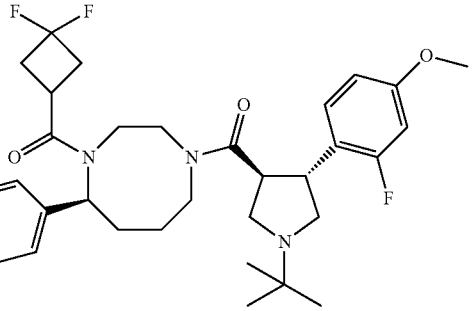 | 620 | 3.75 | 89 |
| 63[B] | 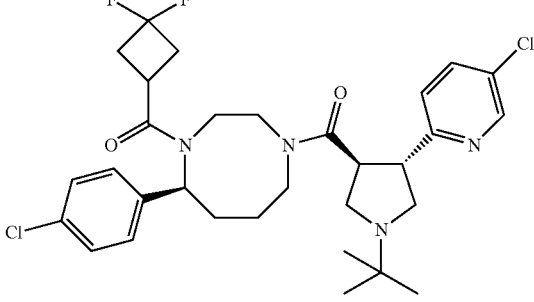 | 607 | 2.68 | 88 |
| 64[B] | 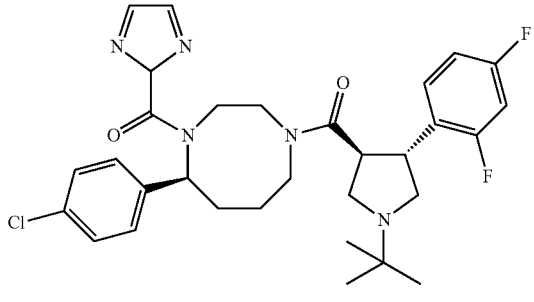 [SMILES: CC(C)(C)N1C[C@@H](C(=O)N2CCC[C@@H](c3ccc(Cl)cc3)N(C(=O)C3N=CC=N3)CC2)[C@H](c2ccc(F)cc2F)C1] | 584 | 2.66 | 70 |
| 65[B] | 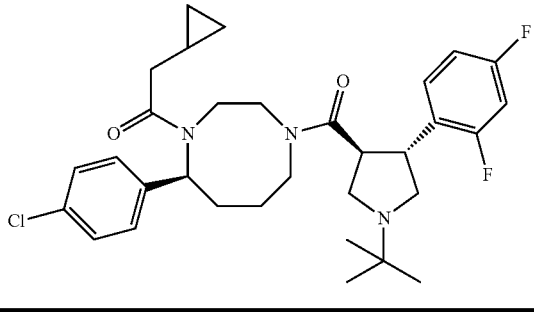 | 572 | 2.69 | 70 |
B = single epimer Examples 66-105 were prepared according to scheme 3

Example 66 methyl (8S-4-chlorophenyl)-4-{[(3S,4R)-4-(2,4-difluorophenyl)-1-(1-methyl-6-oxo-1,6-dihydropyridazin-3-yl)pyrrolidin-3-yl]carbonyl}-1,4-diazocane-1-carboxylate

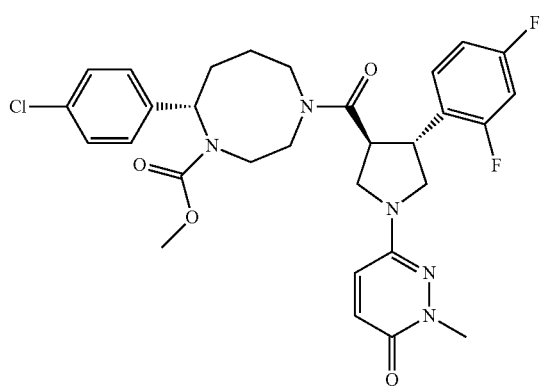 [SMILES: COC(=O)N1CCN(C(=O)[C@@H]2CN(c3ccc(=O)n(C)n3)C[C@H]2c2ccc(F)cc2F)CCC[C@H]1c1ccc(Cl)cc1]

To a suspension of the compound of preparation 60 (200 mg, 0.470 mmol) in DCM (6 mL) were added triethylamine (197 μL, 1.41 mmol), 1-hydroxybenzotriazole monohydrate (83 mg, 0.542 mmol) and EDCl (113 mg, 0.589 mmol). The reaction mixture was stirred at RT for 30 min. The compound of preparation 15a was then added and the reaction mixture was stirred at RT for 16 h. The reaction was concentrated in vacuo and residue partitioned between EtOAc (20 mL) and citric acid solution (10 mL). The organic layer was separated, washed with sodium hydrogen carbonate solution (10 mL), dried over magnesium sulphate and concentrated in vacuo to give the crude residue. Purification by column chromatography on silica gel using dichloromethane:methanol:0.88 ammonia (gradient from pure dichloromethane to 95:5:0.5) gave 234 mg (83%) of the title compound as a yellow foam.

$^1$H NMR (400 MHz, CD$_3$OD) δ 0.95-1.10 (1H, m), 1.45-1.60 (1H, m), 1.65-1.75 (1H, m), 1.90-2.05 (1H, m), 2.10-2.25 (1H, m), 2.35-2.50 (1H, m), 2.85-3.05 (1H, m), 3.30-4.10 (15H, m), 4.95-5.15 (1H, dd), 7.10-7.35 (4H, m), 6.95-7.05 (4H, m), 7.40-7.50 (1H, m). LRMS: EI$^+$ m/z 600 [MH$^+$].

Examples 67-97

These compounds were prepared by the method of example 66 using the appropriate carboxylic acid and precursors as listed in the table.

| Example | Structure | MS MH+ ion | AP3 Rf | Precursors (Prep #) |
|---|---|---|---|---|
| 67[B] | | 591 | 3.37 | 58 and 22b |
| 68[B] | | 582 | 3.04 | 55 and 22b |

-continued

| Example | Structure | MS MH+ ion | AP3 Rf | Precursors (Prep #) |
|---|---|---|---|---|
| 69[B] | 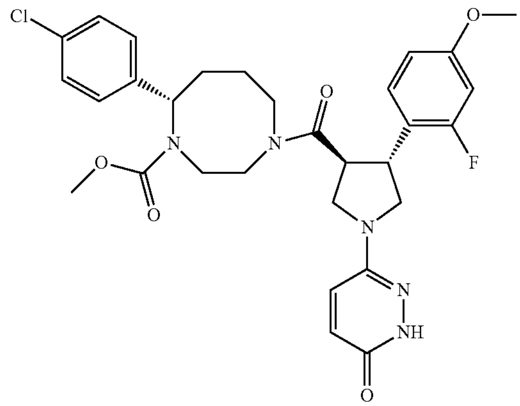 [SMILES: COC(=O)N1CCN(C(=O)[C@@H]2CN(c3ccc(=O)[nH]n3)C[C@H]2c2ccc(OC)cc2F)CCC[C@H]1c1ccc(Cl)cc1] | 598 | — | 55 and 15a |
| 70[B] | 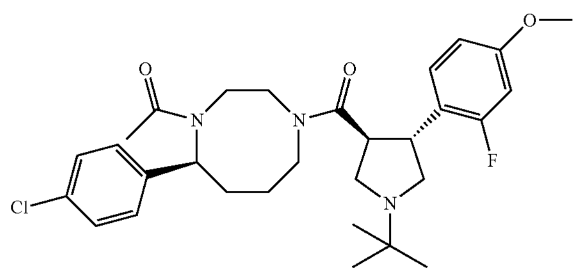 [SMILES: COc1ccc([C@@H]2CN(C(C)(C)C)C[C@H]2C(=O)N2CCC[C@@H](c3ccc(Cl)cc3)N(C(C)=O)CC2)c(F)c1] | 544 | 2.6 | 57 and 22b |
| 71[B] | 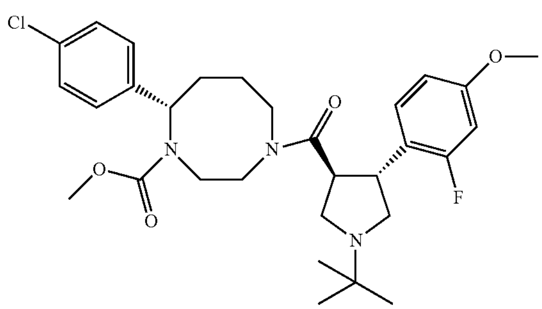 [SMILES: COC(=O)N1CCN(C(=O)[C@@H]2CN(C(C)(C)C)C[C@H]2c2ccc(OC)cc2F)CCC[C@H]1c1ccc(Cl)cc1] | 560 | 3.7 | 57 and 15a |
| 72[B] | 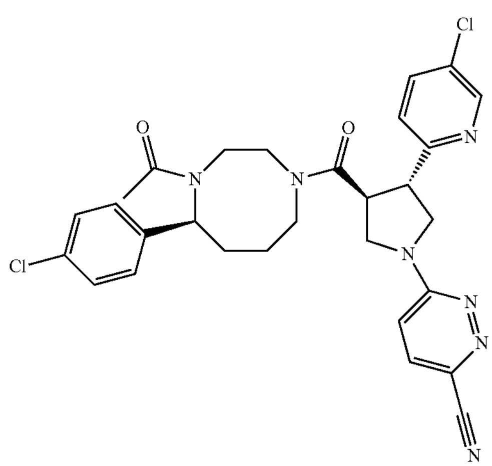 [SMILES: CC(=O)N1CCN(C(=O)[C@@H]2CN(c3ccc(C#N)nn3)C[C@H]2c2ccc(Cl)cn2)CCC[C@H]1c1ccc(Cl)cc1] | 578 | 3.42 | 65 and 22b |

-continued
| Example | Structure | MS MH+ ion | AP3 Rf | Precursors (Prep #) |
|---|---|---|---|---|
| 73[A] | 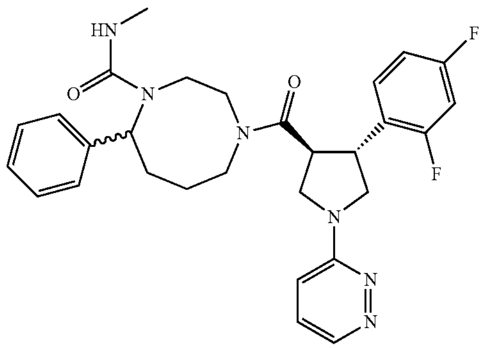 [SMILES: CNC(=O)N1CCN(C(=O)[C@@H]2CN(c3cccnn3)C[C@H]2c2ccc(F)cc2F)CCCC1c1ccccc1] | 535 | — | 98 and 23 |
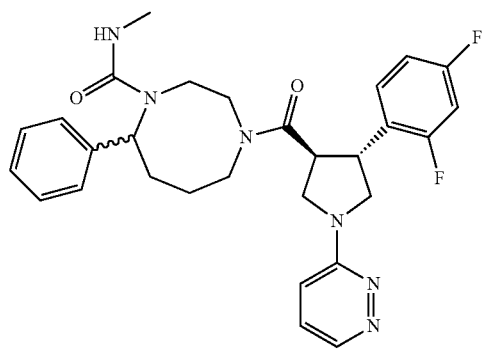
| | | | | |
|---|---|---|---|---|
| 74[A] | | 542 | — | 99 and 20 |
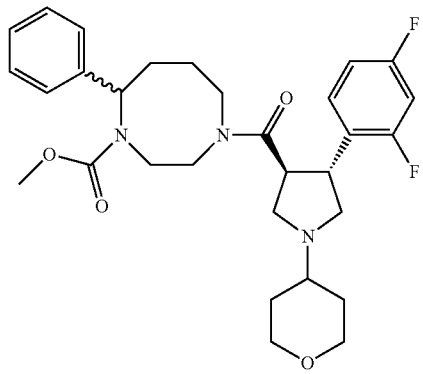 [SMILES: COC(=O)N1CCN(C(=O)[C@@H]2CN(C3CCOCC3)C[C@H]2c2ccc(F)cc2F)CCCC1c1ccccc1]
| | | | | |
|---|---|---|---|---|
| 75[A] | | 595 | — | 52 and 15 |
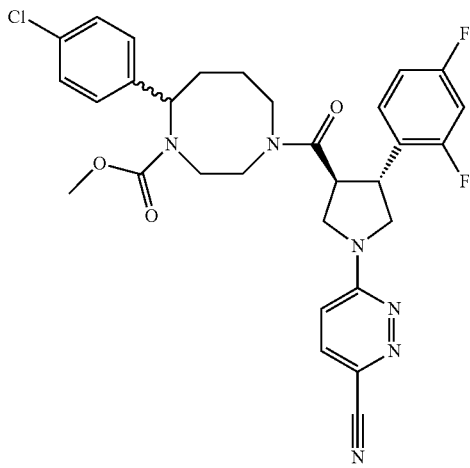 [SMILES: COC(=O)N1CCN(C(=O)[C@@H]2CN(c3ccc(C#N)nn3)C[C@H]2c2ccc(F)cc2F)CCCC1c1ccc(Cl)cc1]

-continued
| Example | Structure | MS MH+ ion | AP3 Rf | Precursors (Prep #) |
|---|---|---|---|---|
| 76[A] | 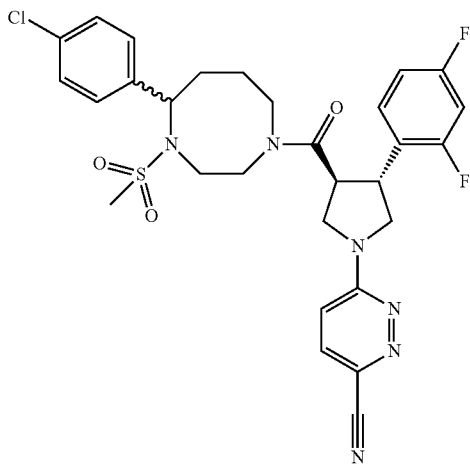 [SMILES: CS(=O)(=O)N1CCN(C(=O)[C@@H]2CN(c3ccc(C#N)nn3)C[C@H]2c2ccc(F)cc2F)CCCC1c1ccc(Cl)cc1] | 615 | — | 52 and 17 |
| 77[A] | 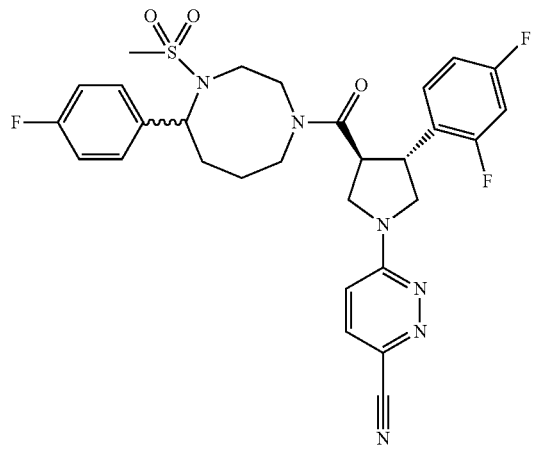 [SMILES: CS(=O)(=O)N1CCN(C(=O)[C@@H]2CN(c3ccc(C#N)nn3)C[C@H]2c2ccc(F)cc2F)CCCC1c1ccc(F)cc1] | 599 | — | 52 and 18 |
| 78[A] | 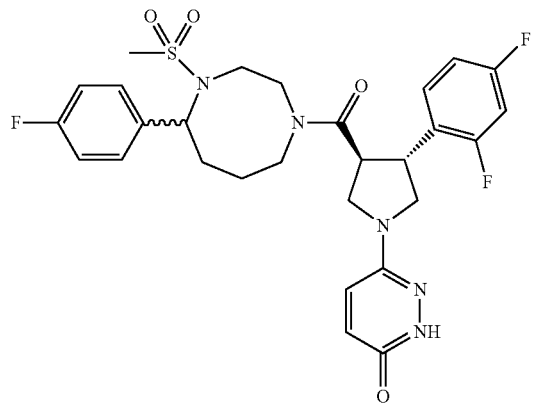 | 590 | — | 62 and 18 |

-continued
| Example | Structure | MS MH+ ion | AP3 Rf | Precursors (Prep #) |
|---|---|---|---|---|
| 79[A] | 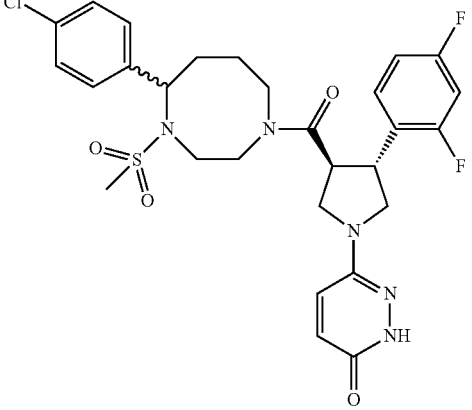 | 606 | — | 62 and 17 |
| 80[A] | 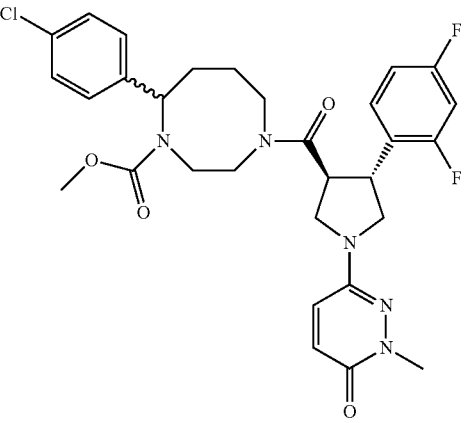 [SMILES: COC(=O)N1CCN(C(=O)[C@@H]2CN(c3ccc(=O)n(C)n3)C[C@H]2c2ccc(F)cc2F)CCCC1c1ccc(Cl)cc1] | 600 | — | 60 and 15 |
| 81[A] | 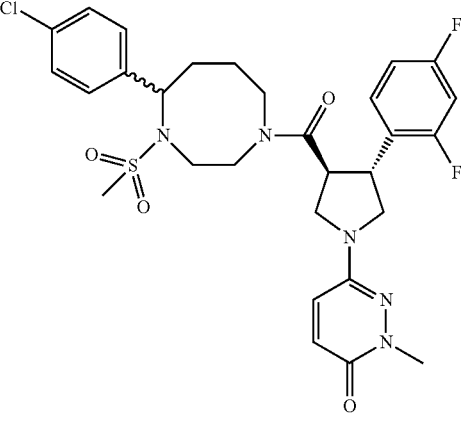 [SMILES: Cn1nc(N2C[C@@H](C(=O)N3CCCC(c4ccc(Cl)cc4)N(S(C)(=O)=O)CC3)[C@H](c3ccc(F)cc3F)C2)ccc1=O] | 620 | — | 60 and 17 |
| 82[A] | 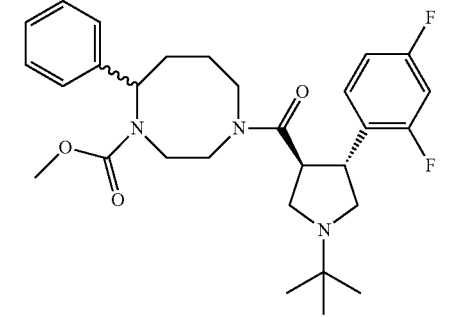 [SMILES: COC(=O)N1CCN(C(=O)[C@@H]2CN(C(C)(C)C)C[C@H]2c2ccc(F)cc2F)CCCC1c1ccccc1] | 514 | — | 100 and 20 |

-continued

| Example | Structure | MS MH+ ion | AP3 Rf | Precursors (Prep #) |
|---------|-----------|------------|--------|---------------------|
| 83[A] | 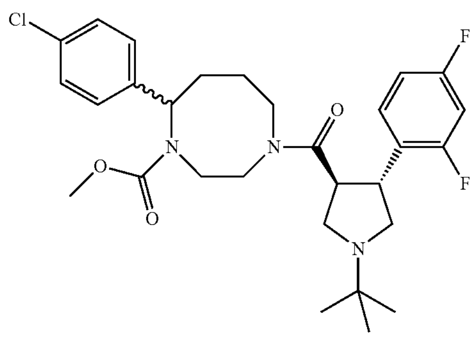 [SMILES: COC(=O)N1CCN(C(=O)[C@@H]2CN(C(C)(C)C)C[C@H]2c2ccc(F)cc2F)CCCC1c1ccc(Cl)cc1] | 548 | — | 100 and 15 |
| 84[A] | 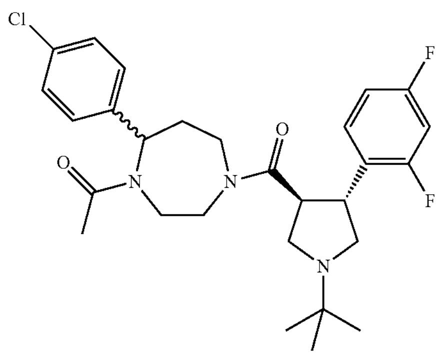 [SMILES: CC(=O)N1CCN(C(=O)[C@@H]2CN(C(C)(C)C)C[C@H]2c2ccc(F)cc2F)CCC1c1ccc(Cl)cc1] | 518 | 2.45 | 100 and 26 |
| 85[A] | 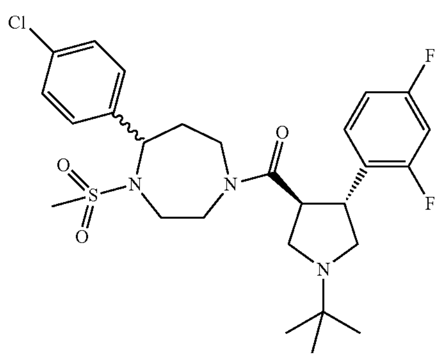 [SMILES: CC(C)(C)N1C[C@@H](C(=O)N2CCC(c3ccc(Cl)cc3)N(S(C)(=O)=O)CC2)[C@H](c2ccc(F)cc2F)C1] | 554 | 2.55 | 100 and 24 |
| 86[A] | 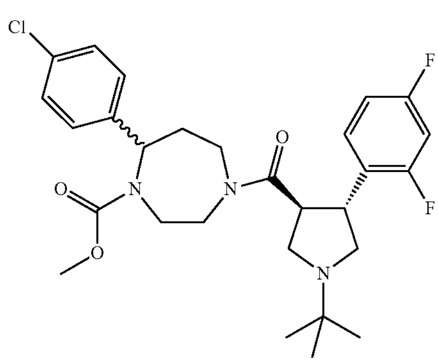 [SMILES: COC(=O)N1CCN(C(=O)[C@@H]2CN(C(C)(C)C)C[C@H]2c2ccc(F)cc2F)CCC1c1ccc(Cl)cc1] | 534 | 2.66 | 100 and 25 |

-continued

| Example | Structure | MS MH+ ion | AP3 Rf | Precursors (Prep #) |
|---|---|---|---|---|
| 87[A] | 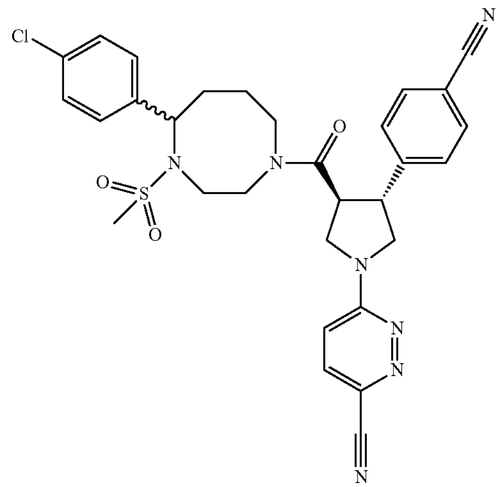 [SMILES: CS(=O)(=O)N1CCN(C(=O)[C@@H]2CN(c3ccc(C#N)nn3)C[C@H]2c2ccc(C#N)cc2)CCCC1c1ccc(Cl)cc1] | 604 | — | 64 and 17 |
| 88[B] | 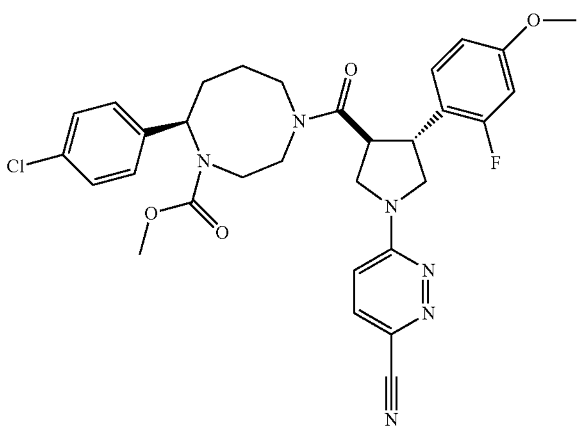 | 607 | 3.76 | 58 and 15b |
| 89[B] | 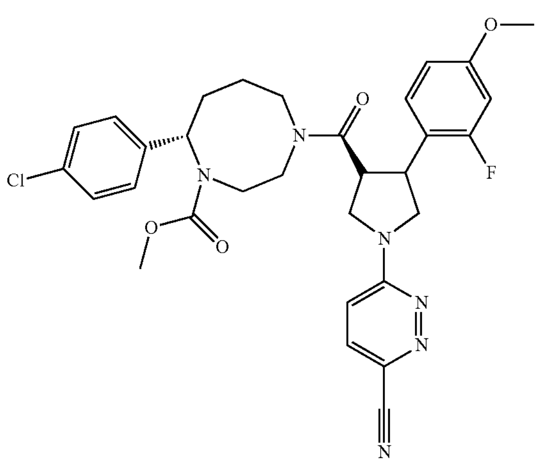 | 607 | 3.79 | 58 and 15a |

-continued

| Example | Structure | MS MH+ ion | AP3 Rf | Precursors (Prep #) |
|---|---|---|---|---|
| 90[B] | 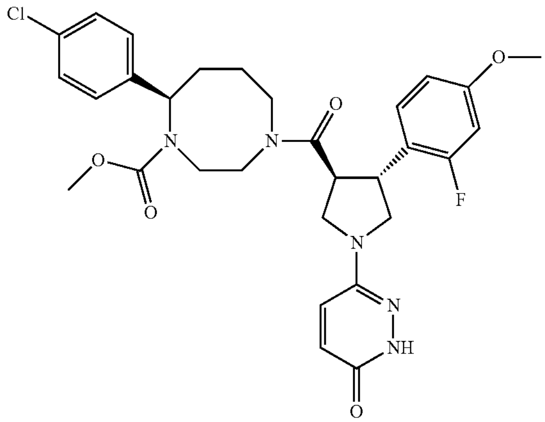 [SMILES: COC(=O)N1CCN(C(=O)[C@@H]2CN(c3ccc(=O)[nH]n3)C[C@H]2c2ccc(OC)cc2F)CCC[C@@H]1c1ccc(Cl)cc1] | 598 | — | 55 and 15b |
| 91[B] | 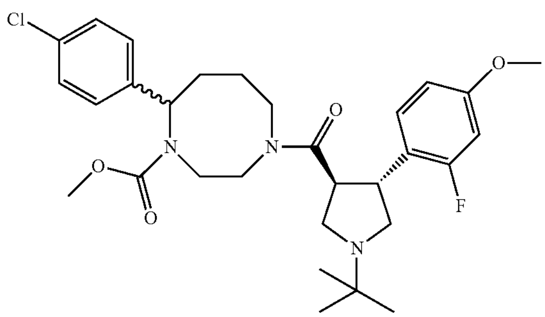 [SMILES: COC(=O)N1CCN(C(=O)[C@@H]2CN(C(C)(C)C)C[C@H]2c2ccc(OC)cc2F)CCCC1c1ccc(Cl)cc1] | 560 | 2.53 | 57 and 15a |
| 92[A] | 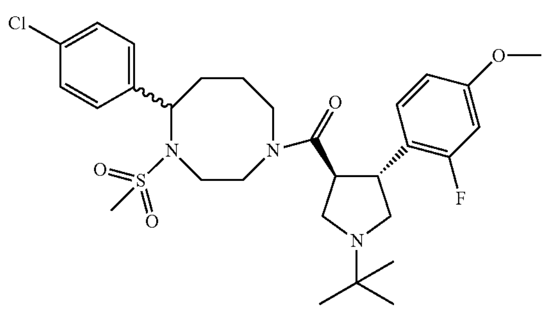 [SMILES: COc1ccc([C@@H]2CN(C(C)(C)C)C[C@H]2C(=O)N2CCCC(c3ccc(Cl)cc3)N(S(C)(=O)=O)CC2)c(F)c1] | 580 | — | 57 and 17 |
| 93[A] | 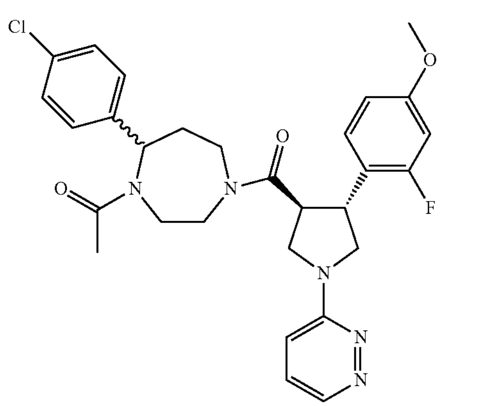 [SMILES: COc1ccc([C@@H]2CN(c3cccnn3)C[C@H]2C(=O)N2CCC(c3ccc(Cl)cc3)N(C(C)=O)CC2)c(F)c1] | 552 | 2.59 | 63 and 26 |

| Example | Structure | MS MH+ ion | AP3 Rf | Precursors (Prep #) |
|---|---|---|---|---|
| 94[A] | 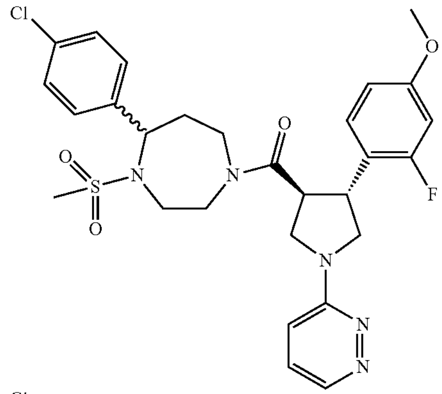 | 588 | 2.63 | 63 and 24 |
| 95[A] | 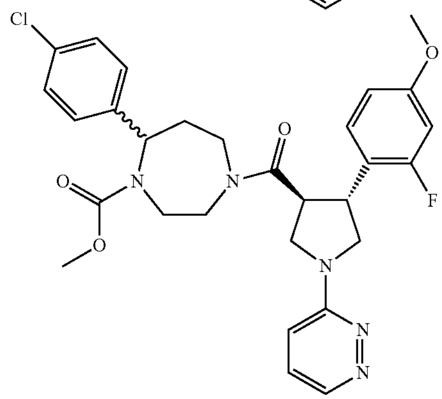 | 568 | 2.69 | 63 and 25 |
| 96[B] | 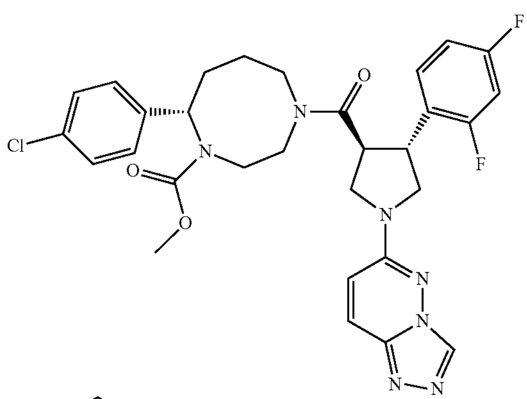 [SMILES: COC(=O)N1CCN(C(=O)[C@@H]2CN(c3ccc4nncn4n3)C[C@H]2c2ccc(F)cc2F)CCC[C@H]1c1ccc(Cl)cc1] | 610 | — | 61 and 15a |
| 97[A] | 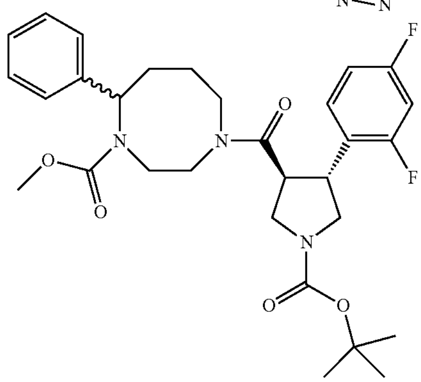 | 558 | — | 101 and 20 |

A = mixture of epimers;
B = single epimer

Example 98 methyl 8S-(4-chlorophenyl)-4-{[(3S,4S)-4-(5-chloropyridin-2-yl)-1-(6-cyanopyridazin-3-yl)pyrrolidin-3-yl]carbonyl}-1,4-diazocane-1-carboxylate

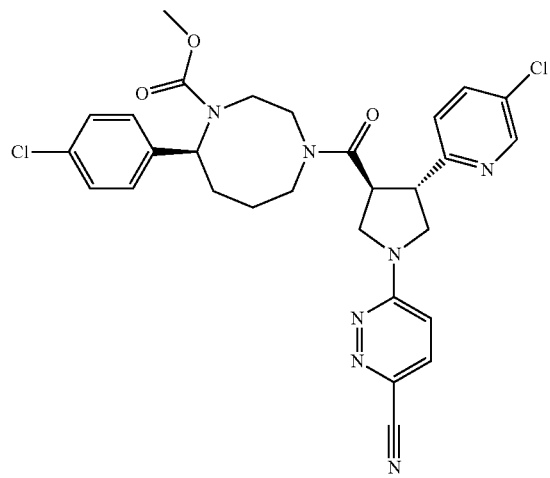 [SMILES: COC(=O)N1CCN(C(=O)[C@@H]2CN(c3ccc(C#N)nn3)C[C@H]2c2ccc(Cl)cn2)CCC[C@H]1c1ccc(Cl)cc1]

To a solution of the compound of preparation 65 (24 mg, 0.075 mmol) in DCM (3 mL) were added diisopropylethylamine (79 µL, 0.46 mmol), HBTU (47 mg, 0.13 mmol) and the compound of preparation 15a (40 mg, 0.13 mmol). The reaction mixture was stirred at RT for 24 h then diluted by adding sodium hydrogen carbonate solution (2 mL). The separated organic extracts were concentrated in vacuo to give the crude residue which was purified by AP3 (rf 3.67) to obtain 42 mg (64% yield) of the title compound. LRMS: APCl$^+$ m/z 594 [MH$^+$].

Examples 99-105

These compounds were prepared by the method of example 98 starting from the appropriate precursors as listed in the table.

| Example | Structure | MS MH+ ion | AP3 Rf | Precursors (Prep #) |
|---|---|---|---|---|
| 99[A] | 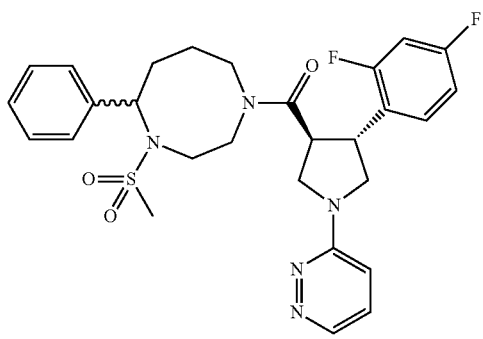 [SMILES: CS(=O)(=O)N1CCN(C(=O)[C@@H]2CN(c3cccnn3)C[C@H]2c2ccc(F)cc2F)CCCC1c1ccccc1] | 553 | — | 98 and 19 |
| 100[A] | 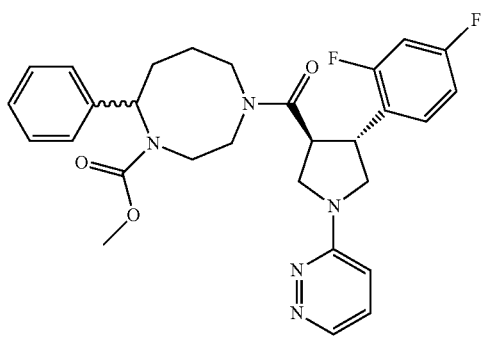 [SMILES: COC(=O)N1CCN(C(=O)[C@@H]2CN(c3cccnn3)C[C@H]2c2ccc(F)cc2F)CCCC1c1ccccc1] | 536 | — | 98 and 20 |

-continued
| Example | Structure | MS MH+ ion | AP3 Rf | Precursors (Prep #) |
|---|---|---|---|---|
| 101[A] | 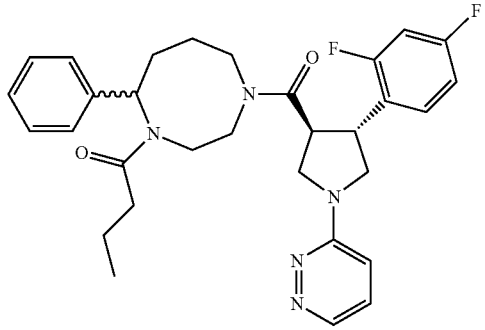 [SMILES: CCCC(=O)N1CCN(C(=O)[C@@H]2CN(c3cccnn3)C[C@H]2c2ccc(F)cc2F)CCCC1c1ccccc1] | 548 | — | 98 and 21 |
| 102[B] | 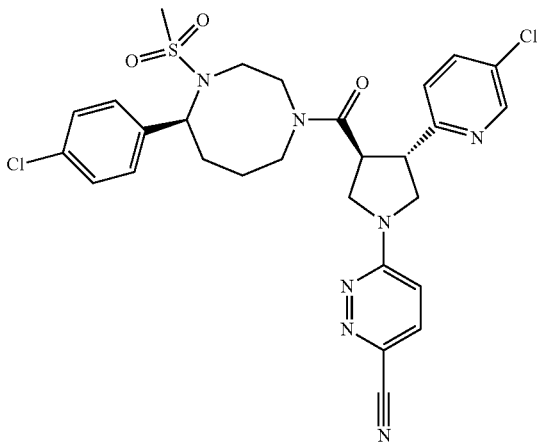 [SMILES: CS(=O)(=O)N1CCN(C(=O)[C@@H]2CN(c3ccc(C#N)nn3)C[C@H]2c2ccc(Cl)cn2)CCC[C@H]1c1ccc(Cl)cc1] | 614 | 3.65 | 65 and 17a |
| 103[A] | 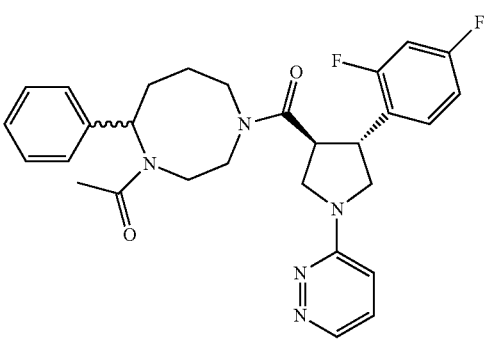 [SMILES: CC(=O)N1CCN(C(=O)[C@@H]2CN(c3cccnn3)C[C@H]2c2ccc(F)cc2F)CCCC1c1ccccc1] | 520 | — | 98 and 22 |
[A] = mixture of epimers;
[B] = single epimer

Example 104

1-{[(3S,4R)-1-tert-butyl-4-(2,4-difluorophenyl)pyrrolidin-3-yl]carbonyl}-4-butyryl-5-phenyl-1,4-diazocane

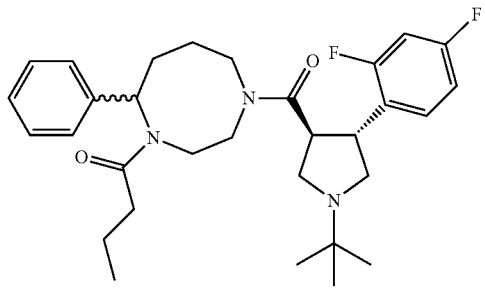 [SMILES: CCCC(=O)N1CCN(C(=O)[C@@H]2CN(C(C)(C)C)C[C@H]2c2ccc(F)cc2F)CCCC1c1ccccc1]

To a solution of the compound of preparation 100 (24 mg, 0.075 mmol) in dimethylacetamide (1.25 mL) were added triethylamine (42 μL, 0.30 mmol), TBTU (24 mg, 0.075 mmol) and the compound of preparation 21 (12 mg, 0.050 mmol). The reaction mixture was shaken at 60° C. for 24 h. The reaction mixture was concentrated in vacuo to give the crude residue. Purification by AP3 (rf 3.68) gave 7 mg (27% yield) of the title compound as a mixture of epimers. LRMS: APCI$^+$ m/z 526 [MH$^+$].

Examples 105-108 were prepared according to scheme 4.

Example 105

6-[(3S,4R)-3-{[5-(4-chlorophenyl)-4-(methylsulfonyl)-1,4-diazocan-1-yl]carbonyl}-4-(2-fluoro-4-methoxyphenyl)pyrrolidin-1-yl]pyridazine-3-carbonitrile

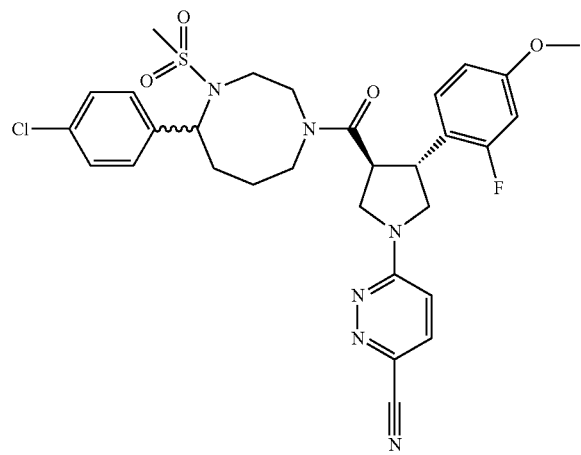 [SMILES: COc1ccc([C@@H]2CN(c3ccc(C#N)nn3)C[C@H]2C(=O)N2CCCC(c3ccc(Cl)cc3)N(S(C)(=O)=O)CC2)c(F)c1]

To a solution of the compound of preparation 92 (30 mg, 0.057 mmol) in acetonitrile (10 mL) were added 3-chloro-6-cyanopyridazine (12 mg, 0.086 mmol) and N,N-diisopropylethylamine (40 μL, 0.23 mmol). The reaction mixture was stirred at reflux for 3 h. The reaction was concentrated in vacuo and residue diluted by adding sodium hydrogen carbonate solution (10 mL) and extracted with EtOAc (3×10 mL). The combined organic extracts were washed with brine (15 mL), dried with sodium sulphate, filtered and concentrated in vacuo to give the crude residue. Purification by column chromatography on silica gel using dichloromethane:methanol:0.88 ammonia (95:5:0.5) gave 25 mg (78%) of the title compound as a mixture of epimers as a white solid.

$^1$H NMR (400 MHz, CD$_3$OD) δ 1.19-2.47 (10H, m), 2.87-4.49 (12H, m), 4.80-4.85 (1H, m), 6.52-6.69 (3H, m), 6.92-6.94 (2H, m), 7.09-7.37 (3H, m), 7.42-7.47 (1H, m). LRMS: APCI$^+$ m/z 627 [MH$^+$].

Example 106 methyl 8-(4-chlorophenyl)-4-{[(3S,4S)-4-(2-fluoro-4-methoxyphenyl)-1-(6-cyanopyridazin-3-yl)pyrrolidin-3-yl]carbonyl}-1,4-diazocane-1-carboxylate

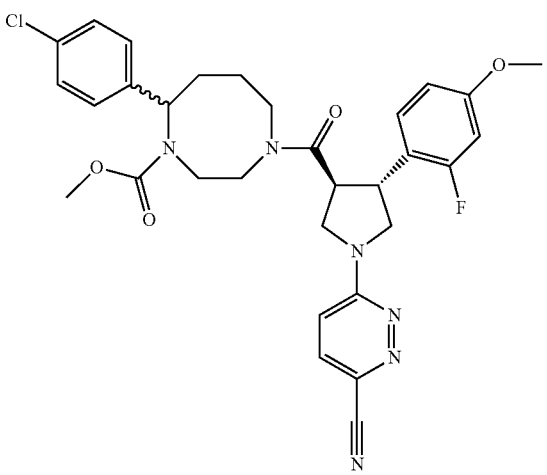 [SMILES: COC(=O)N1CCN(C(=O)[C@@H]2CN(c3ccc(C#N)nn3)C[C@H]2c2ccc(OC)cc2F)CCCC1c1ccc(Cl)cc1]

This compound was prepared by the method of example 105 but starting from 3-chloro-6-cyanopyridazine and the compound of preparation 93. LRMS: APCI$^+$ m/z 607 [MH$^+$].

Example 107

Methyl 8-(4-chlorophenyl)-4-{[(3S,4R)-1-(6-chloropyridazin-3-yl)-4-(2-fluoro-4-methoxyphenyl)pyrrolidin-3-yl]carbonyl}-1,4-diazocane-1-carboxylate

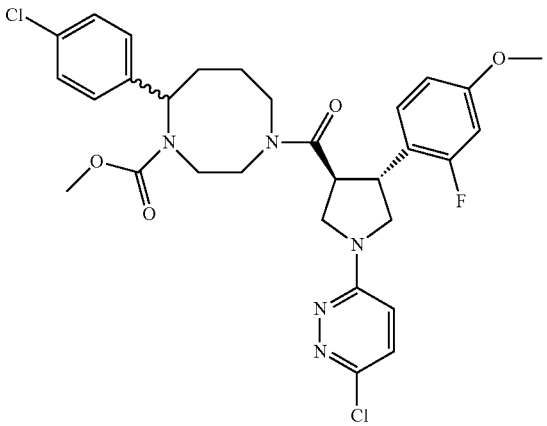 [SMILES: COC(=O)N1CCN(C(=O)[C@@H]2CN(c3ccc(Cl)nn3)C[C@H]2c2ccc(OC)cc2F)CCCC1c1ccc(Cl)cc1]

To a solution of the compound of preparation 93 (65 mg, 0.13 mmol) in dimethylsulfoxide (2 mL) were added 3,6-dichloropyridazine (58 mg, 0.39 mmol), caesium fluoride (20 mg, 0.13 mmol) and triethylamine (54 μL, 0.39 mmol). The reaction mixture was stirred at reflux for 24 h then cooled to RT over 40 h. The reaction was diluted with sodium hydrogen carbonate solution (30 mL) and extracted with diethylether (4×20 mL). The combined organic extracts were washed with brine (3×25 mL) and concentrated in vacuo to give the crude residue. Purification by column chromatography on silica gel using dichloromethane:methanol:0.88 ammonia (98:2:0.2) gave 73 mg (92%) of the title compound as a mixture of epimers as an off white foam.

$^1$H NMR (400 MHz, CD$_3$OD) δ 0.92-2.33 (5H, m), 2.56-3.76 (14H, m), 3.85-4.36 (3H, m), 4.85-5.20 (1H, m), 6.40-6.64 (3H, m), 6.77-6.89 (1H, m), 6.99-7.25 (5H, m). LRMS: APCl$^+$ m/z 616 [MH$^+$].

Example 108

[5-(4-chlorophenyl)-4-(methylsulfonyl)-1,4-diazocan-1-yl]-[(3S,4R)-1-(6-chloro-pyridazine-3-yl)-4-(2-fluoro-4-methoxyphenyl)-pyrrolidin-3-yl]-methanone

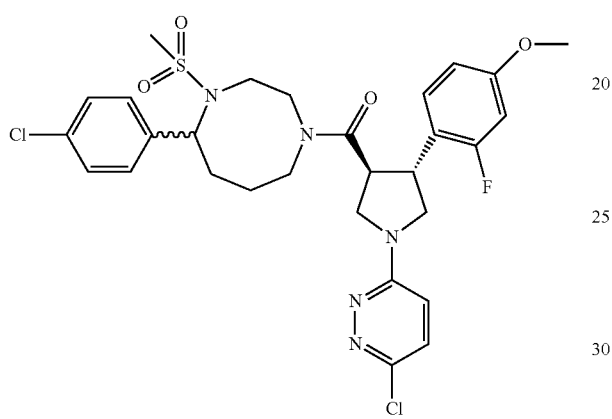

This compound was prepared by the method of example 107 but starting from 3,6-dichloropyridazine and the compound of preparation 92. LRMS: APCl$^+$ m/z 636 [MH$^+$].

Examples 109-110

These compounds were prepared by the method of example 107 using 3,6-dichloropyridazine and the appropriate precursor as listed in the table.

| Example | Structure | MS MH+ ion | Precursor (Prep #) |
|---|---|---|---|
| 109$^C$ | 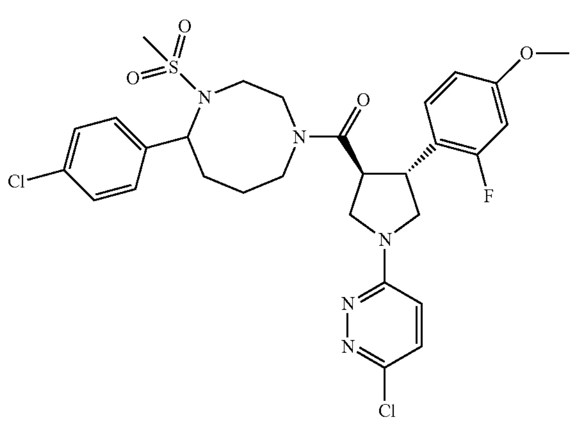 [SMILES: COc1ccc([C@@H]2CN(c3ccc(Cl)nn3)C[C@H]2C(=O)N2CCCC(c3ccc(Cl)cc3)N(S(C)(=O)=O)CC2)c(F)c1] | 636 | 94 |

| Example | Structure | MS MH+ ion | Precursor (Prep #) |
|---|---|---|---|
| 110[D] | 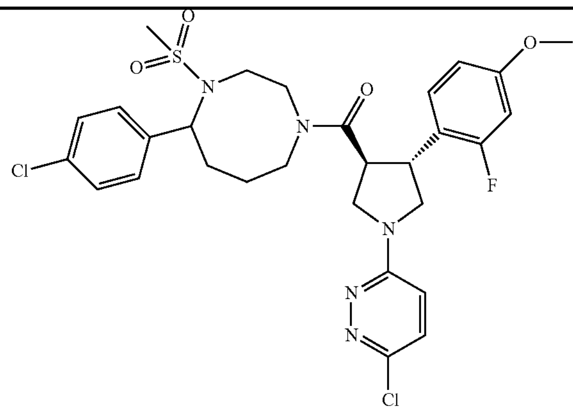 | 636 | 95 |

C = single epimer of unknown absolute configuration at site of chloro-phenyl substitution;
D = single epimer of opposite configuration at site of chloro-phenyl substitution with respect to compound of example 109

Examples 111-114 were prepared according to scheme 5.

Example 111

6-[(3S,4R)-3-{[5-(4-chlorophenyl)-4-(methylsulfonyl)-1,4-diazocan-1-yl]carbonyl}-4-(2-fluoro-4-methoxyphenyl)pyrrolidin-1-yl]pyridazin-3(2H)-one

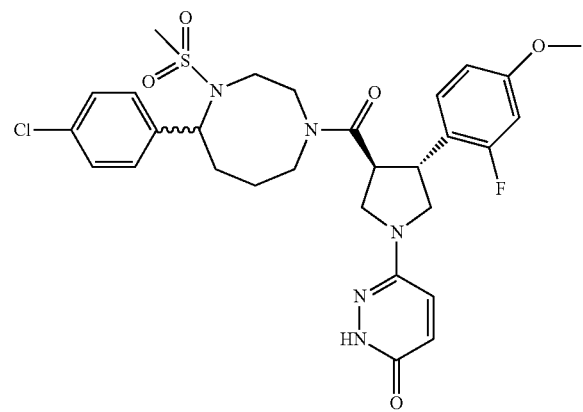 [SMILES: COc1ccc([C@@H]2CN(c3ccc(=O)[nH]n3)C[C@H]2C(=O)N2CCCC(c3ccc(Cl)cc3)N(S(C)(=O)=O)CC2)c(F)c1]

The compound of example 108 (100 mg, 0.157 mmol) was dissolved in acetic acid (5 mL). The resulting solution was thoroughly degassed and stirred at reflux under nitrogen overnight. The reaction was concentrated in vacuo and residue diluted by adding sodium hydrogen carbonate solution (25 mL) and extracted with EtOAc (3×25 mL). The combined organic extracts were washed with sodium hydrogen carbonate solution (30 mL), brine (30 mL), dried with sodium sulphate, filtered and concentrated in vacuo to give the crude residue. Purification by column chromatography on silica gel using dichloromethane:methanol:0.88 ammonia (92.5:7.5:0.75) gave 90 mg (93%) of the title compound as a mixture of epimers as an off white foam.

$^1$H NMR (400 MHz, CD$_3$OD) δ 1.09-2.53 (8H, m), 2.91-3.23 (1H, m), 3.34-4.38 (14H, m), 6.60-6.77 (2H, m), 6.83-7.09 (2H, m), 7.26-7.40 (5H, m). LRMS: APCl$^+$ m/z 618 [MH$^+$].

Examples 112-114

These compounds were prepared by the method of example 111 starting from the appropriate precursor as listed in the table.

| Example | Structure | MS MH+ ion | Precursor (example #) |
|---|---|---|---|
| 112[A] | 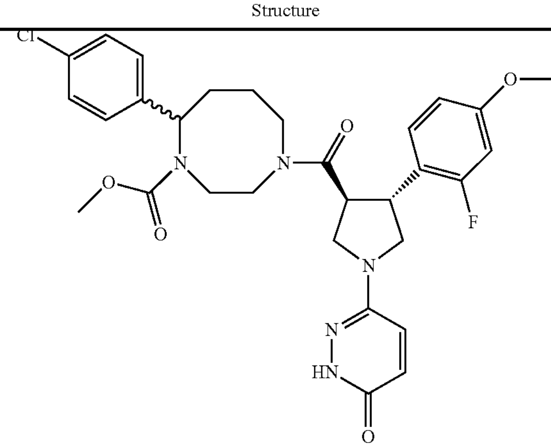 | 598 | 107 |

-continued

| Example | Structure | MS MH+ ion | Precursor (example #) |
|---|---|---|---|
| 113[D] | 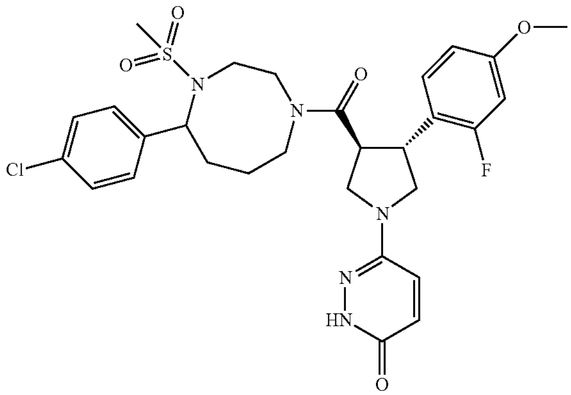 [SMILES: COc1ccc([C@@H]2CN(c3ccc(=O)[nH]n3)C[C@H]2C(=O)N2CCCC(c3ccc(Cl)cc3)N(S(C)(=O)=O)CC2)c(F)c1] | 618 | 109 |
| 114[E] | 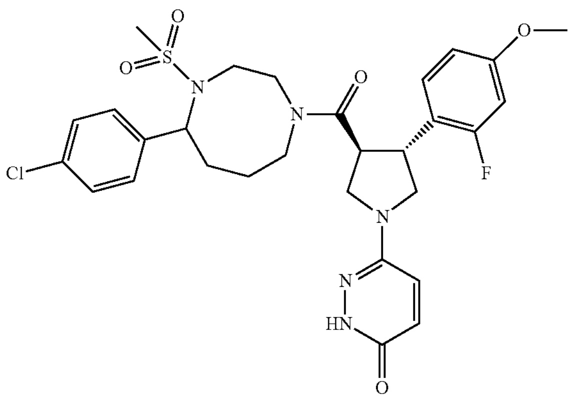 [SMILES: COc1ccc([C@@H]2CN(c3ccc(=O)[nH]n3)C[C@H]2C(=O)N2CCCC(c3ccc(Cl)cc3)N(S(C)(=O)=O)CC2)c(F)c1] | 618 | 110 |

[A] = mixture of epimers;
[D] = single epimer of unknown absolute configuration at site of chlorophenyl substitution;
[E] = single epimer of opposite configuration at chlorophenyl substituent site with respect to example 113

Examples 115-119 were prepared according to scheme 6.

Example 115

6-[(3S,4R)-3-{[5-(4-chlorophenyl)-4-(methylsulfonyl)-1,4-diazocan-1-yl]carbonyl}-4-(2-fluoro-4-methoxyphenyl)pyrrolidin-1-yl]-2-methylpyridazin-3(2H)-one

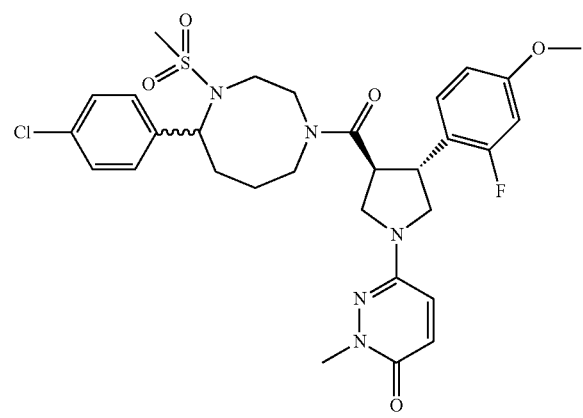 [SMILES: COc1ccc([C@@H]2CN(c3ccc(=O)n(C)n3)C[C@H]2C(=O)N2CCCC(c3ccc(Cl)cc3)N(S(C)(=O)=O)CC2)c(F)c1]

To a solution of the compound of example 111 (45 mg, 0.073 mmol) in DMF (2 mL) were added lithium bromide (7.6 mg, 0.087 mmol), and sodium hexamethyldisilazide (16 mg, 0.087 mmol). The reaction mixture was stirred at RT for 30 min. Methyl iodide (5.4 µL, 0.087 mmol) was added and the resulting solution stirred at RT for 24 h. The reaction was concentrated in vacuo, the residue was diluted by adding sodium hydrogen carbonate solution (20 mL) and extracted with ethyl acetate (4×20 mL). The combined organic extracts were washed with brine (20 mL), and concentrated in vacuo to give the crude residue. Purification by column chromatography on silica gel using dichloromethane:methanol:0.88 ammonia (95:5:0.5) gave 46 mg (59%) of the title compound as a mixture of epimers as a foam.

$^1$H NMR (400 MHz, CD$_3$OD) δ 1.09-1.34 (2H, m), 1.43-2.53 (6H, m), 2.85-3.23 (1H, m), 3.34-4.38 (17H, m), 6.60-6.76 (2H, m), 6.87-6.91 (1H, m), 7.01-7.09 (2H, m), 7.24-7.40 (5H, m). LRMS: APCl$^+$ m/z 632 [MH$^+$].

Examples 116-119

These compounds were prepared by the method of example 121 starting from the appropriate precursor as listed in the table.

| Example | Structure | MS MH+ ion | AP3 Rf | Precursor (Example #) |
|---|---|---|---|---|
| 116[A] | 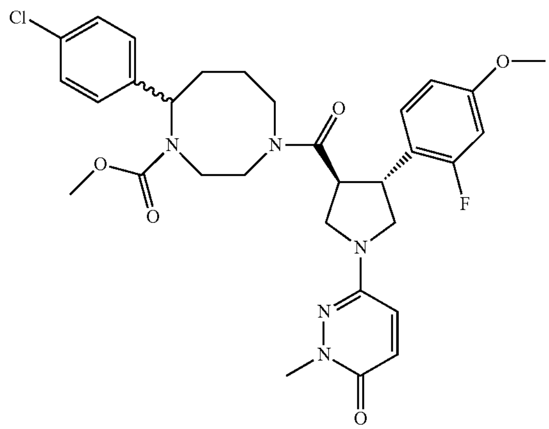 [SMILES: COC(=O)N1CCN(C(=O)[C@@H]2CN(c3ccc(=O)n(C)n3)C[C@H]2c2ccc(OC)cc2F)CCCC1c1ccc(Cl)cc1] | 612 | — | 112 |
| 117[D] | 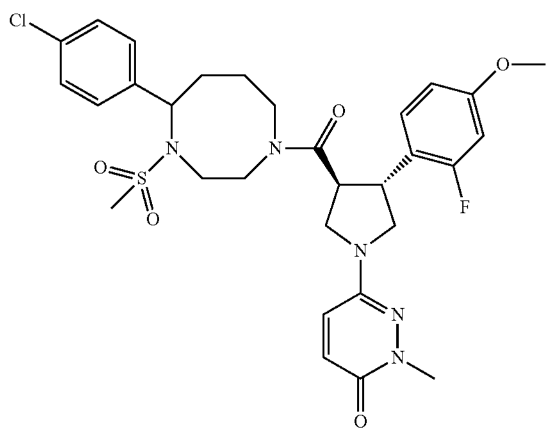 [SMILES: COc1ccc([C@@H]2CN(c3ccc(=O)n(C)n3)C[C@H]2C(=O)N2CCCC(c3ccc(Cl)cc3)N(S(C)(=O)=O)CC2)c(F)c1] | 632 | 3.46 | 113 |
| 118[B] | 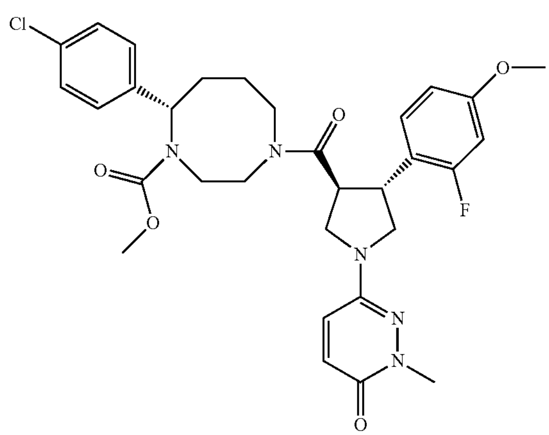 [SMILES: COC(=O)N1CCN(C(=O)[C@@H]2CN(c3ccc(=O)n(C)n3)C[C@H]2c2ccc(OC)cc2F)CCC[C@H]1c1ccc(Cl)cc1] | 612 | — | 69 |

-continued

| Example | Structure | MS MH+ ion | AP3 Rf | Precursor (Example #) |
|---|---|---|---|---|
| 119[B] | 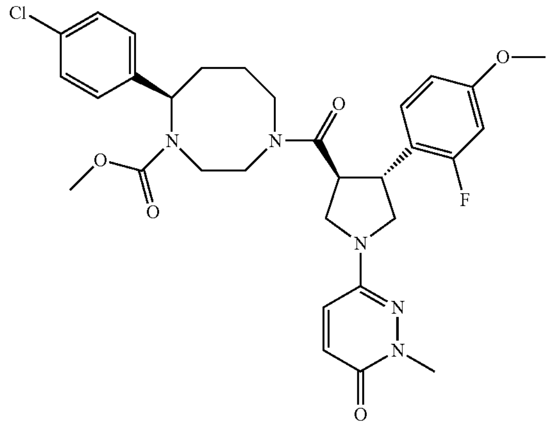 [SMILES: COC(=O)N1CCN(C(=O)[C@@H]2CN(c3ccc(=O)n(C)n3)C[C@H]2c2ccc(OC)cc2F)CCC[C@@H]1c1ccc(Cl)cc1] | 612 | — | 90 |

[A] = mixture of epimers;
[B] = single epimer;
[D] = single epimer of unknown absolute configuration at site of chlorophenyl substitution Preparations Preparation 1:
3-chloro-1-(2,4-difluorophenyl)propan-1-one

To a stirred mixture of aluminium (III) chloride (11.70 g, 88.0 mmol) in 1,3-difluorobenzene (21 mL) at RT was added 3-chloropropionyl chloride (4.0 mL, 41.9 mmol). The reaction mixture was stirred at 60° C. for 6 h. The mixture was cooled to RT and was poured into an ice/2M aqueous hydrochloric acid mixture (100 mL). After vigorous stirring, the mixture was extracted with DCM (2×75 ml). The combined organic extracts were dried over magnesium sulphate and concentrated in vacuo to give 8.68 g (quantitative yield) of crude title compound as an orange oil.
$^1$H NMR (400 MHz, CDCl$_3$) δ 3.35-3.45 (2H, t), 3.80-3.90 (2H, t), 6.80-6.90 (1H, m), 6.90-7.00 (1H, m), 7.90-8.00 (1H, m).

Preparation 2: (±)-1-benzyl-5-(2,4-difluorophenyl)-1,4-diazepane

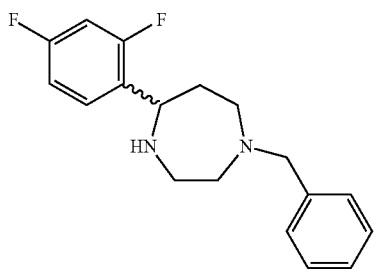 [SMILES: Fc1ccc(C2CCN(Cc3ccccc3)CCN2)c(F)c1]

A solution of N-benzylethylenediamine (2.50 g, 16.64 mmol) in 4-methyl-pentan-2-one (50 mL) was allowed to stir at reflux under Dean-Stark conditions for 3 h. The solution was cooled to RT and to it was added triethylamine (3.48 mL, 25.0 mmol) and the compound of preparation 1 (3.75 g, 18.3 mmol). The reaction mixture was stirred at 60° C. for 16 h. The mixture was cooled to RT and concentrated in vacuo. The residue was dissolved in a mixture of propan-2-ol and water (50 mL, 95:5) and stirred at RT for 16 h. Sodium borohydride (1.50 g, 39.65 mmol) was added and the reaction mixture was allowed to stir at RT for 16 h. The reaction was diluted by adding water (100 mL) and the propan-2-ol was removed in vacuo. The aqueous mixture was extracted with DCM (3×50 mL). The combined organic extracts were dried over magnesium sulphate and concentrated in vacuo to give the crude residue. Purification by column chromatography on silica gel using ethyl acetate:methanol:0.88 ammonia (gradient from 98:2:0.2 to 80:20:3) gave 2.28 g (45%) of the racemic title compound as a yellow oil.
$^1$H NMR (400 MHz, CDCl$_3$) δ 1.85-1.95 (1H, m), 2.00-2.10 (1H, m), 2.60-2.75 (2H, m), 2.75-2.90 (2H, m), 2.95-3.05 (1H, m), 3.10-3.20 (1H, m), 3.68 (2H, s), 4.25-4.35 (1H, m), 6.70-6.80 (1H, m), 6.80-6.90 (1H, m), 7.20-7.40 (5H, m), 7.40-7.50 (1H, m). LRMS: APCl$^+$ m/z 303 [MH$^+$].

Preparation 3: (±)-1-benzyl-5-(4-chlorophenyl)-1,4-diazepane

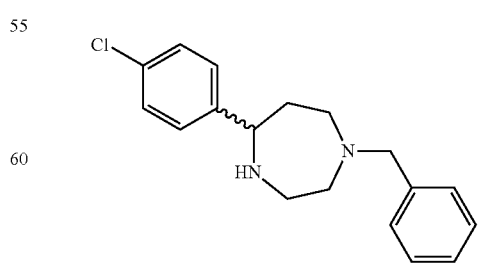

This compound was prepared by the method of preparation 2 starting from N-benzylethylenediamine but using commercially available 3-chloro-1-(4-chlorophenyl)propan-1-one. LRMS: APCl⁺ m/z 300 [MH⁺].

Preparation 4:
(±)-5-(2,4-difluorophenyl)-1,4-diazepane

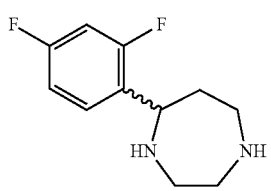 [SMILES: Fc1ccc(C2CCNCCN2)c(F)c1]

To a solution of the compound of preparation 2 (220 mg, 0.728 mmol) in ethanol (20 mL) was added 20% palladium (II) hydroxide on carbon catalyst (102 mg, 0.146 mmol) and ammonium formate (229 mg, 3.64 mmol). The reaction mixture was stirred at 75° C. for 3 h. The solution was cooled to RT and the catalyst was filtered off under nitrogen using Arbocel®. The catalyst was washed with a further 15 ml ethanol and the combined filtrates were concentrated in vacuo to give 172 mg (quantitative yield) of crude (racemic) title compound as a colourless oil.

$^1$H NMR (400 MHz, CD$_3$OD) δ 1.85-1.95 (1H, m), 2.00-2.10 (1H, m), 2.85-3.05 (4H, m), 3.05-3.15 (2H, m), 4.10-4.20 (1H, m), 6.85-6.95 (2H, m), 7.40-7.50 (1H, m). LRMS: APCl⁺ m/z 213 [MH⁺].

Preparation 5: (±)-{7a-(4-chlorophenyl)hexahydro-5H-pyrrolo[1,2-a]imidazol-5-one}

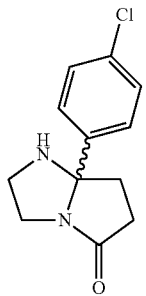 [SMILES: O=C1CCC2(c3ccc(Cl)cc3)NCCN12]

To a solution of 3-(4-chlorobenzoyl)propionic acid (40 g, 190 mmol) in xylene (250 mL) were added ethylenediamine (22.6 g, 376 mol), and 12M hydrochloric acid (0.500 mL, 6 mmol). The reaction mixture was stirred at reflux under Dean-Stark for 12 h, and cooled to RT. The solid was collected by filtration and washed with xylene to give the crude residue. This was dissolved in DCM (400 ml) and filtered. The filtrate was concentrated in vacuo to give 36.6 g (62%) of the racemic title compound as a beige solid.

$^1$H NMR (400 MHz, CD$_3$Cl) δ 2.22-2.35 (2H, m), 2.49-2.56 (1H, m), 2.78-2.95 (3H, m), 3.27-3.34 (1H, m), 3.68-3.77 (1H, m), 7.32-7.35 (2H, m), 7.42-7.46 (7.42-7.46 (2H, m). LRMS: APCl⁺ m/z 237 [MH⁺].

Preparation 6:
(±)-[5-(4-chlorophenyl)-1,4-diazocane]

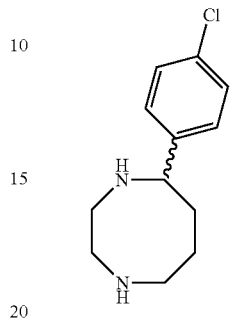

Lithium aluminium hydride (3.21 g, 84.5 mmol) was added to a flask containing the compound of preparation 5 (5.00 g, 21.1 mmol) and diethyl ether (120 ml) was added. The reaction mixture was stirred at RT for 30 min then at reflux for 72 h. The reaction was cooled in an ice bath and quenched by adding water (3.2 ml), 2M sodium hydroxide solution (3.2 ml) and water (9.6 ml). The reaction mixture was filtered through Celite® and washed with diethyl ether (25 ml). The filtrate was concentrated in vacuo to give the crude residue. Purification by column chromatography on silica gel using dichloromethane:methanol:0.88 ammonia (75:25:2.5) gave 2.3 g (45%) of the racemic title compound as a colourless oil.

$^1$H NMR (400 MHz, CD$_3$Cl) δ 1.56-1.83 (3H, m), 1.96-2.04 (1H, m), 2.74-3.10 (6H, m), 3.84-3.88 (1H, m), 7.26-7.31 (4H, m). LRMS: APCl⁺ m/z 225 [MH⁺].

Preparations 7-11

These compounds were prepared by the method of preparations 5 and 6 starting from ethylenediamine and commercially available propionic acids analogous to those used in preparation 5. Each compound was obtained as a racemate.

| Preparation | Structure | MS MH + ion |
|---|---|---|
| 7 | 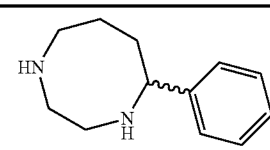 | 191 |
| 8 | 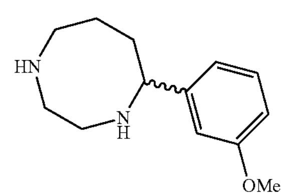 [SMILES: COc1cccc(C2CCCNCCN2)c1] | 221 |
| 9 | 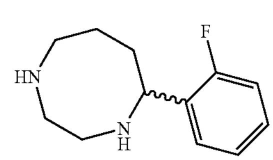 [SMILES: Fc1ccccc1C1CCCNCCN1] | 209 |

| Preparation | Structure | MS MH + ion |
|---|---|---|
| 10 | 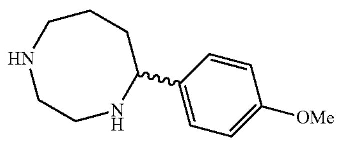 [SMILES: COc1ccc(C2CCCNCCN2)cc1] | 221 |
| 11 | 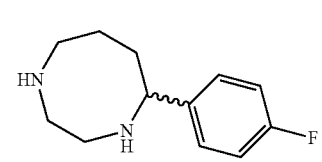 [SMILES: Fc1ccc(C2CCCNCCN2)cc1] | 209 |

Preparation 12: (S) and (R)-5-(4-chlorophenyl)-1,4-diazocane

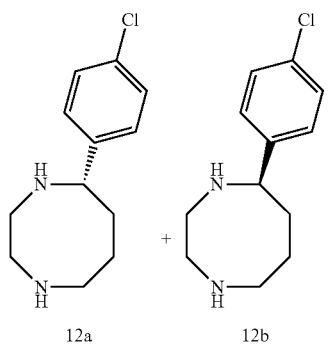 [SMILES: Clc1ccc([C@@H]2CCCNCCN2)cc1 ; Clc1ccc([C@H]2CCCNCCN2)cc1]

12a    12b

Chiral resolution of 12 g of the racemic compound of preparation 6 was initially achieved by column chromatography on a 500*50 mm id Chiralcel OD-H column eluting with heptane:isopropanol:diethylamine (80:20:0.1). This gave 5.74 g (96% of theory) of the first-eluting enantiomer (preparation 12a) as a colourless oil in 99.4% ee and 5.13 g (86% of theory) of the second-eluting enantiomer (preparation 12b) as a colourless oil in 95.5% ee. For analysis purposes, a Chiralcel OD-H 250×4.6 column at 1 ml/min elutes the 2 enantiomers with retention times of 6.10 and 8.68 minutes, respectively. Each displayed identical proton NMR spectra: $^1$H NMR (400 MHz, CD$_3$Cl) δ 1.56-1.83 (3H, m), 1.96-2.04 (1H, m), 2.74-3.10 (6H, m), 3.84-3.88 (1H, m), 7.26-7.31 (4H, m). LRMS: APCl$^+$ m/z 225 [MH$^+$].

Alternatively, salt formation of the racemic compound of preparation 6 with a chiral acid allowed fractional crystallisation of a single diastereoisomeric salt 12c with the advantage of subsequently allowing elucidation of absolute stereochemistry.

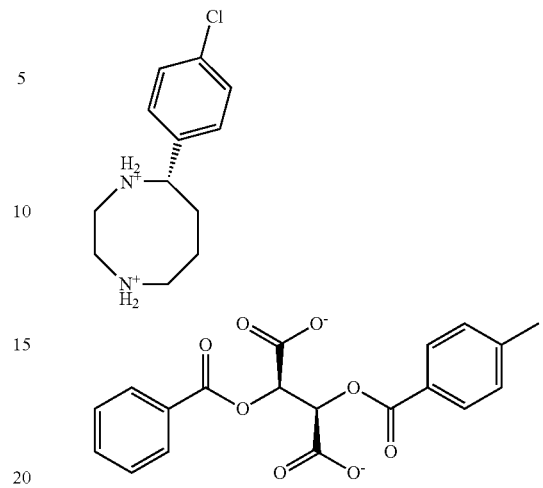

12c

Thus, 5.0 g of the racemic compound of preparation 6 was dissolved in tert-butyl methyl ether (150 mL), the solution heated to 57° C. then 75 ml solvent evaporated at atmospheric pressure. 45 ml ethanol was added and a further 65 ml of the solution evaporated. On cooling to 45° C., 8.2 g di-p-toluoyl-L-tartaric acid was charged in one portion, the suspension reheated to 45° C. and the solution allowed to cool to 20° C. over three hours before granulating for a further 13 h. Filtration gave the di-p-toluoyl-L-tartrate salt 12c (8.5 g) as a white solid which, upon repeated recrystallisation from 10% v/v water in methanol, gave material of >98% ee. The absolute configuration, shown by X-ray crystallography, was the diazocane S enantiomer. Chiral HPLC analysis of 'free-based' 12c showed that this corresponded with enantiomer 12a.

Preparation 13: (±)-tert-butyl 5-(4-chlorophenyl)-1,4-diazocane-1-carboxylate

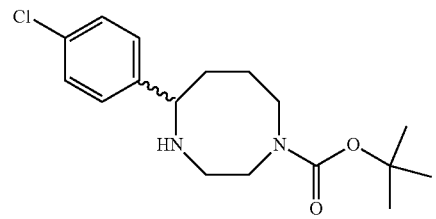 [SMILES: CC(C)(C)OC(=O)N1CCCC(c2ccc(Cl)cc2)NCC1]

Triethylamine (0.285 mL, 2.05 mmol) was added to a solution of the compound of preparation 6 (460 mg, 2.05 mmol) in THF (10 mL), Di-t-butyl dicarbonate (536 mg, 2.46 mmol) was added and the resulting solution was stirred at RT for 16 h. The reaction was concentrated in vacuo and residue diluted by adding sodium hydrogen carbonate solution (10 mL) and extracted with EtOAc (4×20 mL). The combined organic extracts were concentrated in vacuo to give the crude residue. Purification by column chromatography on silica gel using EtOAc gave 419 mg (63%) of the racemic title compound as a colourless oil.

$^1$H NMR (400 MHz, CDCl$_3$) δ 1.47-1.49 (9H, m), 1.54-1.70 (2H, m), 1.74-1.81 (1H, m), 1.87-1.98 (1H, m), 2.85-2.94 (1H, m), 2.97-3.12 (2H, m), 3.29-3.51 (1H, m), 3.59-3.69 (1H, m), 3.72-3.80 (1H, m), 3.82-3.96 (1H, m), 7.23-7.28 (4H, m). LRMS: EI$^+$ m/z 325 [MH$^+$].

Enantiomers 13a and 13b were similarly prepared starting from the compounds of preparations 12a and 12b, respectively.

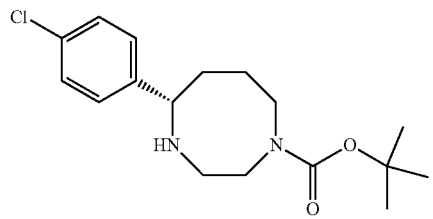

13a

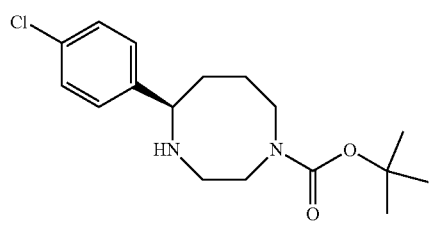

13b

Preparation 14: (±)-1-tert-butyl 4-methyl 5-(4-chlorophenyl)-1,4-diazocane-1,4-dicarboxylate

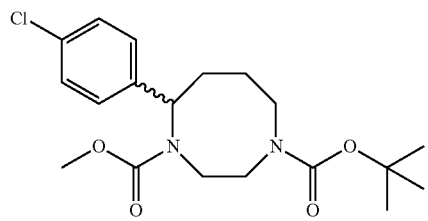

To a stirred solution of the compound of preparation 13 (469 mg, 1.44 mmol) in pyridine (15 mL) were added triethylamine (805 μL, 5.77 mmol), methyl chloroformate (781 μL, 10.12 mmol) and DMAP (352 mg, 2.88 mmol). The reaction was stirred at 60° C. for 16 h. The reaction was cooled to RT and was quenched by adding potassium carbonate solution (10 mL). The reaction mixture was concentrated in vacuo and the residue diluted with water (15 mL). The aqueous mixture was extracted with DCM (3×10 mL). The combined organic extracts were concentrated in vacuo to give the crude residue. Purification by column chromatography on silica gel using pentane:ethyl acetate (gradient from 3:1 to pure EtOAc) gave 322 mg (58%) of the racemic title compound as a colourless oil.

$^1$H NMR (400 MHz, CDCl$_3$) δ 1.35-1.50 (9H, s), 1.55-1.65 (1H, m), 1.80-1.95 (2H, m), 2.05-2.30 (1H, m), 2.85-3.15 (3H, m), 3.40-3.50 (1H, m), 3.55-3.65 (1H, m), 3.65-3.80 (3H, m), 3.90-4.00 (1H, m), 5.00-5.35 (1H, m), 7.05-7.30 (4H, m). LRMS: APCI$^+$ m/z 283 [M-Boc+H]$^+$.

Enantiomers 14a and 14b were similarly prepared starting from the compounds of preparations 13a and 13b, respectively.

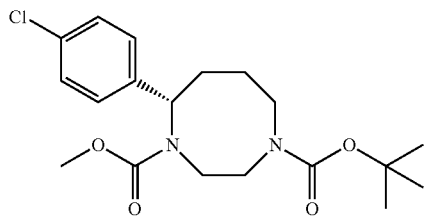 [SMILES: COC(=O)N1CCN(C(=O)OC(C)(C)C)CCCC1c1ccc(Cl)cc1]

14a

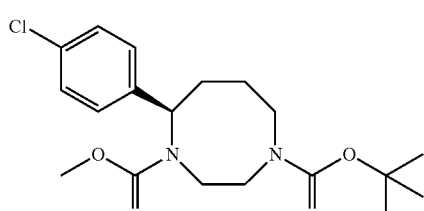

14b

Preparation 15: (±)-methyl 8-(4-chlorophenyl)-1,4-diazocane-1-carboxylate

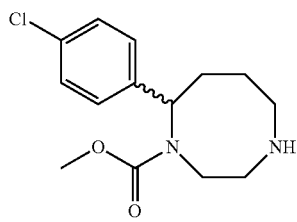 [SMILES: COC(=O)N1CCNCCCC1c1ccc(Cl)cc1]

To a stirred solution of the compound of preparation 14 (322 mg, 0.841 mmol) in DCM (5 mL) was added 4M hydrogen chloride in 1,4-dioxane (5 mL). The reaction was stirred at RT for 16 h. The reaction mixture was concentrated in vacuo and the residue diluted with potassium carbonate solution (15 mL). The aqueous mixture was extracted with DCM (3×10 mL). The combined organic extracts were concentrated in vacuo to give 230 mg (97%) of the racemic title compound as a yellow oil.

$^1$H NMR (400 MHz, CDCl$_3$) δ 1.75-2.05 (2H, m), 2.25-2.40 (1H, m), 2.65-2.85 (2H, m), 2.95-3.05 (2H, m), 3.05-3.25 (2H, m), 3.40-3.50 (1H, m), 3.65-3.75 (3H, m), 5.05-5.30 (1H, dd), 7.10-7.30 (4H, m). LRMS: APCI$^+$ m/z 283 [MH$^+$].

Enantiomers 15a and 15b were similarly prepared starting from the compounds of preparations 14a and 14b, respectively.

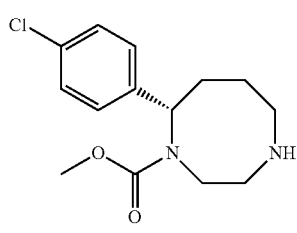

15a

-continued

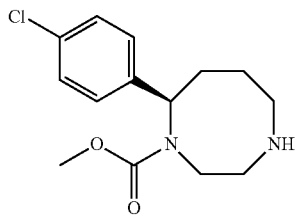

15b

Preparation 16: (±)-tert-butyl 5-(4-chlorophenyl)-4-(methylsulfonyl)-1,4-diazocane-1-carboxylate

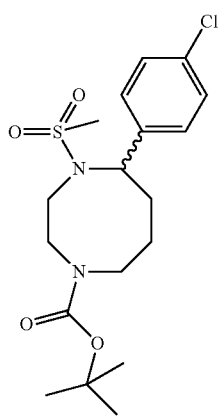 [SMILES: CC(C)(C)OC(=O)N1CCCC(c2ccc(Cl)cc2)N(S(C)(=O)=O)CC1]

DMAP (2.67 g, 21.9 mmol) was added to a solution of the compound of preparation 13 (2.37 g, 7.30 mmol) in pyridine (20 mL), methanesulfonyl chloride (1.69 mL, 21.9 mmol) was added and the resulting solution was stirred at 50° C. for 3 h. The reaction was concentrated in vacuo and residue diluted by adding 10% citric acid solution (50 mL) and extracted with EtOAc (4×50 mL). The combined organic extracts were washed with 10% citric acid (50 ml), brine (50 ml), dried over sodium sulphate, filtered and concentrated in vacuo to give the crude residue. Purification by column chromatography on silica gel using pentane:ethyl acetate (1:1) gave 1.69 g (58%) of the racemic title compound as a colourless oil.

$^1$H NMR (400 MHz, CDCl$_3$) δ 1.47-1.49 (9H, m), 1.70-1.77 (2H, m), 1.98-2.06 (1H, m), 2.12-2.30 (1H, m), 2.40-2.43 (3H, m), 3.11-3.30 (1H, m), 3.34-3.46 (2H, m), 3.52-3.60 (1H, m), 3.73-3.89 (1H, m), 4.07-4.15 (1H, m), 4.91-4.98 (1H, m), 7.22-7.26 (2H, m), 7.31-7.35 (2H, m). LRMS: APCl$^+$ m/z 403 [MH$^+$].

Preparation 17: (±)-8-(4-chlorophenyl)-1-(methylsulfonyl)-1,4-diazocane hydrochloride

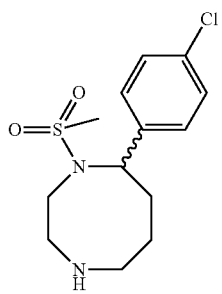 [SMILES: CS(=O)(=O)N1CCNCCCC1c1ccc(Cl)cc1]

4M HCl in dioxane (20 mL, 80 mmol) was added to the compound of preparation 16 (1.69 g, 4.19 mmol) and the resulting solution was stirred at RT for 16 h. The reaction was concentrated in vacuo to give 1.42 g (100%) of the racemic title compound as an off-white solid.

$^1$H NMR (400 MHz, CDCl$_3$) δ 1.92-2.12 (2H, m), 2.22-2.43 (4H, m), 2.86-3.01 (1H, m), 3.36-3.80 (5H, m), 4.14-4.26 (1H, m), 4.49-5.07 (1H, m), 7.30-7.39 (4H, m). LRMS: APCl$^+$ m/z 303 [MH$^+$].

Preparations 17a-26

These compounds were prepared by the methods of preparations 13-17, starting from the appropriate precursors as listed in the table.

| Preparation | Structure | MS MH+ ion | Precursor (Prep #) |
|---|---|---|---|
| 17a[1] | ![structure] | 302 | 12a |
| 18[2] | ![structure] | 287 | 11 |
| 19[2] | ![structure] | 269 | 7 |
| 20[2] | ![structure] | 249 | 7 |
| 21[2] | ![structure] | 261 | 7 |

-continued

| Preparation | Structure | MS MH+ ion | Precursor (Prep #) |
|---|---|---|---|
| 22[2] | 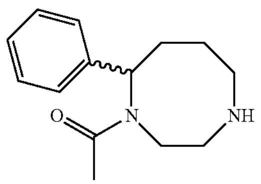 [SMILES: CC(=O)N1CCNCCCC1c1ccccc1] | 233 | 7 |
| 22a[2] | 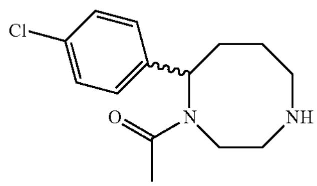 [SMILES: CC(=O)N1CCNCCCC1c1ccc(Cl)cc1] | 266 | 6 |
| 22b[1] | 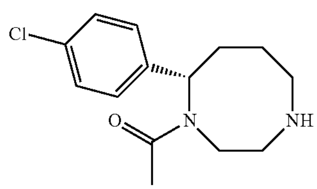 [SMILES: CC(=O)N1CCNCCC[C@H]1c1ccc(Cl)cc1] | 266 | 12a |
| 23[2] | 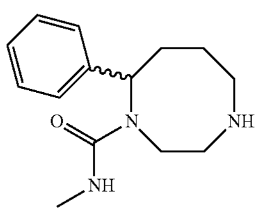 [SMILES: CNC(=O)N1CCNCCCC1c1ccccc1] | 248 | 7 |
| 24[2] | 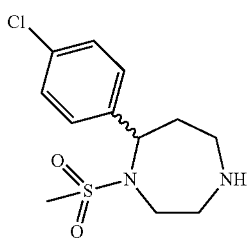 [SMILES: CS(=O)(=O)N1CCNCCC1c1ccc(Cl)cc1] | 288 | 97 |
| 25[2] | 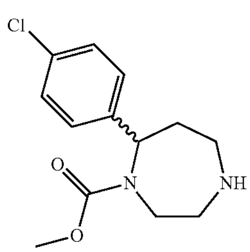 [SMILES: COC(=O)N1CCNCCC1c1ccc(Cl)cc1] | 268 | 97 |
| 26[2] | 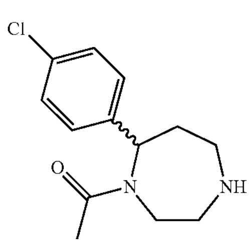 [SMILES: CC(=O)N1CCNCCC1c1ccc(Cl)cc1] | 252 | 97 |

[1] single enantiomer;
[2] racemic

Preparation 27: (4S)-4-benzyl-3-[(2E)-3-(2-fluoro-4-methoxyphenyl)prop-2-enoyl]-1,3-oxazolidin-2-one To a solution of commercially available 2-fluoro-4-methoxycinnamic acid (16.5 g, 84.1 mmol) in DCM (100 mL) at 4° C. was added DMF (0.1 mL), followed by dropwise addition of a solution of oxalyl chloride (14.8 mL, 170 mmol) in DCM (50 mL). The reaction mixture was warmed to RT over 3 h. The reaction was concentrated in vacuo and azeotroped with DCM (2×100 mL) to give the crude intermediate acid chloride. The acid chloride was dissolved in DCM (50 mL) and added dropwise to an ice-cooled solution of (s)-(−)-4-benzyl-2-oxazolidinone (14.3 g, 80.7 mmol), lithium chloride (17.8 g, 421 mmol) and triethylamine (58.8 mL, 421 mmol) in DCM (100 mL). The reaction was stirred at RT for 16 h then diluted by adding water (100 mL) and filtered through Arbocel®. The filtrate was partitioned and the aqueous phase extracted with DCM (2×100 mL). The combined organic extracts were dried over sodium sulphate, filtered and concentrated in vacuo to give the crude residue. This residue was triturated in diethyl ether (150 mL). Filtration gave 20 g (67%) of the title compound as a beige solid.
$^1$H NMR (400 MHz, CDCl$_3$) δ 2.82-2.88 (1H, m), 3.36-3.40 (1H, m), 3.84 (3H, s), 4.18-4.27 (2H, m), 4.77-4.83 (1H, m), 6.63-6.67 (1H, m), 6.72-6.76 (1H, m), 7.23-7.37 (5H, m), 7.60-7.64 (1H, m), 7.84-7.88 (1H, m), 8.01-8.05 (1H, m). LRMS: APCl$^+$ m/z 356 [MH$^+$].

Preparation 28: (4S)-4-benzyl-3-[(2E)-3-(4-cyanophenyl)prop-2-enoyl]-1,3-oxazolidin-2-one This compound was prepared by the method of preparation 27, but starting with commercially available 4-cyanocinnamic acid. LRMS: APCl⁺ m/z 333 [MH⁺].

Preparation 29: (4S)-4-benzyl-3-{[(3S,4R)-1-benzyl-4-(2-fluoro-4-methoxyphenyl)pyrrolidin-3-yl]carbonyl}-1,3-oxazolidin-2-one

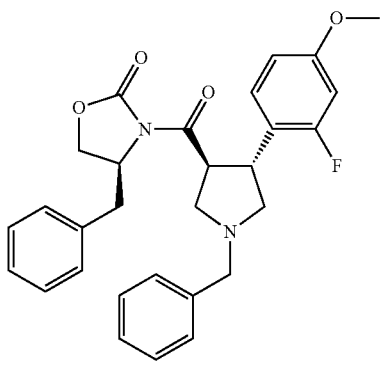 [SMILES: COc1ccc([C@@H]2CN(Cc3ccccc3)C[C@H]2C(=O)N2C(=O)OC[C@@H]2Cc2ccccc2)c(F)c1]

To a solution of the compound of preparation 27 (20 g, 56.3 mmol) in DCM (200 mL) at 5° C. was added trifluoroacetic acid (0.347 mL, 67.5 mml) followed by dropwise addition of commercially available N-(methoxymethyl)-N-(trimethylsilylmethyl)benzylamine (16 g, 67.5 mmol). The reaction mixture was stirred at RT for 64 h then diluted by adding sodium hydrogen carbonate solution (100 mL). The organic extracts were concentrated in vacuo to give the crude residue. Purification by column chromatography on silica gel using ethyl acetate:dichloromethane (1:1) gave 12 g (43%) of the title compound as an oil and as the single diastereoisomer shown.

$^1$H NMR (400 MHz, CDCl$_3$) δ 2.70-2.89 (3H, m), 3.12-3.28 (3H, m), 3.59-3.80 (5H, m), 4.09-4.26 (3H, m), 4.29-4.39 (1H, m), 4.64-4.72 (1H, m), 6.56-6.62 (1H, m), 6.65-6.70 (1H, m), 7.10-7.15 (2H, m), 7.21-7.40 (9H, m). LRMS: APCl⁺ m/z 489 [MH⁺].

Preparations 30-32

These compounds were prepared by the method of preparation 29 using the appropriate precursor(s) as listed in the table. Each compound was obtained as a single diastereoisomer.

| Preparation | Structure | MS MH+ ion | Precursor(s) (Prep #) |
|---|---|---|---|
| 30 | 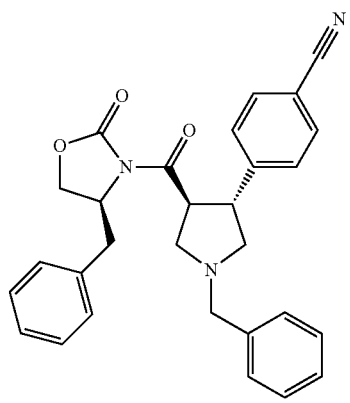 [SMILES: N#Cc1ccc([C@@H]2CN(Cc3ccccc3)C[C@H]2C(=O)N2C(=O)OC[C@@H]2Cc2ccccc2)cc1] | 466 | 28 |
| 31 | 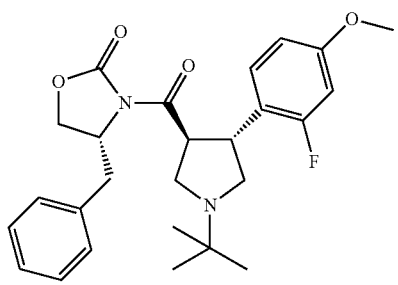 [SMILES: COc1ccc([C@@H]2CN(C(C)(C)C)C[C@H]2C(=O)N2C(=O)OC[C@H]2Cc2ccccc2)c(F)c1] | 455 | 27 |

| Preparation | Structure | MS MH+ ion | Precursor(s) (Prep #) |
|---|---|---|---|
| 32 | 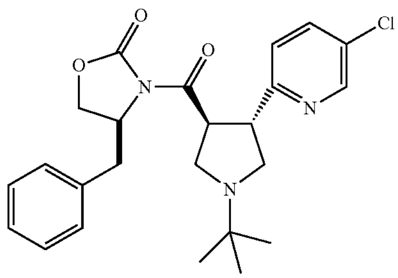 [SMILES: CC(C)(C)N1C[C@@H](C(=O)N2C(=O)OC[C@@H]2Cc2ccccc2)[C@H](c2ccc(Cl)cn2)C1] | 441 | 102 and 103 |

Preparation 33: methyl (3S,4R)-1-benzyl-4-(2-fluoro-4-methoxyphenyl)pyrrolidine-3-carboxylate To a stirred solution of the compound of preparation 29 (12.00 g, 24.56 mmol) in anhydrous methanol (100 mL) at RT was added samarium (III) trifluoromethanesulfonate (1.17 g, 1.96 mmol) portionwise. The reaction was allowed to stir under nitrogen for 16 h at RT. The reaction mixture was concentrated in vacuo to give the crude residue. Purification by column chromatography on silica gel using pentane:ethyl acetate (gradient from 4:1 to 1:1) gave 6.50 g (77%) of the title compound as a single enantiomer as a pale yellow oil.

$^1$H NMR (400 MHz, d$^6$-DMSO) δ 2.55-2.65 (1H, m), 2.90-3.05 (3H, m), 3.10-3.20 (1H, m), 3.60-3.65 (4H, m), 3.70-3.85 (5H, m), 6.60-6.65 (1H, d), 6.70-6.75 (1H, d), 7.20-7.40 (6H, m). LRMS: APCl$^+$ m/z 344 [MH]$^+$.

Preparations 34-36

These compounds were prepared by the method of preparation 33 using the precursor as listed in the table. Each compound was obtained as a single enantiomer.

| Preparation | Structure | MS MH + ion | Precursor (Prep #) |
|---|---|---|---|
| 34 | 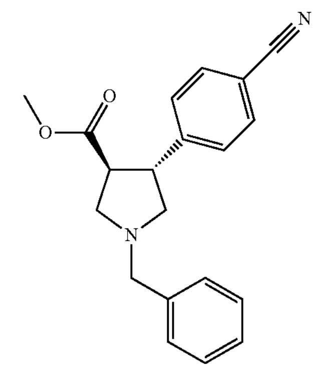 [SMILES: COC(=O)[C@@H]1CN(Cc2ccccc2)C[C@H]1c1ccc(C#N)cc1] | 321 | 30 |
| 35 | 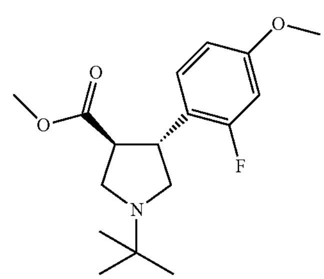 | 310 | 31 |
| 36 | 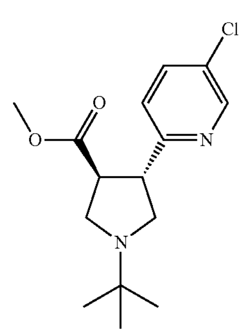 [SMILES: COC(=O)[C@@H]1CN(C(C)(C)C)C[C@H]1c1ccc(Cl)cn1] | 296 | 32 |

Preparation 37: methyl (3S,4R)-4-(2-fluoro-4-methoxyphenyl)pyrrolidine-3-carboxylate

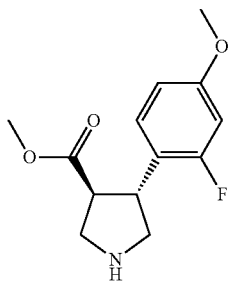 [SMILES: COC(=O)[C@@H]1CNC[C@H]1c1ccc(OC)cc1F]

To a solution of the compound of preparation 33 (1.8 g, 5.2 mmol) in methanol (20 mL) were added 20% palladium hydroxide on carbon (180 mg), and 1-methyl-1,4-cyclohexadiene (2.94 mL, 26.2 mmol). The reaction mixture was stirred at reflux for 2.5 h then cooled to RT. The reaction was filtered over Arbocel® washing with methanol. The filtrate was concentrated in vacuo to obtain 1.30 g (98% yield) of the title compound as a colourless oil.

$^1$H NMR (400 MHz, CD$_3$OD) δ 2.83-2.89 (1H, m), 3.09-3.15 (1H, m), 3.20-3.25 (1H, m), 3.29-3.37 (2H, m), 3.59-3.66 (1H, m), 3.64 (3H, s), 3.77 (3H, s), 6.64-6.72 (2H, m), 7.20-7.24 (1H, m). LRMS: APCl$^+$ m/z 254 [MH$^+$].

Preparation 38: methyl (3S,4S)-4-(5-chloropyridin-2-yl)-1-[1,2,4]triazolo[4,3-b]pyridazin-6-ylpyrrolidine-3-carboxylate

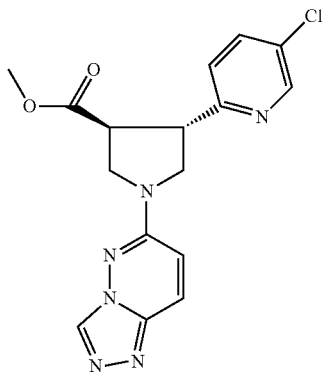 [SMILES: COC(=O)[C@@H]1CN(c2ccc3nncn3n2)C[C@H]1c1ccc(Cl)cn1]

To a solution of the compound of preparation 104 (970 mg, 3.50 mmol) in n-butanol (20 mL) was added diisopropylethylamine (2.44 mL, 14.0 mmol), followed by 6-chloro[1,2,4]triazolo[4,3-b]pyridazine (811 mg, 5.25 mmol). The resulting solution was warmed to 120° C. for 2 h. The reaction mixture was concentrated in vacuo. The residue was partitioned between brine (30 mL) and EtOAc (50 mL). The organic extracts were dried over magnesium sulphate, filtered and concentrated in vacuo to give the crude residue. Purification by column chromatography on silica gel using dichloromethane:methanol (95:5) gave 1.53 g (100%) of the title compound as a single enantiomer as an oily solid.

$^1$H NMR (400 MHz, CH$_3$OD) δ 3.65 (3H, s), 3.67-3.84 (3H, m), 3.93-4.00 (1H, m), 4.03-4.10 (2H, m), 7.07-7.11 (1H, m), 7.37-7.42 (1H, m), 7.75-7.80 (1H, m), 7.86-7.91 (1H, m), 8.49-8.52 (1H, m), 8.95 (1H, s). LRMS: APCl$^+$ m/z 359 [MH$^+$].

Preparation 39: methyl (3S,4S)-4-(2,4-difluorophenyl)-1-[1,2,4]triazolo[4,3-b]pyridazin-6-ylpyrrolidine-3-carboxylate

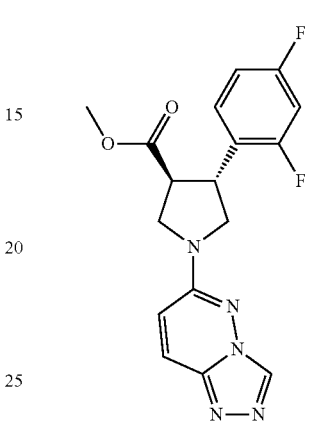

This compound was prepared by the method of preparation 38, starting from the same chloro-heterocycle and the compound of preparation 105. LRMS: APCl$^+$ m/z 360 [MH$^+$].

Preparations 40-43

These compounds were prepared by the method of example 105 starting from commercially available 3-chloro-6-cyanopyridazine and the appropriate precursor as listed in the table. Each compound was obtained as a single enantiomer.

| Preparation | Structure | MS MH+ ion | Precursor (Prep #) |
|---|---|---|---|
| 40 | 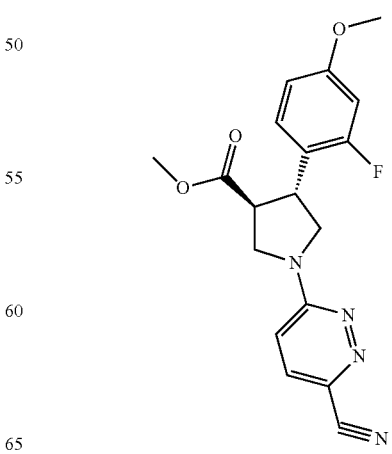 | 357 | 37 |

| Preparation | Structure | MS MH+ ion | Precursor (Prep #) |
|---|---|---|---|
| 41 | (methyl 3-(2,4-difluorophenyl)-pyrrolidine-4-carboxylate with 6-cyanopyridazin-3-yl) | 345 | 105 |
| 42 | (methyl 3-(5-chloropyridin-2-yl)-pyrrolidine-4-carboxylate with 6-cyanopyridazin-3-yl) | 343 | 104 |
| 43 | (methyl 3-(4-cyanophenyl)-pyrrolidine-4-carboxylate with 6-cyanopyridazin-3-yl) | 334 | 96 |

Preparations 44-45

These compounds were prepared by the method of example 107 starting from commercially available 3,6-dichloropyridazine and the appropriate precursor as listed in the table. Each compound was obtained as a single enantiomer.

| Preparation | Structure | MS MH+ ion | Precursor (Prep #) |
|---|---|---|---|
| 44 | (methyl 3-(2-fluoro-4-methoxyphenyl)-pyrrolidine-4-carboxylate with 6-chloropyridazin-3-yl) | 365 | 37 |
| 45 | (methyl 3-(2,4-difluorophenyl)-pyrrolidine-4-carboxylate with 6-chloropyridazin-3-yl) | 353 | 105 |

Preparations 46-47

These compounds were prepared by the method of example 111 by refluxing in acetic acid the compounds of preparations 44 and 45 respectively. Each compound was obtained as a single enantiomer.

| Preparation | Structure | MS MH+ ion | Precursor (Prep #) |
|---|---|---|---|
| 46 | (methyl 3-(2-fluoro-4-methoxyphenyl)-pyrrolidine-4-carboxylate with 6-oxo-pyridazin-3-yl) | 348 | 44 |

| Preparation | Structure | MS MH+ ion | Precursor (Prep #) |
|---|---|---|---|
| 47 | 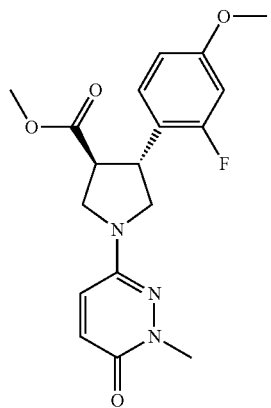 | 336 | 45 |

Preparation 48: methyl (3S,4R)-4-(2-fluoro-4-methoxyphenyl)-1-(1-methyl-6-oxo-1,6-dihydropyridazin-3-yl)pyrrolidine-3-carboxylate

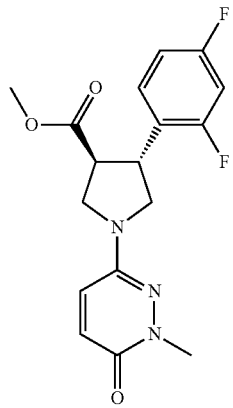 [SMILES: COC(=O)[C@@H]1CN(c2ccc(=O)n(C)n2)C[C@H]1c1ccc(F)cc1F]

This compound was prepared as a single enantiomer by the method of example 115 using the compound of preparation 46. LRMS: APCl+ m/z 362 [MH+].

Preparation 49: methyl (3S,4R)-4-(2,4-difluorophenyl)-1-(1-methyl-6-oxo-1,6-dihydropyridazin-3-yl)pyrrolidine-3-carboxylate To a stirred suspension of the compound of preparation 105 (25.27 g, 82 mmol) and 6-chloro-2-methylpyridazin-3(2H)-one {*Helvetica Chimica Acta*; (1954), 37, 837-48} (12.0 g, 83.0 mmol) in degassed toluene (500 mL) at RT were added caesium carbonate (111 g, 339 mmol) and (9,9-dimethyl-9H-xanthene-4,5-diyl)-bis[diphenyl phosphine] (6.23 g, 10.8 mmol). The reaction mixture was purged twice with nitrogen. Palladium (II) diacetate (813 mg, 3.62 mmol) was added and the reaction was stirred under nitrogen at 115° C. for 16 h. The reaction mixture was filtered under reduced pressure and the residue was washed with 20 ml toluene. The filtrate was concentrated in vacuo to give crude product residue. Purification by column chromatography on silica gel using heptane: ethyl acetate (gradient from 7:3 to pure EtOAc to EtOAc:MeOH, 95:5) gave 23.85 g (83%) of the title compound as a yellow oil.

$^1$H NMR (400 MHz, CDCl$_3$) δ 3.30-3.40 (1H, m), 3.40-3.50 (1H, m), 3.62 (3H, s), 3.67 (3H, s), 3.62-3.70 (1H, m), 3.75-3.90 (2H, m), 3.90-4.00 (1H, m), 6.75-6.95 (4H, m), 7.15-7.25 (1H, m). LRMS: APCl+ m/z 350 [MH]+.

Preparation 50: methyl (3S,4R)-4-(5-chloropyridin-2-yl)-1-(1-methyl-6-oxo-1,6-dihydropyridazin-3-yl)pyrrolidine-3-carboxylate

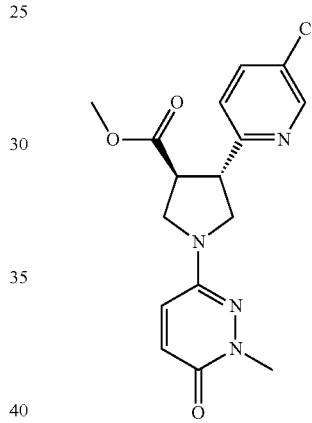

This compound was prepared as a single enantiomer by the method of preparation 49 using the same chloro-heterocycle and the compound of preparation 104. LRMS: APCl+ m/z 348 [MH]+.

Preparation 51: methyl (3S,4R)-4-(2-fluoro-4-methoxyphenyl)-1-pyridazin-3-ylpyrrolidine-3-carboxylate

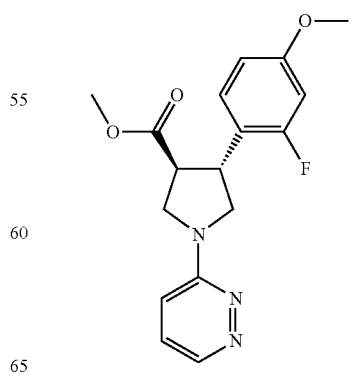

To a stirred suspension of the compound of preparation 44 (407 mg, 1.11 mmol) in methanol (5 mL) was added 20% palladium (II) hydroxide on carbon catalyst (27 mg, 0.189 mmol) and 1-methyl-1,4-cyclohexadiene (438 μL, 3.89 mmol). The reaction mixture was stirred under nitrogen at reflux for 3 h and then allowed to cool to RT over 16 h. The catalyst was filtered off under nitrogen using Arbocel®. The catalyst was washed with a further 10 ml methanol and the combined filtrates were concentrated in vacuo to give 438 mg (quantitative yield) of crude product as a colourless oil that was used directly in the ester hydrolysis of preparation 63.

$^1$H NMR (400 MHz, CDCl$_3$) δ 3.45-3.55 (3H, m), 3.68 (3H, s), 3.77 (3H, s), 3.90-4.05 (2H, m), 4.05-4.25 (1H, m), 6.60-6.70 (2H, m), 7.05-7.15 (1H, t), 7.20-7.25 (1H, m), 7.75-7.80 (1H, m), 8.60-8.65 (1H, d). LRMS: EI$^+$ m/z 332 [MH$^+$].

Preparation 52: (3S,4R)-1-(6-cyanopyridazin-3-yl)-4-(2,4-difluorophenyl)pyrrolidine-3-carboxylic acid

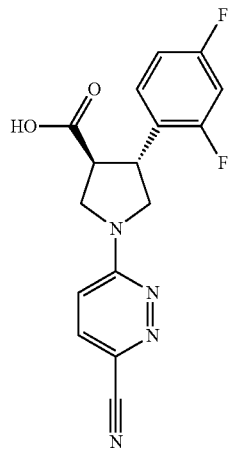 [SMILES: N#Cc1ccc(N2C[C@@H](C(=O)O)[C@H](c3ccc(F)cc3F)C2)nn1]

To a stirred solution of the compound of preparation 41 (3.82 g, 11.1 mmol) in 1,4-dioxane (100 mL) and water (50 mL) at 5° C. was added 1M aqueous sodium hydroxide solution (9.98 mL, 9.98 mmol) dropwise. The reaction was allowed to stir for 16 h at RT, then neutralised with 2M aqueous hydrochloric acid (4.99 mL, 9.98 mmol) and concentrated in vacuo. Crude product residue was azeotroped with toluene (3×50 mL) to give 3.97 g (92%) of the title compound as a cream coloured solid, containing one equivalent of sodium chloride by-product.

$^1$H NMR (400 MHz, d$^6$-DMSO) δ 3.40-3.50 (2H, m), 3.65-3.80 (1H, m), 3.85-4.20 (3H, m), 7.00-7.10 (2H, m), 7.15-7.25 (1H, m), 7.45-7.55 (1H, m), 7.80-7.85 (1H, d). LRMS: APCl$^+$ m/z 331 [MH]$^+$.

Preparations 53-65

These compounds were prepared by the method of preparation 52 starting from the appropriate precursor as listed in the table. Each compound was obtained as a single enantiomer.

| Preparation | Structure | MS MH+ ion | Precursor (Prep #) |
|---|---|---|---|
| 53 | 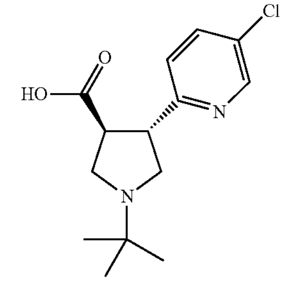 [SMILES: CC(C)(C)N1C[C@@H](C(=O)O)[C@H](c2ccc(Cl)cn2)C1] | 282 | 36 |
| 54 | 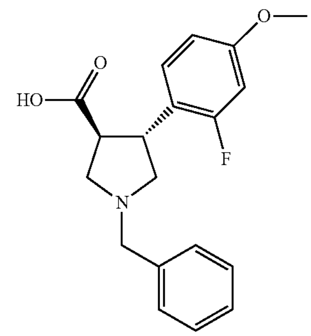 [SMILES: COc1ccc([C@@H]2CN(Cc3ccccc3)C[C@H]2C(=O)O)c(F)c1] | 330 | 33 |
| 55 | 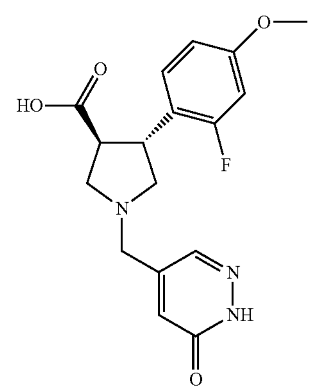 [SMILES: COc1ccc([C@@H]2CN(Cc3cn[nH]c(=O)c3)C[C@H]2C(=O)O)c(F)c1] | 334 | 46 |
| 56 | 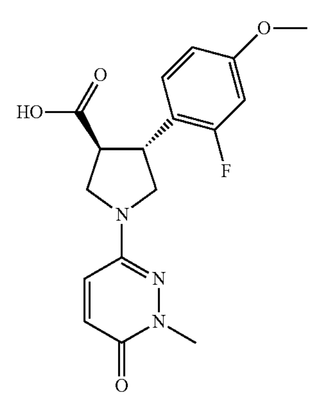 [SMILES: COc1ccc([C@@H]2CN(c3ccc(=O)n(C)n3)C[C@H]2C(=O)O)c(F)c1] | 348 | 48 |

| Preparation | Structure | MS MH+ ion | Precursor (Prep #) |
|---|---|---|---|
| 57 | 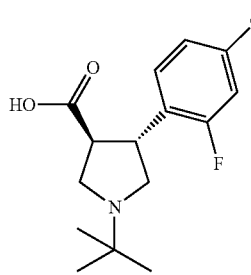 | 296 | 35 |
| 58 | 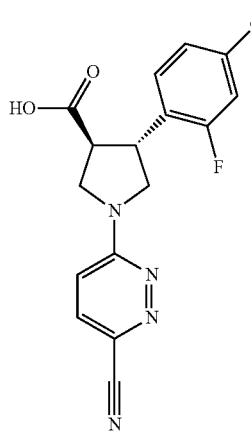 | 343 | 40 |
| 59 | 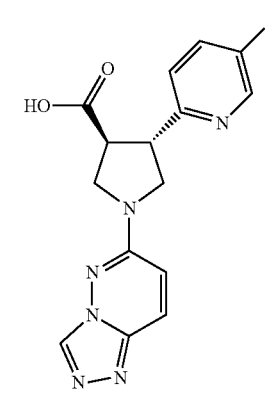 | 344 | 38 |
| 60 | 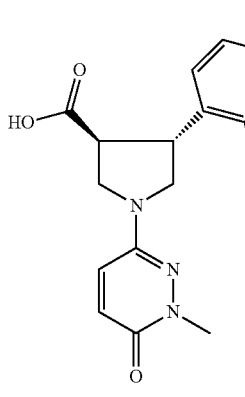 | 336 | 49 |
| Preparation | Structure | MS MH+ ion | Precursor (Prep #) |
|---|---|---|---|
| 61 | 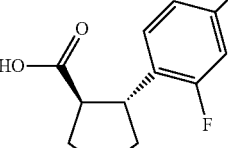 | 346 | 39 |
| 62 | 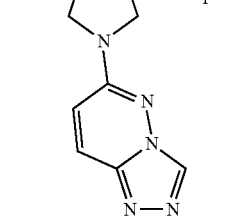 | 322 | 47 |
| 63 | 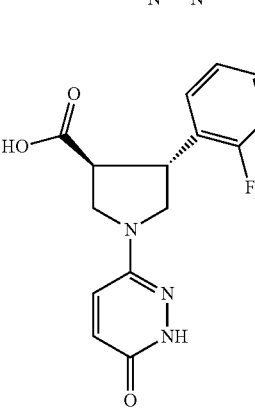 | 318 | 51 |
| 64 | 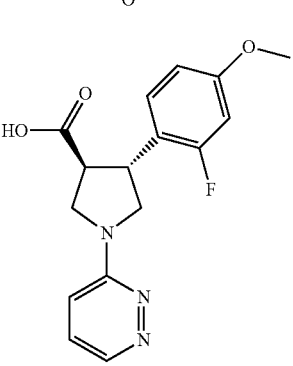 | 320 | 43 |

-continued

| Preparation | Structure | MS MH+ ion | Precursor (Prep #) |
|---|---|---|---|
| 65 | 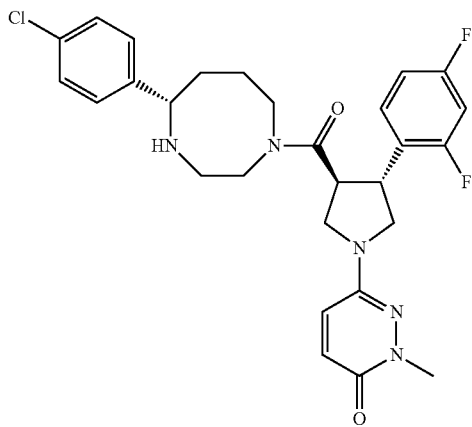 [SMILES: Cn1nc(N2C[C@@H](C(=O)N3CCC[C@@H](c4ccc(Cl)cc4)NCC3)[C@H](c3ccc(F)cc3F)C2)ccc1=O] | 329 | 42 |

Preparation 66: 6-[(3S,4R)-3-{[5S-(4-chlorophenyl)-1,4-diazocan-1-yl]carbonyl}-4-(2,4-difluorophenyl)pyrrolidin-1-yl]-2-methylpyridazin-3(2H)-one To a suspension of the compound of preparation 60 (200 mg, 0.473 mmol) in DCM (15 mL) were added N,N-diisopropylethylamine (328 μL, 1.89 mmol), 1-hydroxybenzotriazole monohydrate (83 mg, 0.544 mmol) and 1-(3-dimethylaminopropyl)-3-ethylcarbodiimide methiodide (176 mg, 0.591 mmol). The reaction mixture was stirred at RT for 30 min. The compound of preparation 12a was then added and the reaction mixture was stirred at RT for 16 h. The reaction was diluted by adding potassium carbonate solution (20 mL) and extracted with DCM (2×5 mL). The combined organic extracts were concentrated in vacuo to give the crude residue. Purification by column chromatography on silica gel using ethyl acetate:methanol:0.88 ammonia (gradient from 98:2:0.2 to 90:10:1) gave 221 mg (86%) of the title compound as a cream coloured foam.

$^1$H NMR (400 MHz, CD$_3$OD) δ 1.30-1.40 (1H, m), 1.45-1.60 (1H, m), 1.65-1.80 (1H, m), 1.80-1.90 (1H, m), 2.70-2.90 (2H, m), 2.95-3.15 (1H, m), 3.40-3.60 (4H, m), 3.64 (3H, s), 3.65-3.75 (1H, m), 3.80-4.00 (4H, m), 4.05-4.25 (1H, m), 6.85-7.00 (3H, m), 7.10-7.20 (2H, m), 7.20-7.30 (3H, m), 7.40-7.55 (1H, m). LRMS: EI$^+$ m/z 542 [MH$^+$].

Preparations 67-71

These compounds were prepared by the method of preparation 66, using the appropriate precursors as listed in the table.

| Preparation | Structure | MS MH+ ion | Precursors (Prep #) |
|---|---|---|---|
| 67$^B$ | | 542 | 60 and 12b |

-continued
| Preparation | Structure | MS MH+ ion | Precursors (Prep #) |
|---|---|---|---|
| 68[A] | 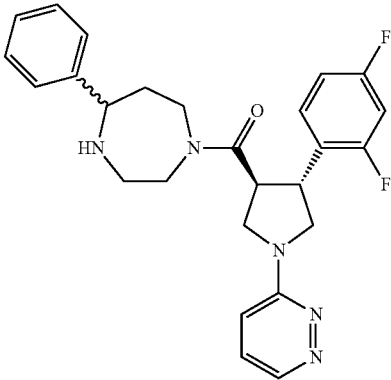 [SMILES: O=C([C@@H]1CN(c2cccnn2)C[C@H]1c1ccc(F)cc1F)N1CCNC(c2ccccc2)CC1] | 464 | 98 and 106 |
| 69[A] | 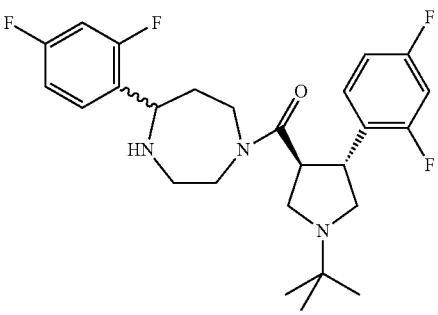 [SMILES: CC(C)(C)N1C[C@@H](C(=O)N2CCNC(c3ccc(F)cc3F)CC2)[C@H](c2ccc(F)cc2F)C1] | 478 | 100 and 4 |
| 70[B] | 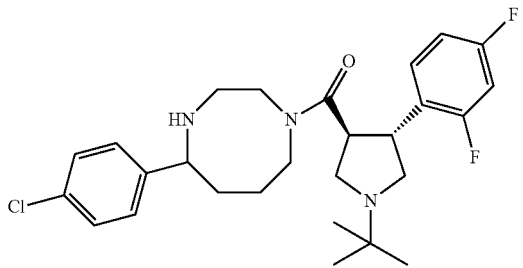 [SMILES: CC(C)(C)N1C[C@@H](C(=O)N2CCCC(c3ccc(Cl)cc3)NCC2)[C@H](c2ccc(F)cc2F)C1] | 490 | 100 and 12a |
| 71[A] | 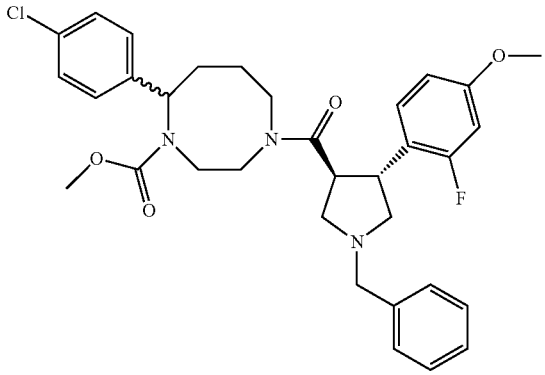 [SMILES: COC(=O)N1CCN(C(=O)[C@@H]2CN(Cc3ccccc3)C[C@H]2c2ccc(OC)cc2F)CCCC1c1ccc(Cl)cc1] | 595 | 54 and 15 |
[A] = mixture of epimers;
[B] = single epimer Preparations 72-85

These compounds were prepared by the method of example 66 using the appropriate precursors as listed in the table. In certain cases, single epimers (marked by an asterisk*) were isolated from the initial epimeric mixture produced, by normal-phase chromatography.

| Preparation | Structure | MS MH+ ion | Precursors (Prep #) |
|---|---|---|---|
| 72[B] | 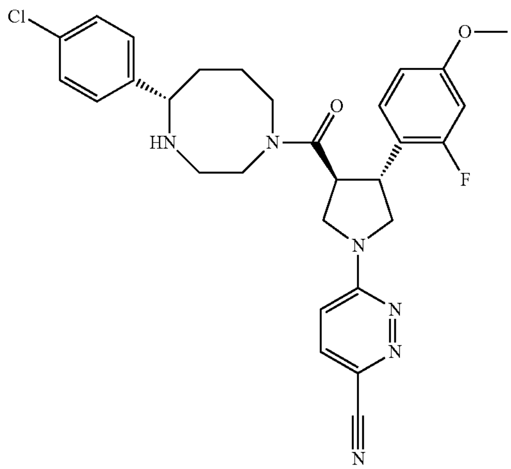 [SMILES: COc1ccc([C@@H]2CN(c3ccc(C#N)nn3)C[C@H]2C(=O)N2CCC[C@@H](c3ccc(Cl)cc3)NCC2)c(F)c1] | 549 | 58 and 12a |
| 73[C]* | 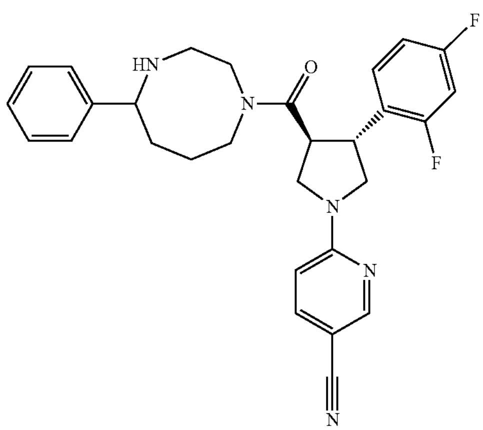 [SMILES: N#Cc1ccc(N2C[C@@H](C(=O)N3CCCC(c4ccccc4)NCC3)[C@H](c3ccc(F)cc3F)C2)nc1] | 502 | 107 and 7 |
| 74[D]* | 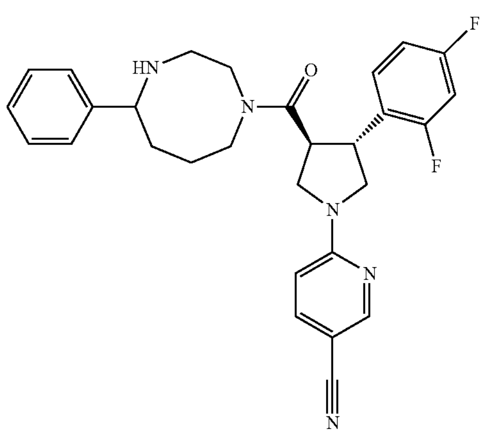 | 502 | 107 and 7 |

| Prep- aration | Structure | MS MH+ ion | Precursors (Prep #) |
|---|---|---|---|
| 75[A] | 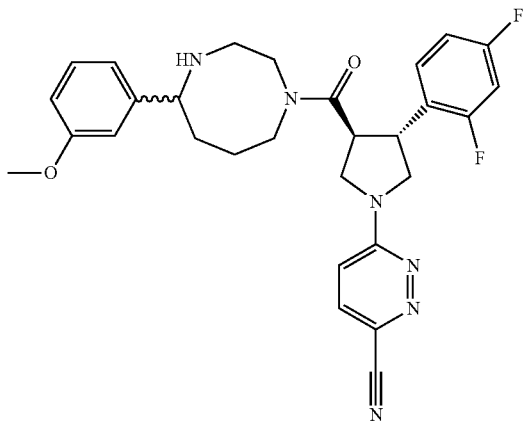 [SMILES: COc1cccc(C2CCCN(C(=O)[C@@H]3CN(c4ccc(C#N)nn4)C[C@H]3c3ccc(F)cc3F)CCN2)c1] | 533 | 52 and 8 |
| 76[A] | 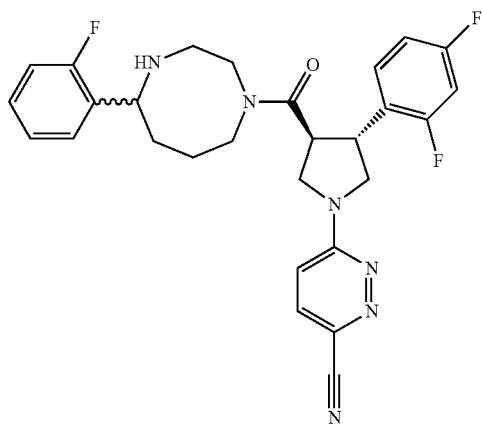 [SMILES: N#Cc1ccc(N2C[C@@H](C(=O)N3CCCC(c4ccccc4F)NCC3)[C@H](c3ccc(F)cc3F)C2)nn1] | 521 | 52 and 9 |
| 77[A] | 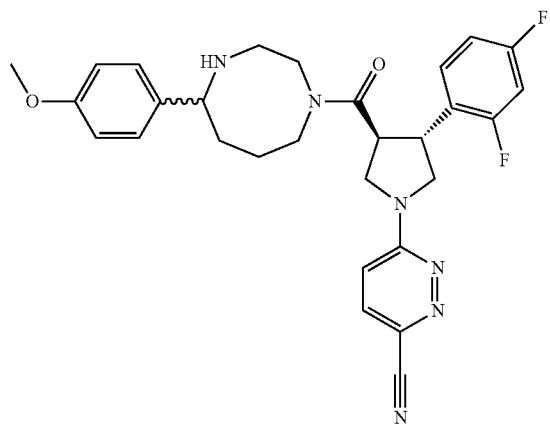 [SMILES: COc1ccc(C2CCCN(C(=O)[C@@H]3CN(c4ccc(C#N)nn4)C[C@H]3c3ccc(F)cc3F)CCN2)cc1] | 533 | 52 and 10 |

-continued
| Prep-aration | Structure | MS MH+ ion | Precursors (Prep #) |
|---|---|---|---|
| 78[B] | 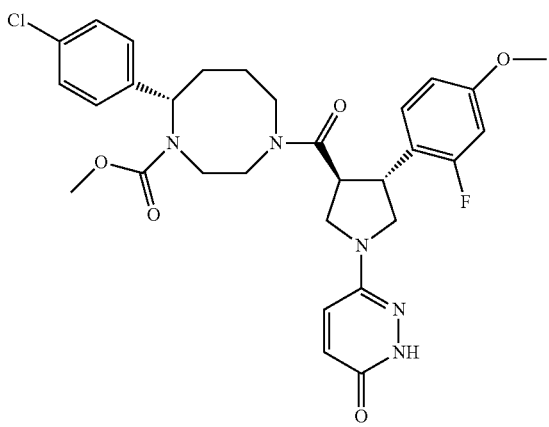 [SMILES: COC(=O)N1CCN(C(=O)[C@@H]2CN(c3ccc(=O)[nH]n3)C[C@H]2c2ccc(OC)cc2F)CCC[C@H]1c1ccc(Cl)cc1] | 598 | 55 and 15a |
| 79[B] | 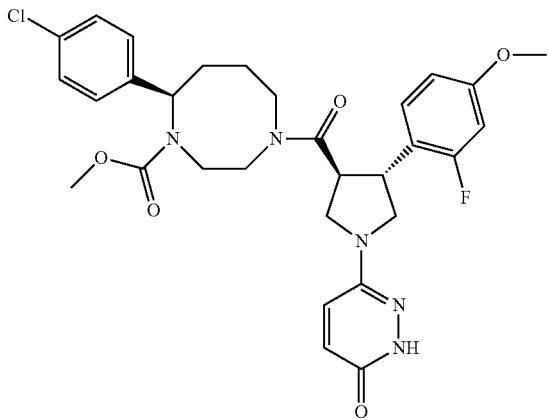 [SMILES: COC(=O)N1CCN(C(=O)[C@@H]2CN(c3ccc(=O)[nH]n3)C[C@H]2c2ccc(OC)cc2F)CCC[C@@H]1c1ccc(Cl)cc1] | 598 | 55 and 15b |
| 80[B] | 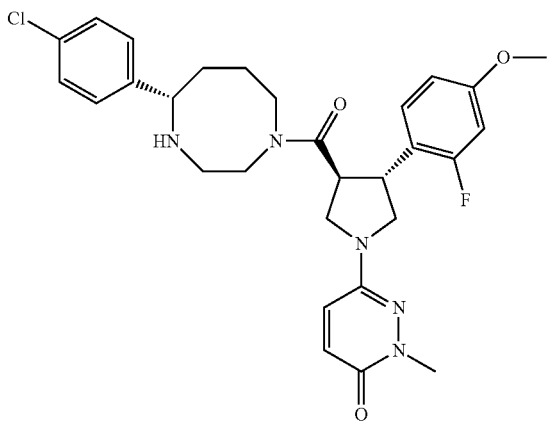 [SMILES: COc1ccc([C@@H]2CN(c3ccc(=O)n(C)n3)C[C@H]2C(=O)N2CCC[C@@H](c3ccc(Cl)cc3)NCC2)c(F)c1] | 554 | 56 and 12a |

-continued
| Preparation | Structure | MS MH+ ion | Precursors (Prep #) |
|---|---|---|---|
| 81[B] | 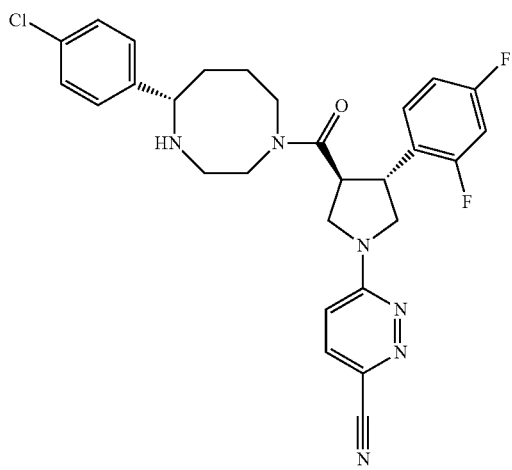 [SMILES: N#Cc1ccc(N2C[C@@H](C(=O)N3CCC[C@@H](c4ccc(Cl)cc4)NCC3)[C@H](c3ccc(F)cc3F)C2)nn1] | 537 | 52 and 12a |
| 82[B] | 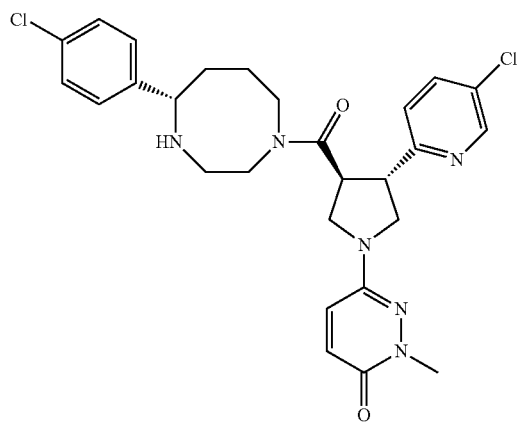 [SMILES: Cn1nc(N2C[C@@H](C(=O)N3CCC[C@@H](c4ccc(Cl)cc4)NCC3)[C@H](c3ccc(Cl)cn3)C2)ccc1=O] | 541 | 108 and 12a |
| 83[A] | 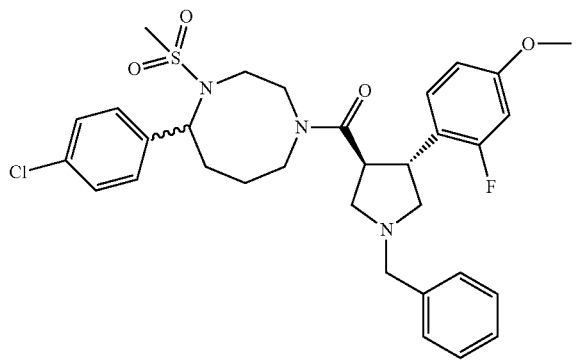 [SMILES: COc1ccc([C@@H]2CN(Cc3ccccc3)C[C@H]2C(=O)N2CCCC(c3ccc(Cl)cc3)N(S(C)(=O)=O)CC2)c(F)c1] | 614 | 54 and 17 |

| Preparation | Structure | MS MH+ ion | Precursors (Prep #) |
|---|---|---|---|
| 84[C*] | 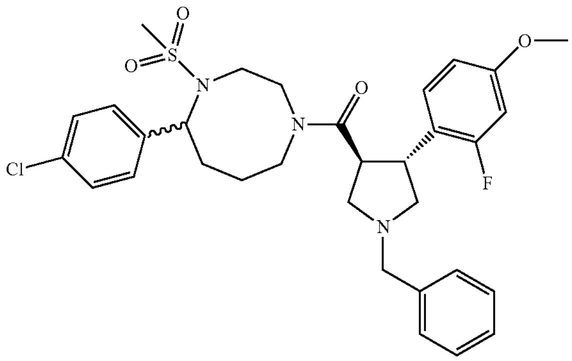 [SMILES: COc1ccc([C@@H]2CN(Cc3ccccc3)C[C@H]2C(=O)N2CCCC(c3ccc(Cl)cc3)N(S(C)(=O)=O)CC2)c(F)c1] | 614 | 54 and 17 |
| 85[D*] | 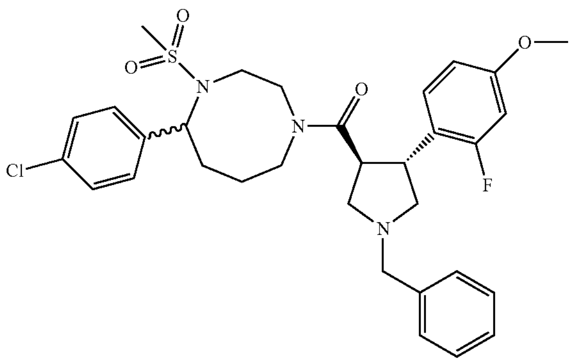 [SMILES: COc1ccc([C@@H]2CN(Cc3ccccc3)C[C@H]2C(=O)N2CCCC(c3ccc(Cl)cc3)N(S(C)(=O)=O)CC2)c(F)c1] | 614 | 54 and 17 |

[A] = mixture of epimers;
[B] = single epimer;
[C] = single epimer of unknown absolute configuration at site of phenyl substitution;
[D] = single epimer of opposite configuration at chloro-phenyl substituent site with respect to prep 73 (respectively prep 84)

Preparations 86-91

These compounds were prepared by the method of example 98 using the appropriate precursors as listed in the table

| Preparation | Structure | MS MH+ ion | Precursors (Prep #) |
|---|---|---|---|
| 86[B] | 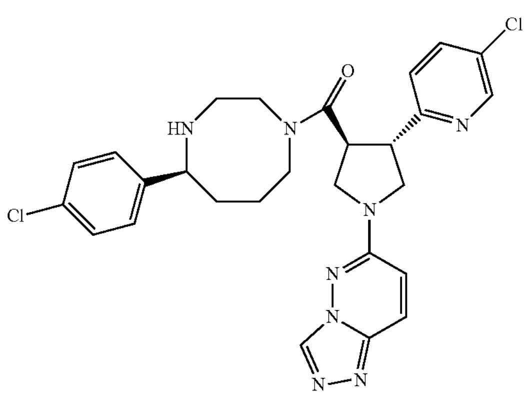 [SMILES: O=C([C@@H]1CN(c2ccc3nncn3n2)C[C@H]1c1ccc(Cl)cn1)N1CCC[C@@H](c2ccc(Cl)cc2)NCC1] | 551 | 59 and 12a |

| Preparation | Structure | MS MH+ ion | Precursors (Prep #) |
|---|---|---|---|
| 87[B] | 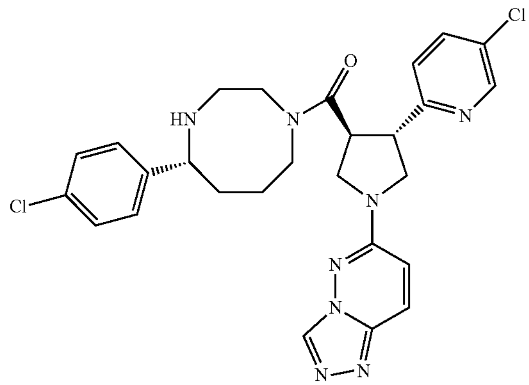 [SMILES: O=C([C@@H]1CN(c2ccc3nncn3n2)C[C@H]1c1ccc(Cl)cn1)N1CCC[C@H](c2ccc(Cl)cc2)NCC1] | 551 | 59 and 12b |
| 88[B] | 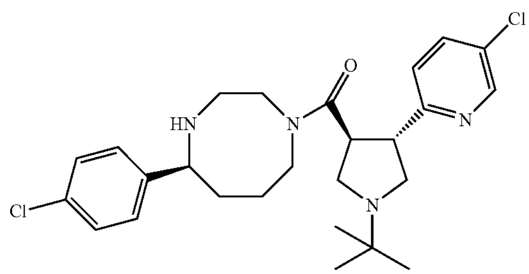 [SMILES: CC(C)(C)N1C[C@@H](C(=O)N2CCC[C@@H](c3ccc(Cl)cc3)NCC2)[C@H](c2ccc(Cl)cn2)C1] | 489 | 53 and 12a |
| 89[B] | 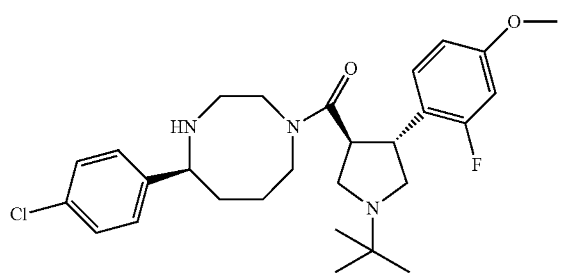 [SMILES: COc1ccc([C@@H]2CN(C(C)(C)C)C[C@H]2C(=O)N2CCC[C@@H](c3ccc(Cl)cc3)NCC2)c(F)c1] | 502 | 57 and 12a |
| 90[B] | 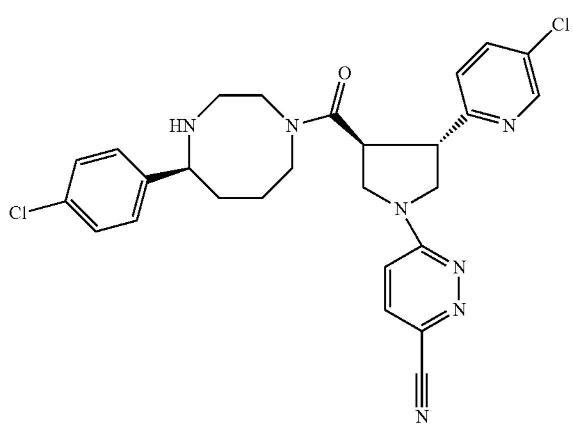 [SMILES: N#Cc1ccc(N2C[C@@H](C(=O)N3CCC[C@@H](c4ccc(Cl)cc4)NCC3)[C@H](c3ccc(Cl)cn3)C2)nn1] | 536 | 65 and 12a |

| Preparation | Structure | MS MH+ ion | Precursors (Prep #) |
|---|---|---|---|
| 91[A] | 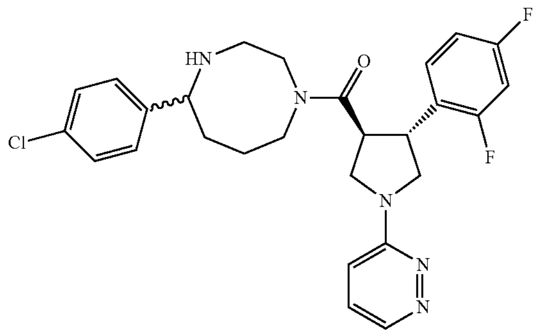 [SMILES: O=C([C@@H]1CN(c2cccnn2)C[C@H]1c1ccc(F)cc1F)N1CCCC(c2ccc(Cl)cc2)NCC1] | 512 | 98 and 6 |

[A] = mixture of epimers;
[B] = single epimer

Preparation 92: 5-(4-chlorophenyl)-1-{[(3S,4R)-4-(2-fluoro-4-methoxyphenyl)pyrrolidin-3-yl]carbonyl}-4-(methylsulfonyl)-1,4-diazocane

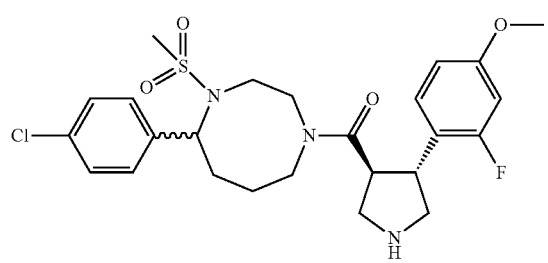 [SMILES: COc1ccc([C@@H]2CNC[C@H]2C(=O)N2CCCC(c3ccc(Cl)cc3)N(S(C)(=O)=O)CC2)c(F)c1]

Diethyl isopropylamine (0.298 mL, 1.71 mmol) was added to a solution of the compound of preparation 83 (239 mg, 0.389 mmol) in DCM (10 mL). 1-chloroethyl chloroformate (0.340 mL, 3.12 mmol) was added and the solution stirred at reflux for 20 h. The reaction was concentrated in vacuo and residue diluted by adding 10% citric acid solution (10 mL) and extracted with DCM (3×15 mL). The combined organic extracts were concentrated in vacuo, the residue dissolved in methanol (10 mL) and stirred at reflux for 2 h. The reaction mixture was concentrated in vacuo to give the crude residue. Purification by column chromatography on silica gel using dichloromethane:methanol:0.880 ammonia (90:10:1) gave 270 mg (100%) of the title compound as a brown oil (as a mixture of two epimers).

$^1$H NMR (400 MHz, CD$_3$OD) δ 1.32-1.67 (2H, m), 2.37-2.50 (3H, m), 2.81-3.25 (2H, m), 3.27-3.31 (3H, m), 3.32-3.94 (12H, m), 4.76-4.87 (1H, m), 6.53-6.72 (2H, m), 6.94-6.99 (1H, m), 7.11-7.16 (1H, m), 7.19-7.36 (3H, m). LRMS: APCl$^+$ m/z 524 [MH$^+$].

Preparations 93-97

These compounds were prepared by the method of preparation 92 using the appropriate precursor as listed in the table.

| Preparation | Structure | MS MH+ ion | Precursor (Prep #) |
|---|---|---|---|
| 93[A] | 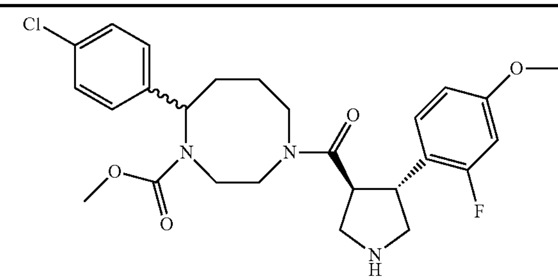 | 504 | 71 |
| 94[C] | 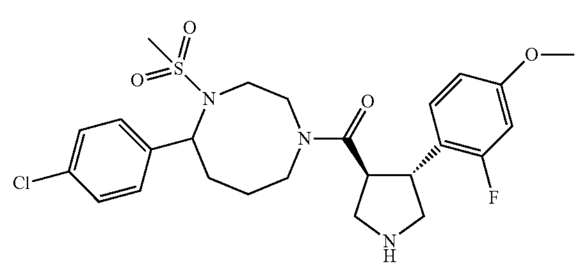 [SMILES: COc1ccc([C@@H]2CNC[C@H]2C(=O)N2CCCC(c3ccc(Cl)cc3)N(S(C)(=O)=O)CC2)c(F)c1] | 524 | 84 |

| Preparation | Structure | MS MH+ ion | Precursor (Prep #) |
|---|---|---|---|
| 95[D] | 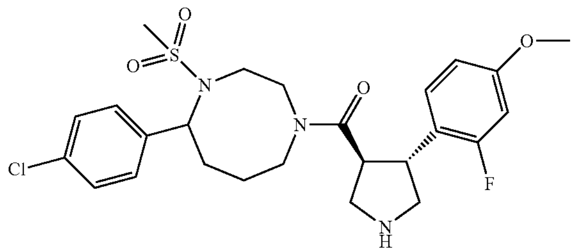 [SMILES: COc1ccc([C@@H]2CNC[C@H]2C(=O)N2CCCC(c3ccc(Cl)cc3)N(S(C)(=O)=O)CC2)c(F)c1] | 524 | 85 |
| 96[B] | 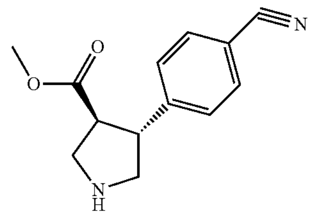 [SMILES: COC(=O)[C@@H]1CNC[C@H]1c1ccc(C#N)cc1] | 231 | 34 |
| 97[E] | 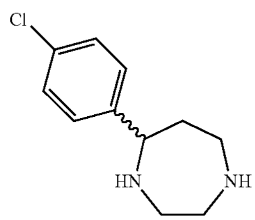 [SMILES: Clc1ccc(C2CCNCCN2)cc1] | 210 | 3 |

[A] = mixture of epimers;
[B] = single enantiomer;
[C] = single epimer of unknown absolute configuration at site of chloro-phenyl substitution;
[D] = single epimer of opposite configuration at site of chloro-phenyl substitution site with respect to compound of preparation 94;
[E] = racemic Preparations 98-108

These compounds are described in the patent literature as listed in the table.

| Preparation | Structure | Patent reference |
|---|---|---|
| 98 | 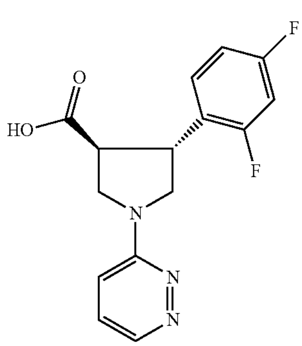 [SMILES: O=C(O)[C@@H]1CN(c2cccnn2)C[C@H]1c1ccc(F)cc1F] | WO2007/015157 preparation 11 |

-continued
| Preparation | Structure | Patent reference |
|---|---|---|
| 99 | 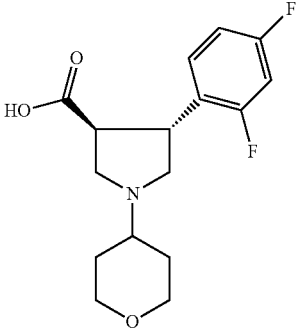 [SMILES: O=C(O)[C@@H]1CN(C2CCOCC2)C[C@H]1c1ccc(F)cc1F] | WO2007/047496 compound 78-6 |
| 100 | 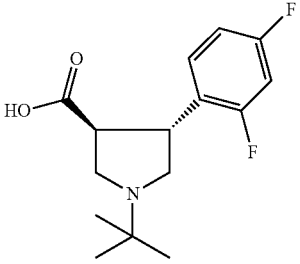 [SMILES: CC(C)(C)N1C[C@@H](C(=O)O)[C@H](c2ccc(F)cc2F)C1] | WO2007/015157 preparation 5 |
| 101 | 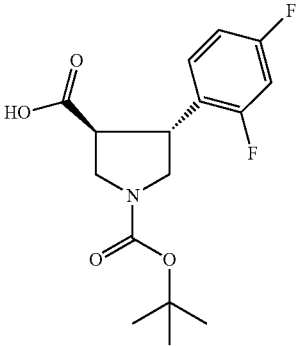 [SMILES: CC(C)(C)OC(=O)N1C[C@@H](C(=O)O)[C@H](c2ccc(F)cc2F)C1] | WO2007/015157 preparation 13 |
| 102 | 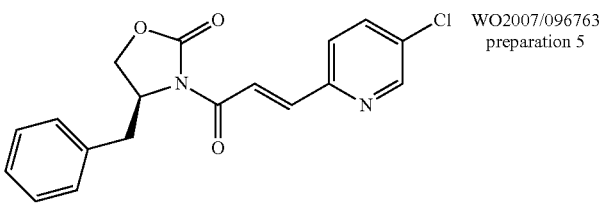 | WO2007/096763 preparation 5 |
| 103 | 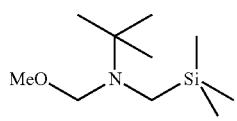 | WO2007/015162 preparation 2 |
| 104 | 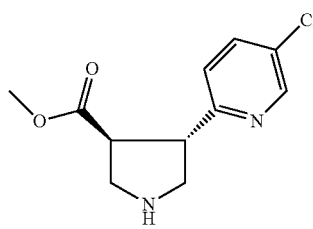 | WO2007/096763 preparation 11 |

| Preparation | Structure | Patent reference |
|---|---|---|
| 105 | 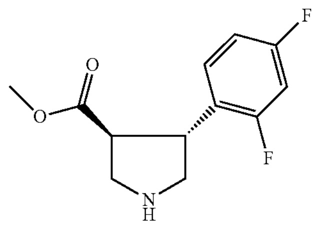 [SMILES: COC(=O)[C@@H]1CNC[C@H]1c1ccc(F)cc1F] | WO2007/015157 preparation 8 |
| 106 | 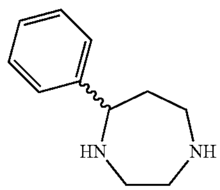 [SMILES: c1ccc(C2CCNCCN2)cc1] | EP899264 example 1D) |
| 107 | 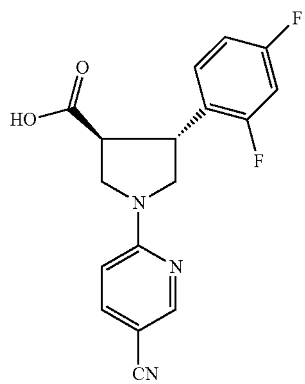 [SMILES: N#Cc1ccc(N2C[C@@H](C(=O)O)[C@H](c3ccc(F)cc3F)C2)nc1] | WO2007/015162 preparation 57 |
| 108 | 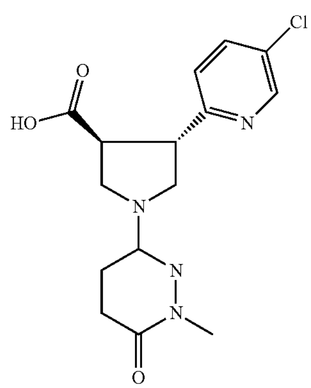 [SMILES: CN1NC(N2C[C@@H](C(=O)O)[C@H](c3ccc(Cl)cn3)C2)CCC1=O] | WO2007096763 preparation 15 |

Biological Data

Data for representative compounds of the invention are given below.

| Example | MC4 EC$_{50}$ (nM) | MC4 MSH Ki (nM) | MC3 EC$_{50}$ (nM) | MC3 MSH Ki (nM) | HLM: Clint, app | % inhibition 3A4 @ 3 μM |
|---|---|---|---|---|---|---|
| 1 | 159 | 2090 | — | 2980 | 31 | 63 |
| 2 | 19 | 269 | — | 375 | 39 | 60 |
| 3 | 42.4 | 521 | — | 3130 | 60 | 30 |
| 4 | 145 | 555 | — | 815 | 237 | 36.5 |
| 5 | 23.2 | 226 | — | 1680 | 17.4 | 80.4 |
| 6 | 1.12 | 28.4 | 300 | 89.5 | 13.5 | 54.2 |
| 7 | 11.9 | — | — | 10100 | 26.2 | — |
| 8 | 52.1 | 1010 | — | 11500 | 17 | 23.9 |
| 9 | 52.8 | 1530 | — | 12600 | 44.7 | 29.1 |
| 10 | 17.3 | 300 | 4190 | 6590 | 22.1 | 37.1 |
| 11 | 6.73 | 200 | 3390 | 4090 | 23.6 | 53.5 |
| 12 | 32.8 | 807 | — | 4150 | 17 | 34 |
| 13 | 13.8 | 366 | — | 5000 | 37.8 | 48.8 |

-continued

| Example | MC4 EC$_{50}$ (nM) | MC4 MSH Ki (nM) | MC3 EC$_{50}$ (nM) | MC3 MSH Ki (nM) | HLM: Clint, app | % inhibition 3A4 @ 3 μM |
|---|---|---|---|---|---|---|
| 14 | 13.4 | 378 | 8590 | 4060 | 82.8 | 56.1 |
| 15 | 10.6 | 144 | 3180 | 3380 | 57.4 | 64.4 |
| 16 | 18.5 | 378 | — | 2100 | 92.6 | 55.5 |
| 17 | 43.3 | 513 | — | 2780 | 118 | 66.9 |
| 18 | 152 | — | — | — | 34 | 24.2 |
| 19 | 64.8 | — | — | — | 62.6 | 41 |
| 20 | 5.46 | 68.6 | 1660 | 386 | 18.1 | 50.2 |
| 21 | 9.42 | — | — | — | — | 35.1 |
| 22 | 5.25 | — | — | — | — | 59.2 |
| 23 | 4.31 | — | — | — | 29.1 | 56.2 |
| 24 | 2.27 | — | — | — | 37.3 | 43.4 |
| 25 | 2.27 | — | — | — | 37.3 | 43.4 |
| 26 | 8.31 | — | — | — | 30.2 | 20.4 |
| 27 | 5.02 | — | — | — | 20.4 | 25.7 |
| 28 | 3.4 | — | — | — | 21.5 | 40.8 |
| 29 | 2.23 | — | 506 | — | 21.4 | 60.8 |
| 30 | 6.01 | — | — | — | 18.2 | 36.8 |
| 31 | 1.23 | 28.2 | 412 | — | 21.8 | 40.8 |
| 32 | 6.63 | — | — | — | 14.8 | — |
| 33 | 3.5 | — | — | — | 17 | 45.2 |
| 34 | 3.9 | — | — | — | 30.9 | 69.2 |
| 35 | 5.29 | — | — | — | — | 68.3 |
| 36 | 7.67 | — | — | — | — | — |
| 37 | 2.11 | — | — | — | 13.9 | 42.3 |
| 38 | 6.9 | — | — | — | — | — |
| 39 | 38 | — | 942 | — | 177 | 87.5 |
| 40 | 29 | — | 607 | — | 156 | 79.5 |
| 41 | 25.1 | — | 6670 | — | 41 | 88 |
| 42 | 122 | 1390 | — | 5370 | 217 | 41 |
| 43 | 397 | — | — | — | 52 | — |
| 44 | 5.58 | — | — | — | 173 | 54.5 |
| 45 | 10.8 | 121 | — | 101 | 234 | 75.8 |
| 46 | 19.7 | — | — | — | 71.1 | 27.3 |
| 47 | 5.11 | — | — | — | 20.6 | 54.2 |
| 48 | 85.5 | 585 | — | 2660 | 55 | 61.5 |
| 49 | 21.1 | 208 | — | 2230 | 86 | 42.5 |
| 50 | 74 | 379 | — | 1610 | 266 | 76.5 |
| 51 | 3.29 | — | — | — | 212 | 75.2 |
| 52 | 35.2 | — | — | — | — | 0 |
| 53 | 14.7 | — | — | — | 27.7 | 58.5 |
| 54 | 44.8 | — | — | — | 32.8 | — |
| 55 | 5.16 | — | — | 154 | 9.75 | 70.6 |
| 56 | 2.99 | 71.1 | 1220 | 187 | 20.5 | 54.2 |
| 57 | 44.8 | — | — | — | 32.8 | — |
| 58 | 22.1 | — | — | — | — | 46.5 |
| 59 | 25.2 | — | — | — | 55.4 | 38.4 |
| 60 | 4.81 | 90.9 | — | — | 31.1 | 44.9 |
| 61 | 25.3 | — | — | — | 13.9 | 40 |
| 62 | 18.4 | 3660 | — | — | — | 0 |
| 63 | 85.3 | — | — | — | 9.43 | 55.6 |
| 64 | 247 | — | — | — | — | — |
| 65 | 16.6 | — | — | 6860 | 23.1 | — |
| 66 | 2.99 | 71.1 | 1220 | 187 | 20.5 | 54.2 |
| 67 | 7.73 | 58.9 | 177 | 162 | 21.4 | 29.5 |
| 68 | 4.3 | 21.7 | 728 | 308 | 13.7 | 29.5 |
| 69 | 7.6 | 16.4 | — | 990 | 8 | 53 |
| 70 | 20.6 | 686 | 4040 | 5880 | 28.3 | 36 |
| 71 | 55.4 | 1050 | — | 10300 | 43.4 | 49.5 |
| 72 | 26.1 | 71.4 | 88.6 | 141 | 13 | 20.4 |
| 73 | 12.2 | 225 | 544 | 981 | 53 | 88 |
| 74 | 86.7 | 1390 | — | 19600 | 74 | 56 |
| 75 | 10.7 | 84.7 | — | 462 | 8 | 73.5 |
| 76 | 50 | 344 | 604 | 960 | 11 | 33.5 |
| 77 | 54.6 | — | 33400 | — | 43 | 56.5 |
| 78 | 40.3 | 303 | 3320 | 3220 | 54 | 49 |
| 79 | 17.1 | 107 | 1820 | 1110 | 22 | 51 |
| 80 | 5.41 | 49.8 | — | 627 | 19 | 70.5 |
| 81 | 20 | 122 | 33300 | 1750 | 18 | 32 |
| 82 | 60.6 | 5180 | — | 19400 | 66 | 47 |
| 83 | 32.1 | 1690 | 33300 | 8110 | 23 | 29 |
| 84 | 206 | — | — | 35300 | 27.9 | — |
| 85 | 404 | — | — | 35300 | 48.4 | 30.5 |
| 86 | 97.2 | — | — | 35300 | 29.6 | 20.3 |
| 87 | 168 | 927 | 33300 | 2150 | — | 50 |
| 88 | 5.38 | 24 | 148 | 153 | 40.1 | 21.5 |
| 89 | 14.3 | 31.3 | 764 | 402 | 42.9 | 28.5 |
| 90 | 1.83 | 12 | 456 | 230 | 11.7 | 53.8 |
| 91 | 20.2 | 383 | 7380 | 4300 | 46.9 | 33 |
| 92 | 274 | 1770 | — | 17900 | 32.4 | 33.5 |
| 93 | 14.5 | — | — | 4900 | 29.3 | 18.9 |
| 94 | 25.6 | — | — | 6690 | 78.1 | 46.6 |
| 95 | 8.18 | — | — | 4040 | 41.7 | 41.9 |
| 96 | 0.852 | — | — | — | 31.3 | 76.9 |
| 97 | 157 | 1620 | — | 3720 | 247 | 63 |
| 98 | 5.26 | 52 | — | 201 | 13.9 | 46.9 |
| 99 | 27.6 | 626 | 33400 | 2970 | 313 | 61.5 |
| 100 | 7.16 | 189 | 436 | — | 83 | 65.5 |
| 101 | 7.12 | 77.9 | 114 | 715 | 143 | 83 |
| 102 | 12 | 174 | — | 545 | 16 | 65 |
| 103 | 9.79 | 316 | 332 | 1540 | 102 | 53.8 |
| 104 | 18 | 583 | — | 9080 | 69.2 | 48 |
| 105 | 36.1 | 92.2 | 33300 | 571 | 42 | 37.5 |
| 106 | 6.4 | 28.5 | — | 250 | 38 | 66.5 |
| 107 | 27.7 | 96.4 | — | 683 | 47 | 55.5 |
| 108 | 123 | 180 | 33400 | 875 | 59 | 63.5 |
| 111 | 14.7 | 68.4 | 33300 | 942 | 24 | 66.5 |
| 112 | 3.38 | 17.4 | — | 404 | 15 | 65.5 |
| 113 | 12.7 | 50.5 | — | 1300 | 24.8 | 44.3 |
| 114 | 73.4 | 20.8 | — | 1150 | 16.4 | 27.5 |
| 115 | 15.7 | 53.9 | 33300 | 1090 | 22.7 | 58.2 |
| 116 | 3.6 | 24.3 | — | 573 | 12 | 75 |
| 117 | 34.9 | 33.6 | 8360 | 1150 | 35.1 | 44.5 |
| 118 | 1.83 | 24.7 | 8200 | 178 | 23.2 | 48 |
| 119 | 8.53 | 22.3 | 11200 | 900 | 18.8 | 54.5 |

— not determined

The invention claimed is:

1. A compound of formula (I):

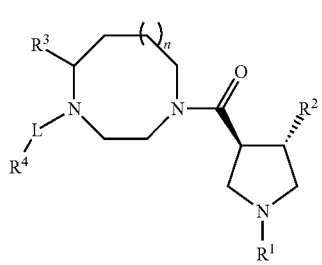

(I)

or pharmaceutically acceptable salts and solvates thereof, wherein:

n is 0 or 1;

R$^1$ is —(C$_1$-C$_4$)alkyl, or Het$^1$;

R$^2$ is phenyl or pyridyl, wherein said phenyl or pyridyl is optionally substituted by one to three substituents independently selected from halo, CN, —(C$_1$-C$_4$)alkyl and —(C$_1$-C$_4$)alkoxy wherein the —(C$_1$-C$_4$)alkyl and —(C$_1$-C$_4$)alkoxy groups are optionally substituted with 1 to 3 fluorine atoms;

R$^3$ is phenyl or pyridyl, wherein said phenyl or pyridyl is optionally substituted by one to three substituents independently selected from halo, CN, —(C$_1$-C$_4$)alkyl and —(C$_1$-C$_4$)alkoxy wherein the —(C$_1$-C$_4$)alkyl and —(C$_1$-C$_4$)alkoxy groups are optionally substituted with 1 to 3 fluorine atoms;

either L is —CO— and R$^4$ is —(C$_1$-C$_4$)alkyl, —(C$_1$-C$_4$)alkoxy, —(C$_3$-C$_6$)cycloalkyl, —(C$_1$-C$_2$)alkyl(C$_3$-C$_6$)cycloalkyl, —(C$_1$-C$_2$)alkyl(C$_1$-C$_4$)alkoxy, —NH$_2$, —NH(C$_1$-C$_4$)alkyl, —N[(C$_1$-C$_4$)alkyl]$_2$ or Het$^2$, wherein the —(C$_1$-C$_4$)alkyl group is optionally substituted with 1 to 3 fluorine atoms and wherein the —(C$_3$-C$_6$)cycloalkyl group is optionally substituted with 1 to 3 fluorine atoms or —(C$_1$-C$_4$)alkyl groups;

or L is —SO$_2$— and R$^4$ is —(C$_1$-C$_4$)alkyl; —(C$_3$-C$_6$)cycloalkyl, —(C$_1$-C$_2$)alkyl(C$_3$-C$_6$)cycloalkyl, —(C$_1$-C$_2$)alkyl(C$_1$-C$_4$)alkoxy, —NH$_2$, —NH(C$_1$-C$_4$)alkyl, —N[(C$_1$-C$_4$)alkyl]$_2$, or Het$^2$;

Het$^1$ is
(i) a 6-membered ring containing one or 2 N atoms, wherein the ring is either aromatic, or contains 2 double bonds in the ring and a =O substituent, which ring is optionally substituted by one to three substituents independently selected from halo, CN, and —(C$_1$-C$_4$)alkyl;
(ii) a 6-membered aromatic ring containing one or 2 N atoms fused at the 3,4-positions, relative to the attachment to the pyrrolidine ring, to a 5-membered aromatic ring containing one to three further N atoms; or
(iii) tetrahydropyranyl;

Het$^2$ is
(i) a 5-membered aromatic ring containing one or 2 N atoms and a further optional O atom, S atom or N atom,
(ii) a 4- to 6-membered saturated ring containing one N atom; or
(iii) a 6-membered saturated ring containing one O atom and a further optional N atom.

2. The compound according to claim 1, or pharmaceutically acceptable salts and solvates thereof, wherein R$^1$ is —(C$_1$-C$_4$)alkyl.

3. The compound according to claim 1, or pharmaceutically acceptable salts and solvates thereof, wherein R$^1$ is Het$^1$ where Het$^1$ is
(i) a 6-membered ring containing one or 2 N atoms, wherein the ring is either aromatic, or contains 2 double bonds in the ring and a =O substituent, which ring is optionally substituted by a substituent selected from halo, CN, and —(C$_1$-C$_4$)alkyl; or
(ii) a 6-membered aromatic ring containing one or 2 N atoms fused at the 3,4-positions, relative to the attachment to the pyrrolidine ring, to a 5-membered aromatic ring containing one or two further N atoms.

4. The compound according to claim 3, or pharmaceutically acceptable salts and solvates thereof, wherein R$^1$ is Het$^1$ where Het$^1$ is pyridin-2-yl, pyridin-3-yl, pyridazin-3-yl, 6-oxo-1,6-dihydropyridazin-3-yl, 6-oxo-1,6-dihydropyridin-3-yl, 2-oxo-1,2-dihydropyrimidin-4-yl, 6-oxo-1,6-dihydropyrimidin-4-yl, 2-oxo-1,2-dihydropyridin-4-yl, [1,2,4]triazolo[4,3-b]pyridazin-6-yl or 6-oxo-1,6-dihydropyridin-2-yl, optionally substituted by one or two substituents independently selected from —(C$_1$-C$_4$)alkyl, halo and CN.

5. The compound according to claim 4, or pharmaceutically acceptable salts and solvates thereof, wherein R$^1$ is Het$^1$ where Het$^1$ is 6-oxo-1,6-dihydropyridazin-3-yl, 1-methyl-6-oxo-1,6-dihydropyridazin-3-yl, or [1,2,4]triazolo[4,3-b]pyridazin-6-yl.

6. The compound according to any one of claims 1 to 5, or pharmaceutically acceptable salts and solvates thereof, wherein R$^2$ is phenyl or pyridyl, wherein said phenyl or pyridyl is optionally substituted by one or two substituents independently selected from halo, CN, —(C$_1$-C$_4$)alkyl and —(C$_1$-C$_4$)alkoxy.

7. The compound according to any one of claims 1 to 6, or pharmaceutically acceptable salts and solvates thereof, wherein R$^3$ is phenyl optionally substituted by one or two substituents independently selected from halo and (C$_1$-C$_4$)alkoxy.

8. The compound according to any one of claims 1 to 7, or pharmaceutically acceptable salts and solvates thereof, wherein L is —CO— and R$^4$ is —(C$_1$-C$_4$)alkyl optionally substituted with 1 to 3 fluorine atoms, —(C$_1$-C$_4$)alkoxy, —(C$_3$-C$_6$)cycloalkyl optionally substituted with 1 or 2 fluorine atoms or —(C$_1$-C$_4$)alkyl groups, —(C$_1$-C$_2$)alkyl(C$_3$-C$_6$)cycloalkyl, —(C$_1$-C$_2$)alkyl(C$_1$-C$_4$)alkoxy, —NH(C$_1$-C$_4$)alkyl, —N[(C$_1$-C$_4$)alkyl]$_2$ or Het$^2$ wherein Het$^2$ is a 5-membered aromatic ring containing 2 N atoms or a 6-membered saturated ring containing one O atom and a further optional N atom.

9. The compound according to claim 8, or pharmaceutically acceptable salts and solvates thereof, wherein L is —CO— and R$^4$ is —(C$_1$-C$_4$)alkyl or —(C$_1$-C$_4$)alkoxy wherein the —(C$_1$-C$_4$)alkyl group is optionally substituted with 1 to 3 fluorine atoms.

10. The compound according to any one of claims 1 to 9, or pharmaceutically acceptable salts and solvates thereof, wherein n is 1.

11. A compound selected from:
6-[(3S,4R)-3-{[5S-(4-chlorophenyl)-4-(3,3,3-trifluoropropanoyl)-1,4-diazocan-1-yl]carbonyl}-4-(2-fluoro-4-methoxyphenyl)pyrrolidin-1-yl]-2-methylpyridazin-3(2H)-one;
6-[(3S,4R)-3-{[5S-(4-chlorophenyl)-4-isobutyryl-1,4-diazocan-1-yl]carbonyl}-4-(2,4-difluorophenyl)pyrrolidin-1-yl]-2-methylpyridazin-3(2H)-one;
6-[(3S,4S)-3-{[5S-(4-chlorophenyl)-4-isobutyryl-1,4-diazocan-1-yl]carbonyl}-4-(5-chloropyridin-2-yl)pyrrolidin-1-yl]-2-methylpyridazin-3(2H)-one;
methyl 8-(4-chlorophenyl)-4-{[(3S,4R)-4-(2-fluoro-4-methoxyphenyl)-1-(6-oxo-1,6-dihydropyridazin-3-yl)pyrrolidin-3-yl]carbonyl}-1,4-diazocane-1-carboxylate;
methyl 8S-(4-chlorophenyl)-4-{[(3S,4R)-4-(2-fluoro-4-methoxyphenyl)-1-(6-oxo-1,6-dihydropyridazin-3-yl)pyrrolidin-3-yl]carbonyl}-1,4-diazocane-1-carboxylate;
methyl 8R-(4-chlorophenyl)-4-{[(3S,4R)-4-(2-fluoro-4-methoxyphenyl)-1-(6-oxo-1,6-dihydropyridazin-3-yl)pyrrolidin-3-yl]carbonyl}-1,4-diazocane-1-carboxylate;
methyl 8R-(4-chlorophenyl)-4-{[(3S,4R)-4-(2-fluoro-4-methoxyphenyl)-1-(1-methyl-6-oxo-1,6-dihydropyridazin-3-yl)pyrrolidin-3-yl]carbonyl}-1,4-diazocane-1-carboxylate;
6-[(3S,4R)-3-{[4-acetyl-5S-(4-chlorophenyl)-1,4-diazocan-1-yl]carbonyl}-4-(2-fluoro-4-methoxyphenyl)pyrrolidin-1-yl]pyridazin-3(2H)-one;
methyl 8S-(4-chlorophenyl)-4-{[(3S,4S)-4-(5-chloropyridin-2-yl)-1-(6-cyanopyridazin-3-yl)pyrrolidin-3-yl]carbonyl}-1,4-diazocane-1-carboxylate;
1-{[(3S,4S)-1-tert-butyl-4-(5-chloropyridin-2-yl)pyrrolidin-3-yl]carbonyl}-5S-(4-chlorophenyl)-4-isobutyryl-1,4-diazocane;
6-[(3S,4S)-3-{[4-acetyl-5S-(4-chlorophenyl)-1,4-diazocan-1-yl]carbonyl}-4-(5-chloropyridin-2-yl)pyrrolidin-1-yl][1,2,4]triazolo[4,3-b]pyridazine;
methyl 8S-(4-chlorophenyl)-4-{[(3S,4R)-4-(2,4-difluorophenyl)-1-(1-methyl-6-oxo-1,6-dihydropyridazin-3-yl)pyrrolidin-3-yl]carbonyl}-1,4-diazocane-1-carboxylate;
and pharmaceutically acceptable salts and solvates thereof.

12. A pharmaceutical composition comprising a compound according to any one of claims 1 to 11, or a pharmaceutically acceptable salt or solvate thereof, and a pharmaceutically acceptable diluent, carrier or adjuvant.

13. A method of treating a disorder which would benefit from agonism of the MC4 receptor which comprises administering to a subject in need thereof a therapeutically effective amount of a compound, salt or solvate according to any one of claims 1 to 11, wherein said disorder is obesity.

14. A method of treating a disorder which would benefit from agonism of the MC4 receptor which comprises administering to a subject in need thereof a therapeutically effective amount of a compound, salt or solvate according to any one of claims 1 to 11, wherein said disorder is erectile disfunction.

* * * * *